(12) United States Patent
Dong et al.

(10) Patent No.: US 10,259,875 B2
(45) Date of Patent: Apr. 16, 2019

(54) METHODS FOR TREATING CANCER IN PATIENTS WITH ELEVATED LEVELS OF BIM

(71) Applicant: Mayo Foundation for Medical Education and Research, Rochester, MN (US)

(72) Inventors: Haidong Dong, Rochester, MN (US); Susan M. Harrington, Rochester, MN (US); Eugene D. Kwon, Rochester, MN (US); Christopher J. Krco, Rochester, MN (US); Xin Liu, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/026,461

(22) PCT Filed: Sep. 3, 2014

(86) PCT No.: PCT/US2014/053870
§ 371 (c)(1),
(2) Date: Mar. 31, 2016

(87) PCT Pub. No.: WO2015/050663
PCT Pub. Date: Apr. 9, 2015

(65) Prior Publication Data
US 2016/0251437 A1    Sep. 1, 2016

Related U.S. Application Data

(60) Provisional application No. 61/885,218, filed on Oct. 1, 2013.

(51) Int. Cl.
| C07K 16/28 | (2006.01) |
| G01N 33/574 | (2006.01) |
| C12Q 1/6886 | (2018.01) |
| A61K 39/00 | (2006.01) |

(52) U.S. Cl.
CPC ...... C07K 16/2827 (2013.01); C07K 16/2818 (2013.01); C12Q 1/6886 (2013.01); G01N 33/57484 (2013.01); *A61K 2039/505* (2013.01); *C07K 2317/76* (2013.01); *C12Q 2600/106* (2013.01); *C12Q 2600/158* (2013.01); *G01N 2333/47* (2013.01); *G01N 2800/52* (2013.01)

(58) Field of Classification Search
None
See application file for complete search history.

(56) References Cited

U.S. PATENT DOCUMENTS

| 3,687,808 A | 8/1972 | Merigan, Jr. et al. |
| 4,034,074 A | 7/1977 | Miles |
| 4,036,945 A | 7/1977 | Haber |
| 4,098,876 A | 7/1978 | Piasio et al. |
| 4,233,402 A | 11/1980 | Maggio et al. |
| 4,257,774 A | 3/1981 | Richardson et al. |
| 4,272,398 A | 6/1981 | Jaffe |
| 4,331,647 A | 5/1982 | Goldenberg |
| 4,376,110 A | 3/1983 | David et al. |
| 4,469,863 A | 9/1984 | Ts'o et al. |
| 4,650,764 A | 3/1987 | Temin et al. |
| 4,769,330 A | 9/1988 | Paoletti et al. |
| 4,816,567 A | 3/1989 | Cabilly et al. |
| 4,861,627 A | 8/1989 | Mathiowitz et al. |
| 4,861,719 A | 8/1989 | Miller |
| 4,925,673 A | 5/1990 | Steiner et al. |
| 4,935,496 A | 6/1990 | Kudo et al. |
| 4,946,778 A | 8/1990 | Ladner et al. |
| 4,980,289 A | 12/1990 | Temin et al. |
| 4,987,071 A | 1/1991 | Cech et al. |
| 5,013,556 A | 5/1991 | Woodle et al. |
| 5,124,263 A | 6/1992 | Temin et al. |
| 5,155,020 A | 10/1992 | Paoletti |
| 5,155,027 A | 10/1992 | Sledziewski et al. |
| 5,175,099 A | 12/1992 | Wills |
| 5,204,243 A | 4/1993 | Paoletti |
| 5,214,136 A | 5/1993 | Lin et al. |
| 5,218,105 A | 6/1993 | Cook et al. |

(Continued)

FOREIGN PATENT DOCUMENTS

| EP | 1 074 617 | 2/2001 |
| EP | 1 537 878 | 6/2005 |

(Continued)

OTHER PUBLICATIONS

Gibbons et al, Oncoimmunology 1:7 1061-1073, 2012.*

(Continued)

*Primary Examiner* — Lei Yao
(74) *Attorney, Agent, or Firm* — Fish & Richardson P.C.

(57) ABSTRACT

Materials and methods for treating cancer especially in patients identified as having elevated levels of Bim are disclosed. Specifically, the disclosure provides a method for treating a mammal having cancer, the method comprises: (a) identifying said mammal as containing an elevated level of Bim, and (b) administering to said mammal an anti-B7-H1 antibody, an anti-PD-1 antibody, an anti-CD80 antibody, or a fusion protein comprising a portion of PD1 or a portion of CD80, under conditions wherein the interaction of naturally occurring B7-H1 with PD-1 or CD80 in said mammal is reduced after said administering.

10 Claims, 25 Drawing Sheets

Specification includes a Sequence Listing.

(56) References Cited

U.S. PATENT DOCUMENTS

| | | |
|---|---|---|
| 5,225,336 A | 7/1993 | Paoletti |
| 5,225,538 A | 7/1993 | Capon et al. |
| 5,235,033 A | 8/1993 | Summerton et al. |
| 5,240,846 A | 8/1993 | Collins et al. |
| 5,254,678 A | 10/1993 | Haseloff et al. |
| 5,278,056 A | 1/1994 | Bank et al. |
| 5,284,656 A | 2/1994 | Platz et al. |
| 5,296,347 A | 3/1994 | LaMotte, III |
| 5,391,682 A | 2/1995 | Ogawa et al. |
| 5,451,569 A | 9/1995 | Wong et al. |
| 5,502,167 A | 3/1996 | Waldmann et al. |
| 5,521,288 A | 5/1996 | Linsley et al. |
| 5,530,101 A | 6/1996 | Queen et al. |
| 5,558,864 A | 9/1996 | Bendig et al. |
| 5,565,332 A | 10/1996 | Hoogenboom et al. |
| 5,567,584 A | 10/1996 | Sledziewski et al. |
| 5,585,089 A | 12/1996 | Queen et al. |
| 5,596,086 A | 1/1997 | Matteucci et al. |
| 5,639,641 A | 6/1997 | Pedersen et al. |
| 5,674,704 A | 10/1997 | Goodwin et al. |
| 5,675,848 A | 10/1997 | Kappel |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,705,154 A | 1/1998 | Dalie et al. |
| 5,714,147 A | 2/1998 | Capon et al. |
| 5,733,743 A | 3/1998 | Johnson et al. |
| 5,750,078 A | 5/1998 | Shitara et al. |
| 5,750,375 A | 5/1998 | Sledziewski et al. |
| 5,750,666 A | 5/1998 | Caruthers et al. |
| 5,770,403 A | 6/1998 | Dalie et al. |
| 5,843,725 A | 12/1998 | Sledziewski et al. |
| 5,861,310 A | 1/1999 | Freeman et al. |
| 5,874,240 A | 2/1999 | Ni et al. |
| 5,928,893 A | 7/1999 | Kang et al. |
| 5,942,607 A | 8/1999 | Freeman et al. |
| 6,018,026 A | 1/2000 | Sledziewski et al. |
| 6,210,669 B1 | 4/2001 | Aruffo et al. |
| 6,291,212 B1 | 9/2001 | Sledziewski et al. |
| 6,291,646 B1 | 9/2001 | Sledziewski et al. |
| 6,297,008 B1 | 10/2001 | Okamoto et al. |
| 6,300,099 B1 | 10/2001 | Sledziewski et al. |
| 6,303,121 B1 | 10/2001 | Kwon |
| 6,323,323 B1 | 11/2001 | Sledziewski et al. |
| 6,355,779 B1 | 3/2002 | Goodwin et al. |
| 6,423,885 B1 | 7/2002 | Waterhouse et al. |
| 6,458,934 B1 | 10/2002 | Hong et al. |
| 6,630,575 B2 | 10/2003 | Coyle et al. |
| 6,635,750 B1 | 10/2003 | Coyle et al. |
| 6,740,493 B1 | 5/2004 | Long et al. |
| 6,743,619 B1 | 6/2004 | Tang et al. |
| 6,803,192 B1 | 10/2004 | Chen |
| 6,891,030 B2 | 5/2005 | Chen |
| 6,919,193 B2 | 7/2005 | Tang et al. |
| 6,943,150 B1 | 9/2005 | Altieri |
| 6,965,018 B2 | 11/2005 | Mikesell et al. |
| 7,029,674 B2 | 4/2006 | Carreno et al. |
| 7,030,219 B2 | 4/2006 | Pardoll et al. |
| 7,122,351 B2 | 10/2006 | Moore et al. |
| 7,279,567 B2 | 10/2007 | Mikesell et al. |
| 7,358,354 B2 | 4/2008 | Mikesell et al. |
| 7,368,531 B2 | 5/2008 | Rosen et al. |
| 7,381,794 B2 | 6/2008 | Moore et al. |
| 7,414,122 B2 | 8/2008 | Fox et al. |
| 7,432,059 B2 | 10/2008 | Freeman et al. |
| 7,432,062 B2 | 10/2008 | Coyle et al. |
| 7,432,351 B1 | 10/2008 | Chen |
| 7,449,300 B2 | 11/2008 | Chen et al. |
| 7,560,540 B2 | 7/2009 | Pardoll et al. |
| 7,563,869 B2 | 7/2009 | Honjo et al. |
| 7,582,439 B2 | 9/2009 | Cory et al. |
| 7,595,048 B2 | 9/2009 | Honjo et al. |
| 7,651,686 B2 | 1/2010 | Chen et al. |
| 7,709,214 B2 | 5/2010 | Freeman et al. |
| 7,723,479 B2 | 5/2010 | Mikesell et al. |
| 7,794,710 B2 | 9/2010 | Chen et al. |
| 7,892,540 B2 | 2/2011 | Chen et al. |
| 8,039,589 B1 | 10/2011 | Chen |
| 8,053,414 B2 | 11/2011 | Pardoll et al. |
| 8,053,558 B2 | 11/2011 | Pardoll et al. |
| 8,163,550 B2 | 4/2012 | Chen et al. |
| 8,268,635 B2 | 9/2012 | Ferrante et al. |
| 8,273,864 B2 | 9/2012 | Chen |
| 8,460,927 B2 | 6/2013 | Chen |
| 8,772,026 B2 | 7/2014 | Chen et al. |
| 8,981,063 B2 | 3/2015 | Chen |
| 9,302,005 B2 | 4/2016 | Dong et al. |
| 2002/0076409 A1 | 6/2002 | March et al. |
| 2002/0091246 A1 | 7/2002 | Pardoll et al. |
| 2002/0095024 A1 | 7/2002 | Mikesell et al. |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0119121 A1 | 8/2002 | Vitiello et al. |
| 2002/0160395 A1 | 10/2002 | Altieri et al. |
| 2002/0160973 A1 | 10/2002 | Pero et al. |
| 2002/0164600 A1 | 11/2002 | Freeman et al. |
| 2002/0168719 A1 | 11/2002 | Kwon |
| 2002/0177551 A1 | 11/2002 | Terman |
| 2003/0039653 A1 | 2/2003 | Chen et al. |
| 2003/0142359 A1 | 7/2003 | Bean et al. |
| 2003/0171551 A1 | 9/2003 | Rosenblatt et al. |
| 2003/0208058 A1 | 11/2003 | Fiscella et al. |
| 2003/0223989 A1 | 12/2003 | Pluenneke |
| 2003/0232323 A1 | 12/2003 | Freeman et al. |
| 2004/0010134 A1 | 1/2004 | Rosen et al. |
| 2004/0109847 A1 | 6/2004 | Chen et al. |
| 2004/0180047 A1 | 9/2004 | Chen |
| 2004/0247563 A1 | 12/2004 | Lynch et al. |
| 2005/0013811 A1 | 1/2005 | Chen et al. |
| 2005/0228170 A1 | 10/2005 | Fox et al. |
| 2005/0260716 A1 | 11/2005 | Moore et al. |
| 2006/0034826 A1 | 2/2006 | Carreno et al. |
| 2006/0068386 A1 | 3/2006 | Slesarev et al. |
| 2006/0084794 A1 | 4/2006 | Rosen et al. |
| 2006/0110383 A1 | 5/2006 | Honjo et al. |
| 2006/0159685 A1 | 7/2006 | Mikesell et al. |
| 2006/0223088 A1 | 10/2006 | Rosen et al. |
| 2006/0276422 A1 | 12/2006 | Usman et al. |
| 2007/0037206 A1 | 2/2007 | Rosen et al. |
| 2007/0041963 A1 | 2/2007 | Rosen et al. |
| 2007/0065427 A1 | 3/2007 | Freeman et al. |
| 2007/0092504 A1 | 4/2007 | Carreno et al. |
| 2007/0099833 A1 | 5/2007 | Rosen et al. |
| 2007/0122378 A1 | 5/2007 | Freeman et al. |
| 2007/0224663 A1 | 9/2007 | Rosen et al. |
| 2007/0231344 A1 | 10/2007 | Leadbetter et al. |
| 2008/0025979 A1 | 1/2008 | Honjo et al. |
| 2008/0118511 A1 | 5/2008 | Freeman et al. |
| 2008/0226662 A1 | 9/2008 | Pardoll et al. |
| 2008/0241175 A1 | 10/2008 | Pardoll et al. |
| 2009/0042292 A1 | 2/2009 | Chen |
| 2009/0068193 A1 | 3/2009 | Chen et al. |
| 2009/0075338 A1 | 3/2009 | Moore et al. |
| 2009/0176317 A1 | 7/2009 | Kwon et al. |
| 2009/0215084 A1 | 8/2009 | Kwon et al. |
| 2009/0269783 A1 | 10/2009 | Coyle et al. |
| 2009/0304711 A1 | 12/2009 | Pardoll et al. |
| 2010/0015642 A1 | 1/2010 | Kwon et al. |
| 2010/0285039 A1 | 11/2010 | Chen |
| 2011/0020325 A1 | 1/2011 | Kwon et al. |
| 2011/0010409 A1 | 5/2011 | Strome et al. |
| 2012/0065374 A1 | 3/2012 | Pardoll et al. |
| 2012/0065385 A1 | 3/2012 | Pardoll et al. |
| 2012/0225043 A1 | 9/2012 | Chen et al. |
| 2013/0058936 A1 | 3/2013 | Bruenker et al. |
| 2013/0123566 A1 | 5/2013 | Lupold et al. |
| 2013/0251736 A1 | 9/2013 | Kwon et al. |
| 2013/0273656 A1 | 10/2013 | Hendrickson |
| 2014/0242080 A1 | 8/2014 | Roche |
| 2014/0271674 A1 | 9/2014 | Dong |
| 2014/0329248 A1 | 11/2014 | Kwon et al. |
| 2014/0335541 A1 | 11/2014 | Kwon et al. |

(56) References Cited

U.S. PATENT DOCUMENTS

| | | |
|---|---|---|
| 2015/0111232 A1 | 4/2015 | Kwon |
| 2016/0153996 A1 | 6/2016 | Kwon et al. |
| 2016/0154000 A1 | 6/2016 | Kwon |
| 2016/0176967 A1 | 6/2016 | Dong et al. |
| 2017/0089918 A1 | 3/2017 | Dong |
| 2017/0173030 A1 | 6/2017 | Dong |

FOREIGN PATENT DOCUMENTS

| | | |
|---|---|---|
| WO | WO 1990/07861 | 7/1990 |
| WO | WO 1991/10741 | 7/1991 |
| WO | WO 1991/11465 | 8/1991 |
| WO | WO 1991/17271 | 11/1991 |
| WO | WO 1992/00092 | 1/1992 |
| WO | WO 1992/01047 | 1/1992 |
| WO | WO 1992/20791 | 11/1992 |
| WO | WO 1993/01222 | 1/1993 |
| WO | WO 1995/05464 | 2/1995 |
| WO | WO 1995/07707 | 3/1995 |
| WO | WO 1996/29348 | 9/1996 |
| WO | WO 1997/17613 | 5/1997 |
| WO | WO 1997/17614 | 5/1997 |
| WO | WO 1997/24447 | 7/1997 |
| WO | WO 1998/16249 | 4/1998 |
| WO | WO 1998/23635 | 6/1998 |
| WO | WO 1998/33914 | 8/1998 |
| WO | WO 1998/36096 | 8/1998 |
| WO | WO 1999/36093 | 7/1999 |
| WO | WO 1999/64597 | 12/1999 |
| WO | WO 2000/026342 | 5/2000 |
| WO | WO 2000/029445 | 5/2000 |
| WO | WO 2000/029582 | 5/2000 |
| WO | WO 2000/041508 | 7/2000 |
| WO | WO 2000/055375 | 9/2000 |
| WO | WO 2000/061612 | 10/2000 |
| WO | WO 2001/034629 | 5/2001 |
| WO | WO 2001/062905 | 8/2001 |
| WO | WO 2001/070979 | 9/2001 |
| WO | WO 2001/083750 | 11/2001 |
| WO | WO 2001/094413 | 12/2001 |
| WO | WO 2002/000692 | 1/2002 |
| WO | WO 2002/000730 | 1/2002 |
| WO | WO 2002/002587 | 1/2002 |
| WO | WO 2002/002891 | 1/2002 |
| WO | WO 2002/008279 | 1/2002 |
| WO | WO 2002/078731 | 1/2002 |
| WO | WO 2002/024891 | 3/2002 |
| WO | WO 2002/046449 | 6/2002 |
| WO | WO 2002/057453 | 7/2002 |
| WO | WO 2002/079474 | 10/2002 |
| WO | WO 2002/081731 | 10/2002 |
| WO | WO 2002/086083 | 10/2002 |
| WO | WO 2003/006632 | 1/2003 |
| WO | WO 2003/008583 | 1/2003 |
| WO | WO 2003/049755 | 6/2003 |
| WO | WO 2004/085418 | 10/2004 |
| WO | WO 2006/042237 | 4/2006 |
| WO | WO 2006/050172 | 5/2006 |
| WO | WO 2006/133396 | 12/2006 |
| WO | WO 2008/037080 | 4/2008 |
| WO | WO 2008/083174 | 7/2008 |
| WO | WO 2009/023566 | 2/2009 |
| WO | WO 2009/029342 | 3/2009 |
| WO | WO 2009/114110 | 9/2009 |
| WO | WO 2010/027423 | 3/2010 |
| WO | WO 2010/027827 | 3/2010 |
| WO | WO 2010/027828 | 3/2010 |
| WO | WO 2010/098788 | 9/2010 |
| WO | WO 2011/066342 | 6/2011 |
| WO | WO 2011/066389 | 6/2011 |
| WO | WO 2013/003112 | 2/2013 |
| WO | WO 2013/019906 | 2/2013 |
| WO | WO 2013/090552 | 6/2013 |
| WO | WO 2013/132044 | 9/2013 |
| WO | WO 2015/050663 | 4/2015 |
| WO | WO 2015/179654 | 11/2015 |
| WO | WO 2016/014148 | 1/2016 |

OTHER PUBLICATIONS

Gibbons et al, OncoImmunolgoy 1:1061-1072, published online Oct. 2012, IDS #416 filed on Aug. 2, 2016.*
Pardoll, Nature Review, 12:252-264, 2012.*
Acsadi et al., "Direct gene transfer and expression into rat heart in vivo," *New Biol.*, 3(1):71-81, Jan. 1991.
Adachi et al., "Enhanced and accelerated lymphoproliferation in Fas-null mice.," *Proc Natl Acad Sci U S A.*, 93(5):2131-2136, Mar. 5, 1996.
Adachi et al., "Aberrant transcription caused by the insertion of an early transposable element in an intron of the Fas antigen gene of Ipr mice," *Proc Natl Acad Sci U S A.*, 90(5):1756-1760, Mar. 1, 1993.
Agata et al., "Expression of the PD-1 antigen on the surface of stimulated mouse T and B lymphocytes," *Int Immunol.*, 8(5):765-772, May 1996.
Ahmadzadeh et al., "Tumor antigen-specific CD8 T cells infiltrating the tumor express high levels of PD-1 and are functionally impaired," *Blood*, 114(8):1537-1544, Epub May 7, 2009.
Ahonen et al., "Combined TLR and CD40 triggering induces potent CD8+ T cell expansion with variable dependence on type I IFN," *J Exp Med.*, 199(6):775-784, Epub Mar. 8, 2004.
Alderson et al., "Molecular and biological characterization of human 4-1BB and its ligand," *Eur J Immunol.*, 24(9):2219-2227, Sep. 1994.
Aldovini et al., "Humoral and cell-mediated immune responses to live recombinant BCG-HIV vaccines," *Nature*, 351(6326):479-482, Jun. 6, 1991.
Allie et al., "Programmed death 1 regulates development of central memory CD8 T cells after acute viral infection," *J Immunol.*, 186(11):6280-6286, Epub Apr. 27, 2011.
Ambrosini et al., "A novel anti-apoptosis gene, survivin, expressed in cancer and lymphoma," *Nat Med.*, 3(8):917-921, Aug. 1997.
Anderson, "Human gene therapy," *Science*, 256(5058):808-813, May 8, 1992.
Andorsky et al., "Programmed death ligand 1 is expressed by non-hodgkin lymphomas and inhibits the activity of tumor-associated T cells," *Clin Cancer Res.*, 17(13):4232-4244, Epub May 3, 2011.
Anikeeva et al., "Distinct role of lymphocyte function-associated antigen-1 in mediating effective cytolytic activity by cytotoxic T lymphocytes," *Proc Natl Acad Sci U S A.*, 102(18):6437-6442, Epub Apr. 25, 2005.
Ansari et al., "The programmed death-1 (PD-1) pathway regulates autoimmune diabetes in nonobese diabetic (NOD) mice," *J Exp Med.*, 198(1):63-69, Jul. 7, 2003.
Anukam et al., "Augmentation of antimicrobial metronidazole therapy of bacterial vaginosis with oral probiotic Lactobacillus rhamnosus GR-1 and Lactobacillus reuteri RC-14: randomized, double-blind, placebo controlled trial," *Microbes Infect.*, 8(6):1450-1454, Epub Mar. 29, 2006.
Attwood et al., "Genomics. The Babel of bioinformatics," *Science*, 290(5491):471-473, Oct. 20, 2000.
Azuma et al., "B7-H1 is a ubiquitous antiapoptotic receptor on cancer cells," *Blood.*, 111(7):3635-3643, Epub Jan. 25, 2008.
Baitsch et al., "Exhaustion of tumor-specific CD8+ T cells in metastases from melanoma patients," *J Clin Invest.*, 121(6):2350-2360, Epub May 9, 2011.
Bajorath et al., "Molecular modeling of CD28 and three-dimensional analysis of residue conservation in the CD28/CD152 family," *J Mol Graph Model.*, 15(2):135-9, 108-111, Apr. 1997.
Baldrick, "Pharmaceutical excipient development: the need for preclinical guidance," *Regul Toxicol Pharmacol.*, 32(2):210-218, Oct. 2000.
Banáth et al., "Residual gammaH2AX foci as an indication of lethal DNA lesions," *BMC Cancer.*, 10:4, Jan. 5, 2010.

(56) References Cited

OTHER PUBLICATIONS

Barber et al., "Restoring function in exhausted CD8 T cells during chronic viral infection," *Nature*, 439(7077):682-687, Epub Dec. 28, 2005.
BD PharmingenTM Technical Data Sheet, "Purified Rat Anti-Mouse Ly-6G (Gr-1) Monoclonal Antibody for Immunohistochemistry (IHC)" 1 page, 2003.
Benita et al., "Characterization of drug-loaded poly(d,l-lactide) microspheres " *J Pharm Sci.*, 73(12):1721-1724, Dec. 1984.
Benlalam et al., "Comprehensive analysis of the frequency of recognition of melanoma-associated antigen (MAA) by CD8 melanoma infiltrating lymphocytes (TIL) implications for immunotherapy," *Eur J Immunol.*, 31(7):2007-2015, Jul. 31, 2001.
Bennardo et al., "Alternative-NHEJ is a mechanistically distinct pathway of mammalian chromosome break repair," *PLoS Genet.*, 4(6):e1000110, Jun. 27, 2008.
Berman et al., "The Protein Data Bank," *Nucleic Acids Res.*, 28(1):235-242, Jan. 1, 2000.
Berrien-Elliott et al., "Durable adoptive immunotherapy for leukemia produced by manipulation of multiple regulatory pathways of CD8+ T-cell tolerance," *Cancer Res.*, 73(2):605-616, Epub Nov. 27, 2012.
Berthon et al., "In acute myeloid leukemia, B7-H1 (PD-L1) protection of blasts from cytotoxic T cells is induced by TLR ligands and interferon-gamma and can be reversed using MEK inhibitors," *Cancer Immunol Immunother.*, 59(12):1839-1849, Epub Sep. 4, 2010.
Betts et al., "Sensitive and viable identification of antigen-specific CD8+ T cells by a flow cytometric assay for degranulation," *J Immunol Methods.*, 281(1-2):65-78, Oct. 1, 2003.
Bird et al., "Single-chain antigen-binding 1988 proteins," *Science*, 242(4877):423-426, Oct. 21, 1988.
Blank et al., "Blockade of PD-L1 (B7-H1) augments human tumor-specific T cell responses in vitro," *Int J Cancer*, 119(2):317-327, Jul. 15, 2006.
Blank et al., "Interaction of PD-L1 on tumor cells with PD-1 on tumor-specific T cells as a mechanism of immune evasion: implications for tumor immunotherapy," *Cancer Immunol Immunother.*, 54(4):307-314, Epub Dec. 15, 2004.
Blank et al., "PD-L1/B7H-1 inhibits the effector phase of tumor rejection by T cell receptor (TCR) transgenic CD8+ T cells," *Cancer Res.*, 64(3):1140-1145, Feb. 1, 2004.
Blazar et al., "Infusion of anti-B7.1 (CD80) and anti-B7.2 (CD86) monoclonal antibodies inhibits murine graft-versus-host disease lethality in part via direct effects on CD4+ and CD8+ T cells," *J Immunol.*, 157(8):3250-3259, Oct. 15, 1996.
Block, "Medicated Applications," Remington's Pharmaceutical Sciences, 18th edition, Mack Publishing Company, Easton, PA, Chpt 87, pp. 1596-1614, 1990.
Bodine, "mTOR signaling and the molecular adaptation to resistance exercise," *Med Sci Sports Exerc.*, 38(11):1950-1957, Nov. 2006.
Boggio et al., "Interleukin 12-mediated prevention of spontaneous mammary adenocarcinomas in two lines of Her-2/neu transgenic mice," *J Exp Med.*, 188(3):589-596, Aug. 3, 1998.
Boise et al., "CD28 costimulation can promote T cell survival by enhancing the expression of Bcl-XL," *Immunity*, 3(1):87-98, Jul. 1995.
Boletta et al., "High efficient non-viral gene delivery to the rat kidney by novel polycationic vectors," *J Am Soc Nephrol.*, 7(9):1728, abstr A2409, Sep. 1, 1996.
Bona et al., "Immune response: Idiotype anti-idiotype network," *CRC Crit Rev Immunol.*, 33-81, Mar. 1981.
Bonfoco et al., "Inducible nonlymphoid expression of Fas ligand is responsible for superantigen-induced peripheral deletion of T cells," *Immunity*, 9(5):711-720, Nov. 1998.
Bonifaz et al., "Efficient targeting of protein antigen to the dendritic cell receptor DEC-205 in the steady state leads to antigen presentation on major histocompatibility complex class I products and peripheral CD8+ T cell tolerance," *J Exp Med.*, 196(12):1627-1638, Dec. 16, 2002.
Bonifaz et al., "In vivo targeting of antigens to maturing dendritic cells via the DEC-205 receptor improves T cell vaccination," *J Exp Med.*, 199(6):815-824, Mar. 15, 2004.
Bonni et al., "Cell survival promoted by the Ras-MAPK signaling pathway by transcription-dependent and -independent mechanisms," *Science*, 286(5443):1358-1362, Nov. 12, 1999.
Boon et al., "Human T cell responses against melanoma," *Annu Rev Immunol.*, 24:175-208, 2006.
Borson et al., "Brain-infiltrating cytolytic T lymphocytes specific for Theiler's virus recognize H2Db molecules complexed with a viral VP2 peptide lacking a consensus anchor residue," *J Virol.*, 71(7):5244-5250, Jul. 1997.
Bouillet and O'Reilly, "CD95, BIM and T cell homeostasis," *Nat Rev Immunol.*, 9(7):514-519, Jul. 2009.
Bowie et al, "Deciphering the message in protein sequences: tolerance to amino acid substitutions," *Science*, 247(4948):1306-1310, Mar. 16, 1990.
Brahmer et al., "Safety and activity of anti-PD-L1 antibody in patients with advanced cancer," *N Engl J Med.*, 366(26):2455-2465, Epub Jun. 2, 2012.
Braquet et al., "Effect of endothelin-1 on blood pressure and bronchopulmonary system of the guinea pig," *J Cardiovasc Pharmacol.*, 13 Suppl 5:S143-6; discussion S150, 1989.
Brinkmann et al., "FTY720: altered lymphocyte traffic results in allograft protection," *Transplantation.*, 72(5):764-769, Sep. 15, 2001.
Britton et al., "Leprosy," *Lancet*, 363(9416):1209-1219, Apr. 10, 2004.
Brooks, "Translational genomics: the challenge of developing cancer biomarkers," *Genome Res.*, 22(2):183-187, Feb. 2012.
Brown et al., "Blockade of programmed death-1 ligands on dendritic cells enhances T cell activation and cytokine production.," *J Immunol.*, 170(3):1257-1266, Feb. 1, 2003.
Brozovic et al., "Activation of mitogen-activated protein kinases by cisplatin and their role in cisplatin-resistance," *Cancer Lett.*, 251(1):1-16. Epub Nov. 27, 2006.
Bubenik, "Genetically engineered dendritic cell-based cancer vaccines (Review)," *Int J Oncol.*, 18(3):475-478, Mar. 2001.
Burmer et al, "Frequency and spectrum of c-Ki-ras mutations in human sporadic colon carcinoma, carcinomas arising in ulcerative colitis, and pancreatic adenocarcinoma," *Environ Health Perspect.*, 93:27-31, Jun. 1991.
Buskens et al, "Adenocarcinomas of the gastro-esophageal junction: A comparative study of the gastric cardia and the esophagus with respect to cyclooxygenase-2 expression," Digestive Disease Week Abstracts and Itinerary Planner, 2003, abstract No. 850.
Butte et al., "Interaction of human PD-L1 and B7-1," *Mol Immunol.*, 45(13):3567-3572, Epub Jun. 27, 2008.
Cairns et al., "Immortalization of multipotent growth-factor dependent hemopoietic progenitors from mice transgenic for GATA-1 driven SV40 tsA58 gene," *EMBO J.*, 13(19):4577-4586, Oct. 3, 1994.
Cannons et al., "4-1BB ligand induces cell division, sustains survival, and enhances effector function of CD4 and CD8 T cells with similar efficacy," *J Immunol.*, 167(3):1313-1324, Aug. 1, 2001.
Cao et al., "B7-H1 overexpression regulates epithelial-mesenchymal transition and accelerates carcinogenesis in skin," *Cancer Res.*, 71(4):1235-1243, Epub Dec. 15, 2010.
Carreno et al., "The B7 family of ligands and its receptors: new pathways for costimulation and inhibition of immune responses," *Annu Rev Immunol.*, 20:29-53, Epub Oct. 4, 2001.
Carter et al., "PD-1:PD-L inhibitory pathway affects both CD4(+) and CD8(+) T cells and is overcome by IL-2," *Eur J Immunol.*, 32(3):634-643, Mar. 2002.
Carter et al., "Humanization of an anti-p185HER2 antibody for human cancer therapy," *Proc Natl Acad Sci U S A.*, 89(10):4285-4289, May 15, 1992.
Chakrabarti et al., "Vaccinia virus expression vector: coexpression of beta-galactosidase provides visual screening of recombinant virus plaques," *Mol Cell Biol.*, 5(12):3403-3409, Dec. 1985.

(56) References Cited

OTHER PUBLICATIONS

Chambers et al., "Co-stimulation in T cell responses," *Curr Opin Immunol.*, 9(3):396-404, Jun. 1997.
Chan et al., "Autophosphorylation of the DNA-dependent protein kinase catalytic subunit is required for rejoining of DNA double-strand breaks," *Genes Dev.*, 16(18):2333-2338, Sep. 15, 2002.
Chapoval et al., "B7-H3: A costimulatory molecule for T cell activation and IFN-y production," *Nat Immunol.*, 2(3):269-274, Mar. 2001.
Charman, "Lipids, lipophilic drugs, and oral drug delivery-some emerging concepts," *J. Pharm. Sci.*, 89(8):967-978, Aug. 2000.
Chaurand et al., "Peptide and Protein Identification by Matrix-Assisted Laser Desorption Ionization (MALDI) and MALDI-Post-Source Decay Time-of-Flight Mass Spectrometry," *J Am Soc Mass Spectrom.*, 10(2):91-103, Feb. 1999.
Chen et al., "CD44-deficient mice exhibit enhanced hepatitis after concanavalin A injection: evidence for involvement of CD44 in activation-induced cell death," *J Immunol.*, 166(10):5889-5897, May 1, 2001.
Chen et al., "Costimulation of antitumor immunity by the B7 counterreceptor of the T lymphocyte molecules CD28 and CTLA-4," *Cell*, 71(7):1093-1102, Dec. 24, 1992.
Chen et al., "Tumor immunogenicity determines the effect of co-stimulation by B7 on T-cell mediated tumor immunity," *J Exp Med.*, 179(2):523-532, Feb. 1, 1994.
Chen, "Co-inhibitory molecules of the B7-CD28 family in the control of T-cell immunity," *Nat Rev Immunol.*, 4(5):336-347, May 2004.
Cheville et al., "Comparisons of outcome and prognostic features among histologic subtypes of renal cell carcinoma," *Am J Surg Pathol.*, 27(5):612-624, May 2003.
Choi et al., "Genomic Organization and expression Analysis of B7-H4, an Immune Inhibitory Molecule of the B7 Family," *J Immunol.*, 171(9):4650-4654, Nov. 1, 2003.
Cogoni et al. "Transgene silencing of the al-1 gene in vegetative cells of Neurospora is mediated by a cytoplasmic effector and does not depend on DNA-DNA interactions or DNA methylation ," *EMBO J.*, 15(12):3153-3163, Jun. 17, 1996.
Cogoni et al., "Gene silencing in Neurospora crassa requires a protein homologous to RNA-dependent RNA polymerase," *Nature*, 399(6732):166-169, May 13, 1999.
Cohen et al., "Lpr and gld: Single Gene Models of Systemic Autoimmunity and Lymphoproliferative Disease," *Annu Rev Immunol.*, 9:243-269, 1991.
Cole et al., "The EBV-hybridoma technique and its application to human lung cancer," *Monoclonal Antibodies and Cancer Therapy*, 27:77-96, Jan.-Feb. 1985.
Collins et al., "The B7 family of immune-regulatory ligands," *Genome Biol.*, 6(6):223, 7 pages, Epub May 31, 2005.
Collis et al., "The life and death of DNA-PK," *Oncogene.*, 24(6):949-961, Feb. 3, 2005.
Conacci-Sorrell et al., "Autoregulation E-cadherin expression by cadherin-cadherin interactions: the roles of beta-catenin signaling, Slug, and MAPK," *J Cell Biol.*, 163(4):847-857, Epub Nov. 17, 2003.
Cone et al., "High-efficiency gene transfer into mammalian cells: generation of helper-free recombinant retrovirus with broad mammalian host range," *Proc Natl Acad Sci U S A.*, 81(20):6349-6353, Oct. 1984.
Connolly, "Analytical molecular surface calculation," *J Appl Crystallogr.*, 16(5):548-558, Oct. 1, 1983.
Corpet, "Multiple sequence alignment with hierarchical clustering," *Nucleic Acids Res.*, 6(22):10881-10890, Nov. 25, 1988.
Cote et al., "Generation of human monoclonal antibodies reactive with cellular antigens," *Proc Natl Acad Sci U S A.*, 80(7):2026-2030, Apr. 1983.
Coyle et al., "The expanding B7 superfamily: increasing complexity in costimulatory signals regulating T cell function," *Nat Immunol.*, 2(3):203-209, Mar. 2001.

Crispe et al., "The liver as a site of T-cell apoptosis: graveyard, or killing field?" *Immunol Rev.*, 174:47-62, Apr. 2000.
Crispe, "Hepatic T cells and liver tolerance," *Nat Rev Immunol.*, 3(1):51-62, Jan. 2003.
Cristiano et al., "Molecular conjugates: a targeted gene delivery vector for molecular medicine," *J Mol Med (Berl)*. 73(10):479-486, Oct. 1995.
Crystal, "Gene therapy strategies for pulmonary disease" *Am J Med.*, 92(suppl 6A):44S-52S, Jun. 22, 1992.
Curiel et al., "Blockade of B7-H1 improves myeloid dendritic cell-mediated antitumor immunity," *Nat Med.*, 9(5):562-567, Epub Apr. 21, 2003.
Dao et al., "Involvement of CD1 in peripheral deletion of T lymphocytes is independent of NK T cells," *J Immunol.*, 166(5):3090-3097, Mar. 1, 2001.
Database EM-MUS [Online]EMBL; Accession No. AF142780.1 (version 1), Jun. 1, 1999, 2 pages.
Datta et al., "Akt phosphorylation of BAD couples survival signals to the cell-intrinsic death machinery," *Cell.*, 91(2):231-241, Oct. 17, 1997.
Davidson et al., "Phenotypic, functional, and molecular genetic comparisons of the abnormal lymphoid cells of C3H-Ipr/Ipr and C3H-gld/gld mice," *J Immunol.*, 136(11):4075-4084, Jun. 1, 1986.
Davidson et al., "Small Molecules, Inhibitors of DNA-PK, Targeting DNA Repair, and Beyond," *Front Pharmacol.*, vol. 4, Article 5, pp. 1-7, Jan. 31, 2013.
de StGroth et al., "Production of monoclonal antibodies: strategy and tactics," *J Immunol Methods.*, 35(1-2):1-21, 1980.
Debs et al., "Lung-specific delivery of cytokines induces sustained pulmonary and systemic immunomodulation in rats," *J Immunol.*, 140(10):3482-3488, May 15, 1988.
del Peso et al., "Interleukin-3-induced phosphorylation of BAD through the protein kinase Akt," *Science*, 278(5338):687-689, Oct. 24, 1997.
Dheda et al., "Lung remodeling in tuberculosis," *J Infect Dis.*, 192(7):1201-1209, Epub Aug. 29, 2005.
Diehl et al., "In vivo triggering through 4-1BB enables Th-independent priming of CTL in the presence of an intact CD28 costimulatory pathway," *J Immunol.*, 168(8):3755-3762, Apr. 15, 2002.
Ding et al., "Release of reactive nitrogen intermediates and reactive oxygen intermediates from mouse peritoneal macrophages. Comparison of activating cytokines and evidence for independent production," *J Immunol.*, 141(7):2407-2412, Oct. 1, 1988.
Dini, "Recognizing death: liver phagocytosis of apoptotic cells," *Eur J Histochem.*, 44(3):217-227, 2000.
Doering et al., "Network analysis reveals centrally connected genes and pathways involved in CD8+ T cell exhaustion versus memory," *Immunity*, 37(6):1130-1144, Epub Nov. 15, 2012.
Dong and Chen, "B7-H1 pathway and its role in the evasion of tumor immunity," *J Mol Med (Berl).*, 81(5):281-287, Epub Apr. 30, 2003.
Dong et al., "B7-H1 determines accumulation and deletion of intrahepatic CD8(+) T lymphocytes," *Immunity.*, 20(3):327-336, Mar. 2004.
Dong et al., "B7-H1 pathway and its role in the evasion of tumor immunity" *J Mol Med (Berl).*, 81(5):281-287, Epub Apr. 30, 2003.
Dong et al., "B7-H1, a third member of the B7 family, co-stimulates T-cell proliferation and interleukin-10 secretion," *Nat Med.*, 5(12):1365-1369, Dec. 1999.
Dong et al., "Costimulating aberrant T cell responses by B7-H1 autoantibodies in rheumatoid arthritis," *J Clin Invest.*, 111(3):363-370, Feb. 2003.
Dong et al., "Immune regulation by novel costimulatory molecules," *Immunol Res.*, 28(1):39-48, 2003.
Dong et al., "Immunoregulatory role of B7-H1 in chronicity of inflammatory responses," *Cell Mol Immunol.*, 3(3):179-187, Jun. 2006.
Dong et al., "Tumor-associated B7-H1 promotes T-cell apoptosis: a potential mechanism of immune evasion," *Nat Med.*, 8(8):793-800, Epub Jun. 24, 2002.

(56) References Cited

OTHER PUBLICATIONS

Dragoi et al., "DNA-PKcs, but not TLR9, is required for activation of Akt by CpG-DNA," *EMBO J.*, 24(4):779-789, Epub Jan. 27, 2005.
Dronca et al., "Soluble PD-L1 (sPD-L1) is associated with decreased survival in metastatic melanoma ," Society for Melanoma Research 2015 Congress, San Francisco, CA, Nov. 18-21, 2015 [abstract].
Dudler et al., "Gene transfer of programmed death Ligand-I.Ig prolongs cardiac allograft survival," Transplantation, 82(12):1733-1737, Dec. 27, 2006.
Dunussi-Joannopoulos et al., "Gene therapy with B7.1 and GM-CSF vaccines in a murine AML model," *J Pediatr Hematol Oncol.*, 19(6):536-540, Nov.-Dec. 1997.
Duraiswamy et al., "Replenish the source within: Rescuing tumor-infiltrating lymphocytes by double checkpoint blockade," *Oncoimmunology.*, 2(10):e25912. Epub Aug. 2, 2013.
Ehl et al., "Different susceptibility of cytotoxic T cells to CD95 (Fas/Apo-1) ligand-mediated cell death after activation in vitro versus in vivo," *J Immunol.*, 156(7):2357-2360, Apr. 1, 1996.
Elliott et al., "Mitoxantrone in combination with an inhibitor of DNA-dependent protein kinase: a potential therapy for high risk B-cell chronic lymphocytic leukaemia," *Br J Haematol.*, 152(1):61-71, Epub Nov. 18, 2010.
EMBL-EBI Accession No. AF 142780.2 "Mus musculus butyrophilin-like protein (Btdc) mRNA, complete cds," created Jun. 1, 1999, 2 pages.
EMBL-EBI Accession No. Q9WUL5, "Programmed cell death 1 ligand 2," Nov. 1, 1999, 5 pages.
Engh et al., "Accurate bond and angle parameters for X-ray protein structure refinement," *Acta Cryst.*, A47(4):392-400, Jul. 1, 1991.
European Examination Report for Bristol-Myers Squibb Co., App. No. 07 023 993.4-1521, dated May 19, 2010, 6 pages.
European Search Report for Application No. EP 02802551, 3 pages, completed Oct. 14, 2004, 4 pages.
Falkner et al., "pUV I: a new vaccinia virus insertion and expression vector," *Nucleic Acids Res.*, 15(17):7192, Sep. 11, 1987.
Farley et al., "p38 mitogen-activated protein kinase mediates the Fas-induced mitochondrial death pathway in CD8+ T cells," *Mol Cell Biol.*, 26(6):2118-2129, Mar. 2006.
Fechteler et al., "Prediction of protein three-dimensional structures in insertion and deletion regions: a procedure for searching data bases of representative protein fragments using geometric scoring criteria," *J Mol Biol.*, 253(1):114-131, Oct. 13, 1995.
Feng et al., "Identification of a PKB/Akt hydrophobic motif Ser-473 kinase as DNA-dependent protein kinase," *J Biol Chem.*, 279(39):41189-41196, Epub Jul. 15, 2004.
Figlin et al., "Treatment of metastatic renal cell carcinoma with nephrectomy, interleukin-2 and cytokine-primed or CD8(+) selected tumor infiltrating lymphocytes from primary tumor," *J Urol.*, 158(3 Pt 1):740-745, Sep. 1997.
Finck et al., "Treatment of Murine Lupus with CTLA4Ig," *Science*, 265(5176):1225-1227, Aug. 26, 1994.
Fire et al., "Potent and specific genetic interference by double-stranded RNA in Caenorhabditis elegans," *Nature*, 391(6669):806-811, Feb. 19, 1998.
Fleming et al., Selective expression of Ly-6G on myeloid lineage cells in mouse bone marrow. RB6-8C5 mAb to granulocyte-differentiation antigen (Gr-1) detects members of the Ly-6 family, *J Immunol.*, 151(5):2399-2408, Sep. 1, 1993.
Foell et al., "CD137 costimulatory T cell receptor engagement reverses acute disease in lupus-prone NZB x NZW F1 mice," *J Clin Invest.*, 111(10):1505-1518, May 2003.
Foell et al., "CD137-Mediated T Cell Co-Stimulation Terminates Existing Autoimmune Disease in SLE-Prone NZB/NZW F1 Mice," *Ann N Y Acad Sci.*, 987:230-235, Apr. 2003.
Fortugno et al., "Survivin exists in immunochemically distinct subcellular pools and is involved in spindle microtubule function," *J Cell Sci.*, 115(Pt 3):575-585, Feb. 1, 2002.

Frank et al., "An outcome prediction model for patients with clear cell renal cell carcinoma treated with radical nephrectomy based on tumor stage, size, grade and necrosis: the SSIGN score," *J Urol.*, 168(6):2395-2400, Dec. 2002.
Freeman et al., "B7, a new member of the Ig superfamily with unique expression on activated and neoplastic B cells," *J Immunol.*, 143(8):2714-2722, Oct. 15, 1989.
Freeman et al., "Cloning of B7-2: a CTLA-4 counter-receptor that co stimulates human T cell proliferation," *Science*, 262(5135):909-911, Nov. 5, 1993.
Freeman et al., "Engagement of the PD-1 Immunoinhibitory receptor by a novel B7 family member leads to negative regulation of lymphocyte activation," *J Exp Med.*, 192(7):1027-1034, Oct. 2, 2000.
Freeman et al., "Structure, expression, and T cell proliferation costimulatory activity of the murine homologue of the human B lymphocyte activation antigen B7," *J Exp Med.*, 174(3):625-631, Sep. 1, 1991.
Friedmann et al., "Interaction of the epidermal growth factor receptor and the DNA-dependent protein kinase pathway following gefitinib treatment," *Mol Cancer Ther.*, 5(2):209-218, Feb. 2006.
Frigola et al., "Identification of a soluble form of B7-H1 that retains immunosuppressive activity and is associated with aggressive renal cell carcinoma," *Clin Cancer Res.*, 17(7):1915-1923, Epub Feb. 25, 2011.
Fuerst et al., "Transfer of the inducible lac repressor/operator system from *Escherichia coli* to a vaccinia expression vector," *Proc Natl Acad Sci U S A.*, 86(8):2549-2553, Apr. 1989.
Fyfe et al., "Results of treatment of 255 patients with metastatic renal cell carcinoma who received high-dose recombinant interleukin-2 therapy," *J Clin Oncol.*, 13(3):688-696, Mar. 1995.
GenBank Accession No. AAC51660 "apoptosis inhibitor survivin [*Homo sapiens*]," Sep. 2, 2004, 2 pages.
GenBank Accession No. AAP37283, "immune costimulatory protein B7-H4 [*Homo sapiens*]," Jun. 1, 2003, 1 page.
GenBank Accession No. AK001872.1,"*Homo sapiens* cDNA FLJ11010 fis, clone PLACE1003145," Feb. 22, 2000, 2 pages.
GenBank Accession No. AL162253, "Human DNA sequence from clone RP11-574F11 on chromosome 9 contains the gene for B7-H1 protein (PD-LI), the gene for programmed death ligand 2 (PDL2) (PDCD1L2) and a novel gene, complete sequence" Feb. 24, 2008, 35 pages.
GenBank Accession No. AY280972, "*Homo sapiens* immune costimulatory protein B7-H4 mRNA, complete cds," Jun. 1, 2003, 1 page.
GenBank Accession No. NM_005191.3 (GI No. 113722122), "*Homo sapiens* CD80 molecule (CD80), mRNA," Jun. 15, 2013, 5 pages.
GenBank Accession No. NP_005182.1 (GI No. 4885123), "T-lymphocyte activation antigen CD80 precursor [*Homo sapiens*]," Jun. 15, 2013, 3 pages.
GenBank Accession No. U75285 "*Homo sapiens* apoptosis inhibitor survivin gene, complete cds," Sep. 2, 2004, 5 pages.
GenBank® Accession No. AAF25807 (GI No. 6708119), "B7-H1 [*Homo sapiens*]," Jan. 18, 2000, 2 pages.
GenBank® Accession No. AAH74740.1, GI No. 49902307, "Programmed cell death 1 [*Homo sapiens*]," Jul. 15, 2006, 2 pages.
GenBank® Accession No. AAX29153.1, GI No. 60652917, "integrin alpha L, partial [synthetic construct]," Mar. 29, 2005, 2 pages.
GenBank® Accession No. AF177937 (GI No. 6708118), "*Homo sapiens* B7-H1 mRNA, complete cds," Jan. 18, 2000, 1 page.
GenBank® Accession No. BC008777.2, GI No. 33870544, "*Homo sapiens* integrin, alpha L (antigen CD11A (p180), lymphocyte function-associated antigen 1; alpha polypeptide), mRNA (cDNA clone MGC:1714 IMAGE:3142951), complete cds," Jul. 28, 2005, 4 pages.
GenBank® Accession No. BC074740.2, GI No. 50960296, "*Homo sapiens* programmed cell death 1, mRNA (cDNA clone MGC:103817 IMAGE:30915198), complete cds," Jul. 15, 2006, 3 pages.
Gerdes et al. "Cell cycle analysis of a cell proliferation-associated human nuclear antigen defined by the monoclonal antibody Ki-67," *J Immunol.*, 133(4):1710-1715, Oct. 1984.

(56) References Cited

OTHER PUBLICATIONS

Gerstmayer et al., "Costimulation of T cell proliferation by a chimeric B7-2 antibody fusion protein specifically targeted to cells expressing the erbB2 proto-oncogene," *J Immunol.*, 158(10):4584-4590, May 15, 1997.

Gerstmayer et al., "Costimulation of T-cell proliferation by a chimeric B7 antibody fusion protein," *Cancer Immunol Immunother.*, 45(3-4):156-158, Nov.-Dec. 1997.

Gevaert et al., "Protein identification based on matrix assisted laser desorption/ionization-post source decay-mass spectrometry," *Electrophoresis*, 22(9):1645-1651, May 2001.

Ghebeh et al., "Doxorubicin downregulates cell surface B7-H1 expression and upregulates its nuclear expression in breast cancer cells: role of B7-H1 as an anti-apoptotic molecule," *Breast Cancer Res.*, 12(4):R48, Epub Jul. 13, 2010.

Ghebeh et al., "The B7-H1 (PD-L1) T lymphocyte-inhibitory molecule is expressed in breast cancer patients with infiltrating ductal carcinoma: correlation with important high risk prognostic factors," *Neoplasia*, 8(3):190-198, Mar. 2006.

Gibbons et al., "B7-H1 limits the entry of effector CD8(+) T cells to the memory pool by upregulating Bim," Oncoimmunology, 1(7):1061-1073, Oct. 1, 2012.

Gillings et al., "Apoptosis and autophagy: BIM as a mediator of tumour cell death in response to oncogene-targeted therapeutics," *FEBS J.*, 276(21):6050-6062, Epub Sep. 29, 2009.

Gimmi et al., "B-cell surface antigen B7 provides a costimulatory signal that induces T cells to proliferate and secrete interleukin 2," *Proc Natl Acad Sci U S A.*, 88(9):3671-3675, May 1, 1991.

Goodwin et al., "Molecular cloning and expression of the type 1 and type 2 murine receptors for tumor necrosis factor," *Mol Cell Biol.*, 11(6):3020-3026, Jun. 1991.

Goodwin et al., "Molecular cloning of a ligand for the inducible T cell gene 4-1BB: a member of an emerging family of cytokines with homology to tumor necrosis factor," *Eur J Immunol.*, 23(10):2631-2641, Oct. 1993.

Green et al., "Activation-induced cell death in T cells," *Immunol Rev.*, 193:70-81, Jun. 2003.

Green et al., "Antigen-specific human monoclonal antibodies from mice engineered with human Ig heavy and light chain YACs," *Nat Genet.*, 7(1):13-21, May 1994.

Greenwald et al., "The B7 family revisited," *Annu Rev Immunol.*, 23:515-548, 2005.

Grivennikov et al. "Immunity, inflammation, and cancer," *Cell.*, 140(6):883-899, Mar. 19, 2010.

Guatelli et al., "Isothermal, in vitro amplification of nucleic acids by a multi enzyme reaction modeled after retroviral replication," *Proc Natl Acad Sci U S A.*, 87(5):1874-1878, Mar. 1990.

Guinn et al., "4-1BBL cooperates with B7-1 and B7-2 in converting a B cell lymphoma cell line into a long-lasting antitumor vaccine," *J Immunol.*, 162(8):5003-5010, Apr. 15, 1999.

Gunn et al., "Correct end use during end joining of multiple chromosomal double strand breaks is influenced by repair protein RAD50, DNA-dependent protein kinase DNA-PKcs, and transcription context," *J Biol Chem.*, 286(49):42470-42482, Epub Oct. 24, 2011.

Guo et al., "A novel fusion protein of IP1 O-scFv retains antibody specificity and chemokine function," *Biochem Biophvs Res Commun.*, 320(2):506-513, Jul. 23, 2004.

Haendeler et al., "Nitric Oxide and Apoptosis," *Vitam Horm.*, 57:49-77, 1999.

Hansen et al., "Monoclonal antibodies identifying a novel T-cell antigen and Ia antigens of human lymphocytes," *Immunogenetics*, 10(1-4):247-260, Feb. 1, 1980.

Harrington et al., "Differentiating between memory and effector CD8 T cells by altered expression of cell surface O-glycans," *J Exp Med.*, 191(7):1241-1246, Apr. 3, 2000.

Hatzoglou et al., "Hepatic gene transfer in animals using retroviruses containing the promoter from the gene for phosphoenolpyruvate carboxykinase" *J Biol Chem.*, 265(28):17285-17293, Oct. 5, 1990.

Hawiger et al., "Dendritic cells induce peripheral T cell unresponsiveness under steady state conditions in vivo," *J Exp Med.*, 194(6):769-779, Sep. 17, 2001.

Hayakawa et al., "Inhibition of BAD phosphorylation either at serine 112 via extracellular signal-regulated protein kinase cascade or at serine 136 via Akt cascade sensitizes human ovarian cancer cells to cisplatin," *Cancer Res.*, 60(21):5988-5994, Nov. 1, 2000.

He et al., "Identification of a novel splice variant of human PD-L1 mRNA encoding an isoform-lacking Igv-like domain," *Acta Pharmacol Sin.*, 26(4):462-468, Apr. 2005.

Hellstrom et al., "T cell immunity to tumor antigens," *Crit Rev Immunol.*, 18(1-2):1-6, 1998.

Henry et al., "Cloning, structural analysis, and mapping of the B30 and B7 multigenic families to the major histocompatibility complex (MHC) and other chromosomal regions," *Immunogenetics*, 46(5):383-395, 1997.

Henry et al., "Structure and evolution of the extended B7 family," *Immunol Today*, 20(6):285-288, Jun. 1999.

Hentikoff, "Amino acid substitution matrices from protein blocks," *Proc Natl Acad Sci U S A.*, 89(22):10915-10919, Nov. 15, 1992.

Hestdal et al., "Characterization and regulation of RB6-8C5 antigen expression on murine bone marrow cells," *J Immunol.*, 147(1):22-28, Jul. 1, 1991.

Hildeman et al., "Activated T cell death in vivo mediated by proapoptotic bcl-2 family member bim," *Immunity*, 16(6):759-767, Jun. 2002.

Hirano et al., "Blockade of B7-H1 and PD-1 by monoclonal antibodies potentiates cancer therapeutic immunity," *Cancer Res.*, 65(3):1089-1096, Feb. 1, 2005.

Hiroishi et al., "Interferon-alpha gene therapy in combination with CDS0 transduction reduces tumorigenicity and growth of established tumor in poorly immunogenic tumor models," *Gene Ther.*, 6(12):1988-1994, Dec. 1999.

Hochman et al., "An active antibody fragment (Fv) composed of the variable portions of heavy and light chains," *Biochemistry*, 12(6):1130-1135, Mar. 13, 1973.

Hock et al., "Retrovirus-mediated transfer and expression of drug resistance genes in human haematopoietic progenitor cells," *Nature*, 320:275-277, 1986.

Hoffman, "T Cells in the Pathogenesis of Systemic Lupus Erythematosus," *Front Biosci.*, 6:D1369-D1378, Oct. 1, 2001.

Hoiseth et al., "Aromatic-dependent Salmonella typhimurium are non-virulent and effective as live vaccines," *Nature*, 291(5812):238-239, May 21, 1981.

Hollinger et al., "Diabodies": small bivalent and bispecific antibody fragments, *Proc Natl Acad Sci U S A.*, 90(14):6444-6448, Jul. 15, 1993.

Holt et al., "Domain antibodies: proteins for therapy," *Trends Biotechnol.*, 21(11):484-490, Nov. 2003.

Hori et al., "B7-H1-induced apoptosis as a mechanism of immune privilege of corneal allografts," *J Immunol.*, 177(9):5928-5935, Nov. 1, 2006.

Huai et al., "Inducible gene expression with the Tet-on system in CD4+ T cells and thymocytes of mice," *Genesis*, 45(7):427-431, Jul. 2007.

Huang et al., "The liver eliminates T cells undergoing antigen-triggered apoptosis in vivo," *Immunity*, 1(9):741-749, Dec. 31, 1994.

Huang, "Structural chemistry and therapeutic intervention of protein-protein interactions in immune response, human immunodeficiency virus entry, and apoptosis" *Pharmacol Ther.*, 86(3):201-215, Jun. 2000.

Hubbard et al., "Anti-neutrophil-elastase defenses of the lower respiratory tract in alpha 1-antitrypsin deficiency directly augmented with an aerosol of alpha I-antitrypsin," *Ann Intern Med.*, 111(3):206-212, Aug. 1, 1989.

Hunter, "Diabetes in pregnancy," Effective Care in Pregnancy and Childbirth, Chalmers et al. (eds.), Oxford University Press, vol. 1, pp. 578-593, 1989.

Huse et al., "Generation of a large combinatorial library of the immunoglobulin repertoire in phage lambda," *Science*, 246(4935):1275-1281, Dec. 8, 1989.

(56) References Cited

OTHER PUBLICATIONS

Huston et al., "Protein engineering of antibody binding sites: recovery of specific activity in an anti-digoxin single-chain Fv analogue produced in Escherichia coli," Proc Natl Acad Sci U S A., 85(16):5879-5883, Aug. 1988.
Hutloff et al., "ICOS is an inducible T-cell co-stimulator structurally and functionally related to CD28," Nature, 397(6716):263-266, Jan. 21, 1999.
Hyrup et al., "Peptide nucleic acids (PNA): synthesis, properties and potential applications," Bioorg Med Chem., 4(1):5-23, Jan. 31, 1996.
Ichikawa and Chen, "Role of B7-H1 and B7-H4 molecules in down-regulating effector phase of T-cell immunity: novel cancer escaping mechanisms," Front Biosci., 10:2856-2860, Sep. 1, 2005.
Ikemizu et al., "Structure and dimerization of a soluble form of B7-1," Immunity, 12(1):51-60, Jan. 2000.
Ikonomidis, "Delivery of a viral antigen to the class I processing and presentation pathway by Listeria monocytogenes," J Exp Med., 180(6):2209-2218, Dec. 1, 1994.
Inman et al. "PD-L1 (B7-H1) expression by urothelial carcinoma of the bladder and BCG-induced granulomata: associations with localized stage progression," Cancer, 109(8):1499-1505, Apr. 15, 2007.
Inman et al., "Questionable relevance of gamma delta T lymphocytes in renal cell carcinoma," J Immunol., 180(5):3578-3584, Mar. 1, 2008.
International Preliminary Report on Patentability in International Application No. PCT/US2003/22029, dated Mar. 25, 2005, 5 pages.
International Preliminary Report on Patentability in International Application No. PCT/US2007/060133, dated Oct. 30, 2008, 8 pages.
International Preliminary Report on Patentability in International application No. PCT/US2007/60150, dated Sep. 18, 2008, 5 pages.
International Preliminary Report on Patentability in International Application No. PCT/US2007/066970, dated Oct. 30, 2008, 8 pages.
International Preliminary Report on Patentability in International Application PCT/US2014/053870, dated Apr. 5, 2016, 7 pages.
International Preliminary Report on Patentability re PCT/US2009/035495, dated Sep. 10, 2010, 5 pages.
International Search Report and Written Opinion for PCT/US2014/053870, dated Feb. 4, 2015, 12 pages.
International Search Report and Written Opinion for PCT/US2015/032016, dated Aug. 26, 2015, 17 pages.
International Search Report and Written Opinion for PCT/US2015/031993, dated Sep. 29, 2015, 18 pages.
International Search Report and Written Opinion in International Application No. PCT/US2007/60133, dated Sep. 25, 2008, 13 pages.
International Search Report and Written Opinion in International Application No. PCT/US2007/60150, dated Jul. 7, 2008, 8 pages.
International Search Report and Written Opinion in International Application No. PCT/US2007/066970, dated Oct. 5, 2007, 13 pages.
International Search Report and Written Opinion of the International Search Authority re PCT/US2009/035495, dated Oct. 6, 2009, 7 pages.
International Search Report for PCT/US2002/32364, dated Mar. 25, 2003, 2 pages.
International Search Report in International Application No. PCT/US2003/22029, dated Dec. 2, 2004, 5 pages.
Invitation to Pay for PCT/US2014/053870, dated Nov. 19, 2014, 3 pages.
Ishida et al., "Differential expression of PD-LI and PD-L2, ligands for an inhibitory receptor PD-I, in the cells of lymphohematopoietic tissues," Immunol Lett., 84(1):57-62, Oct. 21, 2002.
Ishida et al., "Induced expression of PD-I, a novel member of the immunoglobulin gene superfamily, upon programmed cell death," EMBO J., 11(11):3887-3895, Nov. 1992.

Iwai et al., "Involvement of PD-L1 on tumor cells in the escape from host immune system and tumor immunotherapy by PD-L1 blockade," Proc Natl Acad Sci U S A., 99(19):12293-12297, Epub Sep. 6, 2002.
Iwai et al., "PD-1 inhibits antiviral immunity at the effector phase in the liver," J Exp Med., 198(1):39-50, Jul. 7, 2003.
Jacinto et al., "SIN1/MIP1 maintains rictor-mTOR complex integrity and regulates Akt phosphorylation and substrate specificity," Cell, 127(1):125-137, Epub. Sep. 7, 2006.
Jacobson et al., "Unique site of IgG2a and rheumatoid factor production in MRL/Ipr mice," Immunol Rev., 156:103-110, Apr. 1997.
Jayaraman, "Flow cytometric determination of mitochondrial membrane potential changes during apoptosis of T lymphocytic and pancreatic beta cell lines: comparison of tetramethylrhodamineethylester (TMRE), chloromethyl-X-rosamine (H2-CMX-Ros) and MitoTracker Red 580 (MTR580)," J Immunol Methods., 306(1-2):68-79, Epub Sep. 29, 2005.
Jeannin et al., "Soluble CD86 is a costimulatory molecule for human T lymphocytes," Immunity, 13(3):303-312, Sep. 2000.
Jemal et al., "Cancer Statistics, 2005," CA Cancer J Clin, 55(1):10-30, Jan.-Feb. 2005.
Jerne, "Towards a network theory of the immune system," Ann Immunol (Paris). 125C(1-2):373-389, Jan. 1974.
Jiang et al., "Genome-wide association study for biomarker identification of Rapamycin and Everolimus using a lymphoblastoid cell line system," Front Genet., 4:166, Aug. 30, 2013.
Johnston et al., "Biolistic transformation of animal tissue," In Vitro Cell Dev Biol Anim., 27P: 11-14 (1991).
Jones et al., "Replacing the complementarity-determining regions in a human antibody with those from a mouse," Nature, 321(6069):522-525, May 29-Jun. 4, 1986.
Kabat et al., Sequences of Proteins of Immunological Interest, Fifth Edition, U.S. Department of Health and Human Services, NIH Publication No. 91-3242, Table of Contents, 20 pages, 1991.
Kaleko et al., "Persistent gene expression after retroviral gene transfer into liver cells in vivo," Hum Gene Ther., 2(1):27-32, Spring 1991.
Kaliyaperumal et al., "Antigen-specific therapy of murine lupus nephritis using nucleosomal peptides: tolerance spreading impairs pathogenic function of autoimmune T and B cells," J Immunol., 162(10):5775-5783, May 15, 1999.
Kalled et al., "Anti-CD40 ligand antibody treatment of SNF1 mice with established nephritis: preservation of kidney function," J Immunol., 160(5):2158-2165, Mar. 1, 1998.
Kanai et al., "Blockade of B7-H1 suppresses the development of chronic intestinal inflammation," J Immunol., 171(8):4156-4163, Oct. 15, 2003.
Kaneko et al., "Augmentation of Va14 NKT cell-mediated cytotoxicity by interleukin 4 in an autocrine mechanism resulting in the development of concanavalin A-induced hepatitis," J Exp Med., 191(1):105-114, Jan. 3, 2000.
Karakhanova et al., "ERK/p38 MAP-kinases and PI3K are involved in the differential regulation of B7-H1 expression in DC subsets," Eur J Immunol., 40(1):254-266, Jan. 2010.
Kataoka et al., "Flow cytometric analysis of phosphorylated histone H2AX following exposure to ionizing radiation in human microvascular endothelial cells," J Radiat Res., 47(3-4):245-257, Epub Sep. 2006.
Katou et al., "Differing phenotypes between intraepithelial and stromal lymphocytes in early-stage tongue cancer," Cancer Res., 67(23):11195-11201, Dec. 1, 2007.
Kaufman et al., "A phase I trial of intra lesional RV-B7.1 vaccine in the treatment of malignant melanoma," Hum Gene Ther., 11(7):1065-1082, May 1, 2000.
Kawabe et al., "Programmed cell death and extrathymic reduction of Vβ8+ CD4+ T cells in mice tolerant to Staphylococcus aureus enterotoxin B," Nature, 349(6306):245-248, Jan. 17, 1991.
Keir et al., "PD-1 and its ligands in tolerance and immunity," Annu Rev Immunol., 26:677-704, 2008.
Kelley et al., "Cytokines in the Pathogenesis of Systemic Lupus Erythematosus," Semin Nephrol., 19(1):57-66, Jan. 1999.

(56) References Cited

OTHER PUBLICATIONS

Kennerdell et al., "Use of dsRNA-mediated genetic interference to demonstrate that frizzled and frizzled 2 act in the wingless pathway," *Cell*, 95(7):1017-1026, Dec. 23, 1998.
Kharbanda et al., "Translocation of SAPK/JNK to mitochondria and interaction with Bcl-x(L) in response to DNA damage," *J Biol Chem.*, 275(1):322-327, Jan. 7, 2000.
Kiessling et al., "High-throughput mutation profiling of CTCL samples reveals KRAS and NRAS mutations sensitizing tumors toward inhibition of the RAS/RAF/MEK signaling cascade," *Blood*, 117(8):2433-2440, Epub Jan. 5, 2011.
Kim et al., "Features of responding T cells in cancer and chronic infection," *Curr Opin Immunol.*, 22(2):223-230, Epub Mar. 6, 2010.
Kim et al., "Therapeutic potential of 4-1BB (CD137) as a regulator for effector CD8(+) T cells," *J Hematother Stem Cell Res.*, 10(4):441-449, Aug. 2001.
Köhler et al., "Continuous cultures of fused cells secreting antibody of predefined specificity," *Nature*, 256(5517):495-497, Aug. 7, 1975.
Kohn et al. "Gene therapy for genetic diseases," *Cancer Invest.*, 7(2):179-192, 1989.
Konieczny et al., "The combination of IgM subunits and proteolytic IgG fragment by controlled formation of interchain disulphides," *Haematologia (Budap)*. 14(1):95-99, 1981.
Korkola et al, "Gene expression-based classification of nonseminomatous male germ cell tumors," *Oncogene*, 24(32):5101-5107, Jul. 28, 2005.
Kosari et al, "Clear cell renal cell carcinoma: gene expression analyses identify a potential signature for tumor aggressiveness," *Clin Cancer Res.*, 11(14):5128-5139, Jul. 15, 2005.
Kozbor et al. "The production of monoclonal antibodies from human lymphocytes," *Immunology Today*, 4(3):72-79, Mar. 1, 1983.
Krempski et al., "Tumor-infiltrating programmed death receptor-1+ dendritic cells mediate immune suppression in ovarian cancer," *J Immunol.*, 186(12):6905-6913, Epub May 6, 2011.
Kruege et al., "The role of CD95 in the regulation of peripheral T-cell apoptosis," *Immunol Rev.*, 193:58-69, Jun. 2003.
Krummel et al., "CTLA-4 engagement inhibits IL-2 accumulation and cell cycle progression upon activation of resting T cells," *J Exp Med.*, 183(6):2533-2540, Jun. 1, 1996.
Kuiper et al., "B7.1 and Cytokines: Synergy in cancer gene therapy," *Adv Exp Med Biol.*, 465:381-390, 2000.
Kusmartsev et al., "Gr-1+ myeloid cell derived from tumor-bearing mice inhibit primary T cell activation induced through CD3/CD28 costimulation," *J Immunol.*, 165(2):779-785, Jul. 15, 2000.
Kwon et al., "4-1BB: Still in the Midst of Darkness," *Mol Cells.*, 10(2):119-126, Apr. 30, 2000.
LaBaer, "So, you want to look for biomarkers (introduction to the special biomarkers issue)," *J Proteome Res.*, 4(4):1053-1059, Jul.-Aug. 2005.
Larrubia et al., "Bim-mediated apoptosis and PD-1/PD-L1 pathway impair reactivity of PD1(+)/CD127(−) HCV-specific CD8(+) cells targeting the virus in chronic hepatitis C virus infection," *Cell Immunol.*, 269(2):104-114, Epub Mar. 17, 2011.
Latchman et al., "PD-L2 is a second ligand for PD-1 and inhibits T cell activation," *Nat Immunol.*, 2(3):261-268, Mar. 2001.
Lawson et al., "Treatment of murine lupus with cDNA encoding IFN-gammaR/Fc," *J Clin Invest.*, 106(2):207-215, Jul. 2000.
Lazarevic and Glimcher, "T-bet in disease," *Nat Immunol.*, 12(7):597-606, Jun. 20, 2011.
Lee et al., "Survivin expression and its clinical significance in pancreatic cancer " *BMC Cancer*, 5:127, Oct. 4, 2005.
Lee et al., "Increased vaccine-specific T cell frequency after peptide-based vaccination correlates with increased susceptibility to in vitro stimulation but does not lead to tumor regression," *J Immunol.*, 163(11):6292-6300, Dec. 1, 1999.
Leibovich et al., "Prediction of progression after radical nephrectomy for patients with clear cell renal cell carcinoma: a stratification tool for prospective clinical trials," *Cancer*, 97(7):1663-1671, Apr. 1, 2003.
Lenardo et al., "Mature T lymphocyte apoptosis—immune regulation in a dynamic and unpredictable antigenic environment," *Annu Rev Immunol.*, 17:221-253, 1999.
Lenschow et al., "CD28/B7 system of T cell costimulation," *Annu Rev Immunol.*, 14:233-258, 1996.
Levitt, "Accurate modeling of protein conformation by automatic segment matching," *J Mol Biol.*, 226(2):507-533, Jul. 20, 1992.
Lewinski, et al., RetroviralDNA integration: viral and cellular determinants of target-site selection, *PLoS Pathog.*, 2(6):e60, Epub Jun. 23, 2006.
Lewis et al., "Surrogate tumor antigen vaccination induces tumor-specific immunity and the rejection of spontaneous metastases," *Cancer Res.*, 65(7):2938-2946, Apr. 1, 2005.
Lewis, "PCR's Competitors Are Alive and Well and Moving Rapidly Towards Commercialization," *Genetic Engineering News*, vol. 12, 3 pages, 1992.
Li et al., "Anti-programmed death-1 synergizes with granulocyte macrophage colony-stimulating factor—secreting tumor cell immunotherapy providing therapeutic benefit to mice with established tumors," *Clin Cancer Res.*, 15(5):1623-1634, Epub Feb. 10, 2009.
Li et al., "Gemcitabine and arabinosylcytosin pharmacogenomics: genome-wide association and drug response biomarkers," *PLoS One.*, 4(11):e7765, Nov. 9, 2009.
Liang et al., "Autoantibody responses and pathology regulated by B7-1 and B7-2 costimulation in MRL/lpr lupus," *J Immunol.*, 165(6):3436-3443, Sep. 15, 2000.
Linsley et al., "Binding of the B cell activation antigen B7 to CD28 costimulates T cell proliferation and interleukin 2 mRNA accumulation" *J Exp Med.*, 173(3):721-730, Mar. 1, 1991.
Linsley et al., "Extending the B7 (CD80) gene family," *Protein Sci.*, 3(8):1341-1343, Aug. 1994.
Linsley et al., "T-cell antigen CD28 mediates adhesion with B cells by interacting with activation antigen 87188-1," *Proc Natl Acad Sci U S A.*, 87(13):5031-5035, Jul. 1990.
Liu et al., "B7DC/PDL2 promotes tumor immunity by a PD-1-independent mechanism," *J Exp Med.*, 197(12):1721-1730, Jun. 16, 2003.
Liu et al., "B7-H3 silencing increases paclitaxel sensitivity by abrogating Jak2/Stat3 phosphorylation," *Mol Cancer Ther.*, 10(6):960-971, Epub Apr. 25, 2011.
Liu et al., "Endogenous tumor-reactive CD8+ T cells are differentiated effector cells expressing high levels of CD11a and PD-1 but are unable to control tumor growth," *Oncoimmunology.*, 2(6):e23972, Epub Jun. 6, 2013.
Liu et al., "Fas-mediated apoptosis causes elimination of virus-specific cytotoxic T cells in the virus-infected liver," *J Immunol.*, 166(5):3035-3041, Mar. 1, 2001.
Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway," *Blood*, 110(1):296-304, Epub Mar. 15, 2007.
Lonberg et al., "Antigen-specific human antibodies from mice comprising four distinct genetic modifications," *Nature*, 368(6474):856-859, Apr. 28, 1994.
Losman et al., "Baboon anti-idiotype antibodies mimic a carcinoembryonic antigen epitope," *Int J Cancer.*, 46(2):310-314, Aug. 15, 1990.
Lu et al., "EGF-IL-18 fusion protein as a potential anti-tumor reagent by induction of immune response and apoptosis in cancer cells," *Cancer Lett.*, 260(1-2):187-197, Epub Dec. 21, 2007.
Luciano et al., "Phosphorylation of Bim-EL by Erk1/2 on serine 69 promotes its degradation via the proteasome pathway and regulates its proapoptotic function," *Oncogene.*, 22(43):6785-6793, Oct. 2, 2003.
Luettig et al., "Naive and memory T lymphocytes migrate in comparable numbers through normal rat liver: activated T cells accumulate in the periportal field," *J Immunol.*, 163(8):4300-4307, Oct. 15, 1999.
Lunsford et al., "Targeting LFA-1 and cd154 suppresses the in vivo activation and development of cytolytic (cd4-Independent) CD8+ T cells," *J Immunol.*, 175(12):7855-7866, Dec. 15, 2005.

(56) References Cited

OTHER PUBLICATIONS

Ma et al., "The DNA-dependent protein kinase catalytic subunit phosphorylation sites in human Artemis," *J Biol Chem.*, 280(40):33839-33846, Epub Aug. 10, 2005.
Ma et al., "The Role of PD-1 Ligand in Immune Evasion by Breast Cancer," Dana-Farber Cancer Institute Annual Summary Report May 1, 2002-Apr. 30, 2005, pp. 5-6, 9, 11, report date: May 2005.
Mah et al., "gammaH2AX: a sensitive molecular marker of DNA damage and repair," *Leukemia*, 24(4):679-686, Epub Feb. 4, 2010.
Mahotka et al., "Distinct in vivo expression patterns of survivin splice variants in renal cell carcinomas," *Int J Cancer*, 100(1):30-36, Jul. 1, 2002.
Mann et al., "Construction of a retrovirus packaging mutant and its use to produce helper-free defective retrovirus" *Cell*, 33(1):153-159, May 1983.
Martin et al. "Combination gene therapy with CD86 and the MHC Class II transactivator in the control of lung tumor growth," *J Immunol.*, 162(11):6663-6670, Jun. 1, 1999.
Mathiowitz et al., "Morphology of poly anhydride microsphere delivery systems," *Scanning Microsc.*, 4(2):329-340, Jun. 1990.
Mathiowitz et al., "Polyanhydride microspheres as drug carriers. I. Hot-melt microencapsulation," *J. Controlled Release*, 5(1):13-22, Jun. 1, 1987.
Mathiowitz et al., "Polyanhydride microspheres. IV. Morphology and characterization of systems made by spray drying," *J. Annl. Polymer Sci.* 45(1): 125-134, May 5, 1992.
Mathiowitz, Novel microcapsules for delivery systems, *Reactive Polymers*, 6(2):275-283, Oct. 31, 1987.
Mathiowitz, "Polyanhydride microspheres as drug carriers, II. Microencapsulation by solvent removal," *J. Appl. Polymer Sci.*, 35(3): 755-774, Feb. 20, 1988.
Mayo Clinic, "Mayo Clinic Discovers Potential Marker for Aggressive Kidney Cancer," Science Daily, Retrieved from the Internet: <URL: https://www.sciencedaily.com/releases/2004/11/041130200858.htm>, 2 pages, Dec. 9, 2004.
McCubrey et al., "Roles of the Raf/MEK/ERK pathway in cell growth, malignant transformation and drug resistance," *Biochim Biophys Acta.*, 1773(8):1263-1284, Epub Oct. 7, 2006.
McDermott et al., "PD-1 as a potential target in cancer therapy," *Cancer Med.*, 2(5):662-673. Epub Jul. 21, 2013.
McLachlin et al., "Retroviral-mediated gene transfer," *Prog Nucleic Acid Res Mol Biol.*, 38:91-135, 1990.
Mehal et al., "Antigen presentation by liver cells controls intrahepatic T cell trapping, whereas bone marrow-derived cells preferentially promote intrahepatic T cell apoptosis," *J Immunol.*, 167(2):667-673, Jul. 15, 2001.
Mehal et al., "TCR ligation on CD8+ T cells creates double-negative cells in vivo," *J Immunol.*, 161(4):1686-1693, Aug. 15, 1998.
Melero et al., "Amplification of tumor immunity by gene transfer of the co-stimulatory 4-1BB ligand: synergy with the CD28 co-stimulatory pathway," *Eur J Immunol.*, 28(3):1116-1121, Mar. 1998.
Melero et al., "Monoclonal antibodies against the 4-1BB T-cell activation molecule eradicate established tumors," *Nat Med.*, 3(6):682-685, Jun. 1997.
Melero et al., "NK1.1 cells express 4-1BB (CDw137) costimulatory molecule and are required for tumor immunity elicited by anti-4-1BB monoclonal antibodies," *Cell Immunol.*, 190(2):167-172, Dec. 15, 1998.
Melief et al., "Strategies for immunotherapy of cancer," *Advances in immunology*, 75:235-282, Jan. 1, 2000.
Mendez-Fernandez et al., "Clearance of Theiler's virus infection depends on the ability to generate a CD8+ T cell response against a single immunodominant viral peptide," *Eur J Immunol.*, 33(9):2501-2510, Sep. 2003.
Merrill, "Emergence of targeted immune therapies for systemic lupus," *Expert Opin Emerg Drugs*, 10(1):53-65, Feb. 2005.
Merritt et al., "Activation of p38 mitogen-activated protein kinase in vivo selectively induces apoptosis of CD8(+) but not CD4(+) T cells," *Mol Cell Biol.*, 20(3):936-946, Feb. 2000.

Metzler et al., "Solution structure of human CTLA-4 and delineation of a CD80/CD86 binding site conserved in CD28," *Nat Struct Biol.*, 4(7):527-531, Jul. 1997.
Miller et al., "Gene transfer by retrovirus vectors occurs only in cells that are actively replicating at the time of infection," *Mol Cell Biol.*, 10(8):4239-4242, Aug. 1990.
Miller et al., "Generation of helper-free amphotropic retroviruses that transduce a dominant-acting, methotrexate-resistant dihydrofolate reductase gene," *Mol Cell Biol.*, 5(3):431-437, Mar. 1985.
Miller et al., "Redesign of retrovirus packaging cell lines to avoid recombination leading to helper virus production," *Mol Cell Biol.*, 6(8):2895-2902, Aug. 1986.
Miller, "Human gene therapy comes of age," *Nature*, 357(6378):455-460, Jun. 11, 1992.
Misquitta et al., "Targeted disruption of gene function in *Drosophila* by RNA interference (RNA-i): A role for nautilus in embryonic somatic muscle formation," *Proc Natl Acad Sci U S A.*, 96(4):1451-1456, Feb. 16, 1999.
Mizuhara et al., "T cell activation-associated hepatic injury: mediation by tumor necrosis factors and protection by interleukin 6," *J Exp Med.*, 179(5):1529-1537, May 1, 1994.
Mohan et al., "Interaction between CD40 and its ligand gp39 in the development of murine lupus nephritis," *J Immunol.*, 154(3):1470-1480, Feb. 1, 1995.
Montesano et al, "Genetic alterations in esophageal cancer and their relevance to etiology and pathogenesis: a review," *Int J Cancer.*, 69(3):225-235, Jun. 21, 1996.
Morrison et al., "Chimeric human antibody molecules: mouse antigen-binding domains with human constant region domains," *Proc Natl Acad Sci U S A.*, 81(21):6851-6855, Nov. 1984.
Morse et al., "Abnormalities induced by the mutant gene Ipr: expansion of a unique lymphocyte subset," *J Immunol.*, 129(6):2612-2615, Dec. 1982.
Moss, "Poxvirus expression vectors," *Curr Top Microbiol Immunol.*, 158:25-38, 1992.
Moss, "Poxvirus vectors: cytoplasmic expression transferred genes," *Curr Opin Genet Dev.*, 3(1):86-90, Feb. 1993.
Moss, "Use of vaccinia virus as an infectious molecular cloning and expression vector," *Gene Amplif Anal.*, 3:201-213, 1993.
Moss, "Vaccinia virus vectors," Biotechnology, 20:345-362, 1992.
Moss, "Vaccinia virus: a tool for research and vaccine development," *Science*, 252(5013):1662-1667, Jun. 21, 1991.
Motzer et al., "Renal Cell Carcinoma," *N Engl J Med.*, 335(12):865-75, Sep. 19, 1996.
Mukherjee et al., "DNA-PK phosphorylates histone H2AX during apoptotic DNA fragmentation in mammalian cells," *DNA Repair (Amst).* 5(5):575-590, Epub Mar. 29, 2006.
Mumprecht et al., "Programmed death 1 signaling on chronic myeloid leukemia-specific T cells results in T-cell exhaustion and disease progression," *Blood.*, 114(8):1528-1536. Epub May 6, 2009.
Muyldermans, "Single domain camel antibodies: current status," *J Biotechnol.*, 74(4):277-302, Jun. 2001.
Nabel et al., "Recombinant gene expression in vivo within endothelial cells of the arterial wall," *Science*, 244(4910):1342-1344, Jun. 16, 1989.
National Cancer Institute, "Fact Sheet: Tumor Markers," cancer.gov [online] Dec. 7, 2011 [retrieved on Apr. 3, 2014]. Retrieved from the Internet: <URL: http://www.cancer.gov/cancertopics/factsheet/detection/tumor-markers/print>, 8 pages.
Nava-Parada et al., "Peptide vaccine given with a Toll-like receptor agonist is effective for the treatment and prevention of spontaneous breast tumors," *Cancer Res.*, 67(3):1326-1334, Feb. 1, 2007.
Nechiporuk et al., "The mouse SCA2 gene: cDNA sequence, alternative splicing and protein expression," *Hum Mol Genet.*, 7(8):1301-1309, Aug. 1998.
Needleman et al., "A general method applicable to the Search for similarities in the amino acid sequence of two proteins," *J Mol Biol.*, 48(3):443-453, Mar. 1970.
Nelson et al., "Tumor progression despite efficient tumor antigen cross-presentation and effective "arming" of tumor antigen-specific CTL," *J Immunol.*, 166(9):5557-5566, May 1, 2001.
Neves et al., "Surgical treatment of renal cancer with vena cava extension," *Br J Urol.*, 59(5):390-395, May 1987.

(56) References Cited

OTHER PUBLICATIONS

Newmark et al., "Preparation and properties of adducts of streptokinase and streptokinase-plasmin complex with poly ethylene glycol and pluronic polyol F38," *J Appl Biochem.*, 4:185-189, 1982.
Nicolau et al., "In vivo expression of rat insulin after intravenous administration of the liposome-entrapped gene for rat insulin I," *Proc Natl Acad Sci U S A.*, 80(4):1068-1072, Feb. 1983.
Nielsen et al., "Melanoma vaccines: the paradox of T cell activation without clinical response," *Cancer Chemother Pharmacol.*, 46 Suppl:S62-S66, 2000.
Nielsen et al., "Peptide nucleic acid (PNA). A DNA mimic with a peptide backbone," *Bioconjug Chem.*, 5(1):3-7, Jan.-Feb. 1994.
Nielsen et al., "Sequence-selective recognition of DNA by strand displacement with a thymine-substituted polyamide," *Science*, 254(5037):1497-1500, Dec. 6, 1991.
Nishimura et al., "Autoimmune dilated cardiomyopathy in PD-1 receptor-deficient mice," *Science*, 291(5502):319-322, Jan. 12, 2001.
Nishimura et al., "Development of lupus-like autoimmune diseases by disruption of the PD-1 gene encoding an ITIM motif-carrying immunoreceptor," *Immunity*, 11(2):141-151, Aug. 1999.
Nishimura et al., "Immunological studies on PD-1-deficient mice: implication of PD-1 as a negative regulator for B cell responses," *Int Immunol.*, 10(10):1563-1572, Oct. 1998.
Nisonhoff et al., "Separation of univalent fragments from the bivalent rabbit antibody molecule by reduction of disulfide bonds," *Arch Biochem Biophys.*, 89:230-244, Aug. 1960.
Niture et al., "Inhibitor of Nrf2 (INrf2 or Keap1) protein degrades Bcl-xL via phosphoglycerate mutase 5 and controls cellular apoptosis," *J Biol Chem.*, 286(52):44542-44556, Epub Nov. 9, 2011.
Ohigashi et al., "Clinical significance of programmed death-1 ligand-1 and programmed death-1 ligand-2 expression in human esophageal cancer," *Clin Cancer Res.*, 11(8):2947-2953, Apr. 15, 2005.
Okazaki et al., "PD-1 and PD-1 ligands: from discovery to clinical application," *Int Immunol.*, 19(7):813-824, Epub Jul. 2, 2007.
Opfermanet al., "Linear differentiation of cytotoxic effectors into memory T lymphocytes," *Science*, 283(5408):1745-1748, Mar. 12, 1999.
O'Reilly et al., "MEK/ERK-mediated phosphorylation of Bim is required to ensure survival of T and B lymphocytes during mitogenic stimulation," *J Immunol.*, 183(1):261-269, Jul. 1, 2009.
Orlandi et al., "Cloning immunoglobulin variable domains for expression by the polymerase chain reaction," *Proc Natl Acad Sci U S A.*, 86(10):3833-3837, May 1989.
Ostrov et al., "Structure of murine CTLA-4 and its role in modulating T cell responsiveness," *Science*, 290(5492):816-819, Oct. 27, 2000.
Ozkaynak et al., "Programmed death-1 targeting can promote allograft survival," *J Immunol.*, 169(11):6546-6553, Dec. 1, 2002.
Panta et al., "ATM and the catalytic subunit of DNA-dependent protein kinase activate NF-kappaB through a common MEK/extracellular signal-regulated kinase/p90(rsk) signaling pathway in response to distinct forms of DNA damage," *Mol Cell Biol.*, 24(5):1823-1835, Mar. 2004.
Pantuck et al., "The changing natural history of renal cell carcinoma," *J Urol.*, 166(5):1611-1623, Nov. 2001.
Pardoll, "Spinning molecular immunology into successful immunotherapy," *Nat Rev Immunol.*, 2(4):227-238, Apr. 2002.
Park et al., "B7-H1/CD80 interaction is required for the induction and maintenance of peripheral T-cell tolerance," *Blood.*, 116(8):1291-1298, Epub May 14, 2010.
Parker et al., "Potential utility of uroplakin III, thrombomodulin, high molecular weight cytokeratin, and cytokeratin 20 in noninvasive, invasive, and metastatic urothelial (transitional cell) carcinomas," *Am J Surg Pathol.*, 27(1):1-10, Jan. 2003.
Parsa et al., "Loss of tumor suppressor PTEN function increases B7-H1 expression and immunoresistance in glioma," *Nat Med.*, 13(1):84-88, Epub Dec. 10, 2006.

Patsoukis et al., "Selective effects of PD-1 on Akt and Ras pathways regulate molecular components of the cell cycle and inhibit T cell proliferation," *Sci Signal.*, 5(230):ra46, Jun. 26, 2012.
Pavelko et al., "The epitope integration site for vaccine antigens determines virus control while maintaining efficacy in an engineered cancer vaccine," *Mol Ther.*, 21(5):1087-1095, Epub Apr. 9, 2013.
Peach et al., "Both extracellular immunoglobulin-like domains of CD80 contain residues critical for binding T cell surface receptors CTLA-4 and CD28," *J Biol Chem.*, 270(36):21181-21187, Sep. 8, 1995.
Pece and Gutkind, "Signaling from E-cadherins to the MAPK pathway by the recruitment and activation of epidermal growth factor receptors upon cell-cell contact formation," *J Biol Chem.*, 275(52):41227-41233, Dec. 29, 2000.
Pedraza-Alva et al., "Activation of p38 MAP kinase by DNA double-strand breaks in V(D)J recombination induces a G2/M cell cycle checkpoint," *EMBO J.*, 25(4):763-773, Epub Feb. 2, 2006.
Peghini et al, [Immunophaenotyping in the diagnosis of lymphoma]. *Praxis (Bern 1994).*, 93(41):1687-1692, Oct. 6, 2004, Article in German, English abstract included.
Pei et al., "FKBP51 affects cancer cell response to chemotherapy by negatively regulating Akt," *Cancer Cell.*, 16(3):259-266, Sep. 8, 2009.
Penix et al., "Two essential regulatory elements in the human interferon gamma promoter confer activation specific expression in T cells," *J Exp Med.*, 178(5):1483-1496, Nov. 1, 1993.
Perriman et al., "Effective ribozyme delivery in plant cells," *Proc Natl Acad Sci U S A.*, 92(13):6175-6179, Jun. 20, 1995.
Petroff et al., "B7 family molecules: novel immunomodulators at the maternal-fetal interface," *Placenta*, 23 Suppl A:S95-101, Apr. 2002.
Piccini, "Vaccinia: virus, vector, vaccine," *Adv Virus Res.*, 34:43-64, 1988.
Plückthun et al., "Expression of functional antibody Fv and Fab fragments in *Escherichia coli*," *Methods Enzymol.*, 178:497-515, 1989.
Plückthun, "Antibodies from *Escherichia coli*." The Pharmacology of Monoclonal Antibodies. Handbook of Experimental Pharmacology, Springer Berlin Heidelberg, pp. 269-315, 1994.
Poirier, "Protective immunity evoked by oral administration of attenuated aroA *Salmonella typhimurium* expressing cloned streptococcal M protein," *J Exp Med.*, 168(1):25-32, Jul. 1, 1988.
Pollok et al., "4-1BB T-cell antigen binds to mature B cells and macrophages, and costimulates anti-mu-primed splenic B cells," *Eur J Immunol.*, 24(2):367-374, Feb. 1994.
Pollok et al., "Inducible T Cell Antigen 4-1BB," *J Immunol.*, 150(3):771-781, Feb. 1, 1993.
Ponder et al., "Tertiary templates for proteins. Use of packing criteria in the enumeration of allowed sequences for different structural classes," *J Mol Biol.*, 193(4):775-791, Feb. 20, 1987.
Porter, "The hydrolysis of rabbit γ-globulin and antibodies with crystalline papain," *Biochem J.*, 73:119-126, Sep. 1959.
Powell et al., "Compendium of excipients for parenteral formulations," *PDA J Pharm Sci Technol.*, 52(5):238-311, Sep.-Oct. 1998.
Prasad et al., "B7S1, a novel B7 family member that negatively regulates T cell activation," *Immunity*, 18(6):863-873, Jun. 2003.
Presta, "Antibody engineering," *Curr Opin Biotechnol.*, 2:593-596, 1992.
Presta, "Antibody engineering," *Curr Opin Biotechnol.*, 3(4):394-398, Aug. 1992.
Prévost-Blondel et al., "Tumor-infiltrating lymphocytes exhibiting high ex vivo cytolytic activity fail to prevent murine melanoma tumor growth in vivo," *J Immunol.*, 161(5):2187-2194, Sep. 1, 1998.
Pulko et al., "B7-h1 expressed by activated CD8 T cells is essential for their survival," *J Immunol.*, 187(11):5606-5614, Epub Oct. 24, 2011.
Pulko et al., "TLR3-stimulated dendritic cells up-regulate B7-H1 expression and influence the magnitude of CD8 T cell responses to tumor vaccination," *J Immunol.*, 183(6):3634-3641, Epub Aug. 26, 2009.

(56) References Cited

OTHER PUBLICATIONS

Qi et al., "Evidence that Ser87 of BimEL is phosphorylated by Akt and regulates BimEL apoptotic function," *J Biol Chem.*, 281(2):813-823, Epub Nov. 10, 2005.
Radhakrishnan et al., "Dendritic cells activated by cross-linking B7-DC (PD-L2) block inflammatory airway disease," *J Allergy Clin Immunol.*, 116(3):668-674, Sep. 2005.
Rai et al., "Tracking the total CD8 T cell response to infection reveals substantial discordance in magnitude and kinetics between inbred and outbred hosts," *J Immunol.*, 183(12):7672-7681, Dec. 15, 2009.
Rajewsky et al., "Genetics, expression, and function of idiotypes," *Annu Rev Immunol.*, 1:569-607, 1983.
Rathmell et al., "The central effectors of cell death in the immune system" *Annu. Rev. Immunol.*, 17:781-828, 1999.
Razi-Wolf, "Expression and function of the murine B7 antigen, the major costimulatory exudate cells," *Proc Natl Acad Sci U S A.*, 89(9):4210-4214, May 1, 1992.
Renauld et al., "Expression cloning of the murine and human interleukin 9 receptor cDNAs," *Proc Natl Acad Sci U S A.*, 89(12):5690-5694, Jun. 15, 1992.
Riechmann et al., "Reshaping human antibodies for therapy," *Nature*, 332(6162):323-327, Mar. 24, 1988.
Rincon et al., "JNK and p38 MAP kinases in CD4+ and CD8+ T cells," *Immunol Rev.*, 192:131-142, Apr. 2003.
Ritz et al., "Bioassay analysis using R," *J Stat Softw.*, 12(5):1-22, Jan. 19, 2005.
Rivoltini et al., "Immunity to cancer: attack and escape in T lymphocyte-tumor cell interaction," *Immunol Rev.*, 188:97-113, Oct. 2002.
Robison-Cox, "Multiple estimation of concentrations in immunoassay using logistic models," *J Immunol Methods*, 186(1):79-88, Oct. 12, 1995.
Romano et al., "Quelling: transient inactivation of gene expression in Neurospora crassa by transformation with homologous sequences," *Mol Microbiol.*, 6(22):3343-3353, Nov. 1992.
Romero et al., "Ex vivo staining of metastatic lymph nodes by class I major histocompatibility complex tetramers reveals high numbers of antigen-experienced tumor-specific cytolytic T lymphocytes," *J Exp Med.*, 188(9):1641-1650, Nov. 2, 1998.
Rosenberg, "Progress in human tumor immunology and immunotherapy," *Nature*, 411(6835):380-384, May 17, 2001.
Rosenfeld et al., "Adenovirus-mediated transfer of a recombinant alpha 1-antitrypsin gene to the lung epithelium in vivo," *Science*, 252(5004):431-434, Apr. 19, 1991.
Rousseaux et al, "Optimal conditions for the preparation of proteolytic fragments from monoclonal IgG of different rat IgG subclasses," *Methods Enzymol.*, 121:663-669, 1986.
Rowe et al., "PDL-1 blockade impedes T cell expansion and protective immunity primed by attenuated Listeria monocytogenes," *J Immunol.*, 180(11):7553-7557, Jun. 1, 2008.
Sadoff, "Oral *Salmonella typhimurium* vaccine expressing circumsporozoite protein protects against malaria," *Science*, 240(4850):336-338, Apr. 15, 1988.
Salama et al., "Critical role of the programmed death-1 (PD-1) pathway in regulation of experimental autoimmune encephalomyelitis," *J Exp Med.*, 198(1):71-78, Jul. 7, 2003.
Salib et al., "Utilization of sodium alginate in drug microencapsulation," *Pharm Ind.*, 40(11a):1230-1234, 1978.
Salih et al., "4-1 BB ligand—just another costimulating molecule?," *Int J Clin Pharmacol Ther.*, 40(8):348-353, Aug. 2002.
Salih et al., "The role of leukemia-derived B7-H1 (PD-L1) in tumor-T-call interactions in humans," *Exp Hematol.*, 34(7):888-894, Jul. 2006.
Salomon et al., "Complexities of CD28/B7: CTLA-4 costimulatory pathways in autoimmunity and transplantation," *Annu Rev Immunol.*, 19:225-252, 2001.
Samulski, "Targeted integration of adenoassociated virus (AAV) into human chromosome 19," *EMBO J.*, 10(12):3941-3950, Dec. 1991.
Sandhu, "Protein engineering of antibodies," *Crit Rev Biotechnol.*, 12(5-6):437-462, 1992.
Sanni et al., "Evolution of aminoacyl-tRNA synthetase quaternary structure and activity: *Saccharomyces cerevisiae* mitochondrial phenylalanyl-tRNA synthetase," *Proc Natl Acad Sci U S A.*, 88(19):8387-8391, Oct. 1, 1991.
Sarbassov et al., "Phosphorylation and regulation of Akt/PKB by the rictor-mTOR complex," *Science*, 307(5712):1098-1101, Feb. 18, 2005.
Sawhney et al., "Bioerodible hydrogels based on photopolymerized poly(ethylene glycol)-co-poly(.alpha.-hydroxy acid) diacrylate macromers," *Macromolecules*, 26(4):581-587, Jul. 1993.
Schafer, "Induction of a cellular immune response to a foreign antigen by a recombinant Listeria monocytogenes vaccine," *J Immunol.*, 149(1):53-59, Jul. 1, 1992.
Schmid et al, "Expression of AMPA receptor subunit flip/flop splice variants in the rat auditory brainstem and inferior colliculus," *J Comp Neurol.*, 430(2):160-171, Feb. 5, 2001.
Schmidt et al., "Extreme CD8 T cell requirements for anti-malarial liver-stage immunity following immunization with radiation attenuated sporozoites," *PLoS Pathog.*, 6(7):e1000998, Jul. 15, 2010.
Schmits et al., "LFA-1-deficient mice show normal CTL responses to virus but fail to reject immunogenic tumor," *J Exp Med.*, 183(4):1415-1426, Apr. 1, 1996.
Schurich et al., "The third signal cytokine IL-12 rescues the anti-viral function of exhausted HBV-specific CD8 T cells," *PLoS Pathog.*, 9(3):e1003208, Epub Mar. 14, 2013.
Schwartz et al, "Costimulation of T lymphocytes: the role of CD28, CTLA-4, and B7/BBI in interluekin-2 production and immunotherapy," *Cell*, 71(7):1065-1068, Dec. 24, 1992.
Schwartz et al., "Structural basis for co-stimulation by the human CTLA-4/B7-2 complex," *Nature*, 410(6828):604-608, Mar. 29, 2001.
Schwartz et al., "Structural mechanisms of costimulation," *Nat Immunol.*, 3(5):427-434, May 2002.
Sedletska et al., "Cisplatin is a DNA-damaging antitumour compound triggering multifactorial biochemical responses in cancer cells: importance of apoptotic pathways," *Curr Med Chem Anticancer Agents.*, 5(3):251-265, May 2005.
Seki et al., "Tumor-specific CTL kill murine renal cancer cells using both perforin and Fas ligand-mediated lysis in vitro, but cause tumor regression in vivo in the absence of perforin," *J Immunol.*, 168(7):3484-3492, Apr. 1, 2002.
Selenko-Gebauer et al., "B7-H1 (programmed death-1 ligand) on dendritic cells is involved in the induction and maintenance of T cell anergy," *J Immunol.*, 170(7):3637-3644, Apr. 1, 2003.
Seo et al., "Blockade of endogenous B7-H1 suppresses antibacterial protection after primary Listeria monocytogenes infection," *Immunology*, 123(1):90-99, Epub Oct. 25, 2007.
Shaknovich et al., "The promyelocytic leukemia zinc finger protein affects myeloid cell growth, differentiation, and apoptosis," *Mol Cell Biol.*, 18(9):5533-5545, Sep. 1998.
Shao et al., "Deficiency of the DNA repair enzyme ATM in rheumatoid arthritis," *J Exp Med.*, 206(6):1435-1449, Epub May 18, 2009.
Shao et al., "DNA-dependent protein kinase catalytic subunit mediates T-cell loss in rheumatoid arthritis," *EMBO Mol Med.*, 2(10):415-427, Oct. 2010.
Sharon et al., "Preparation of Fv fragment from the mouse myeloma XRPC-25 immunoglobulin possessing anti-dinitrophenyl activity," *Biochemistry*, 15(7):1591-1594, Apr. 6, 1976.
Sheather, "Density Estimation," *Statistical Sci.*, 19(4):588-597, 2004.
Shin et al., "Cooperative B7-1/2 (CD80/CD86) and B7-DC costimulation of CD4+ T cells independent of the PD-1 receptor," *J Exp Med.*, 198(1):31-38, Jul. 7, 2003.
Sica et al., "B7-H4, a molecule of the B7 family, negatively regulates T cell immunity," *Immunity*, 18(6):849-861, Jun. 2003.
Sica et al., "Biochemical and immunological characteristics of 4-1BB (CD137) receptor and ligand and potential applications in cancer therapy," *Arch Immunol Ther Exp (Warsz).*, 47(5):275-279, 1999.

(56) References Cited

OTHER PUBLICATIONS

Siddiqui et al., "Tumor-infiltrating Foxp3-CD4+ CD25+ T cells predict poor survival in renal cell carcinoma," *Clin Cancer Res.*, 13(7):2075-2081, Apr. 1, 2007.
Simon et al., "B7-h4 is a novel membrane-bound protein and a candidate serum and tissue biomarker for ovarian cancer," *Cancer Res.*, 66(3):1570-1575, Feb. 1, 2006.
Singer et al., "Optimal humanization of 1B4, an Anti-CD18 murine monoclonal antibody, is achieved by correct choice of human v-region framework sequences," *J Immunol.*, 150(7):2844-2857, Apr. 1, 1993.
Skerra et al., "Assembly of a functional immunoglobulin Fv fragment in *Escherichia coli*," *Science*, 240(4855):1038-1041, May 20, 1988.
Skolnick et al., "From genes to protein structure and function: novel applications of computational approaches in the genomic era," *Trends Biotechnol.*, 18(1):34-39, Jan. 2000.
Smith et al., Differential outcome of IL-2/anti-IL-2 complex therapy on effector and memory CD8+ T cells following vaccination with an adenoviral vector encoding EBV epitopes, *J Immunol.*, 186(10):5784-5790, Epub Apr. 11, 2011.
Smith et al., "Pulmonary deposition and clearance of aerosolized alpha-1-proteinase inhibitor administered to dogs and to sheep," *J Clin Invest.*, 84(4):1145-1154, Oct. 1989.
Sneller et al., "A novel lymphoproliferative/autoimmune syndrome resembling murine lpr/gld disease, "*J Clin Invest.*, 90(2):334-341, Aug. 1992.
Solier et al., "Death receptor-induced activation of the Chk2- and histone H2AX-associated DNA damage response pathways," *Mol Cell Biol.*, 29(1):68-82, Epub Oct. 27, 2008.
Sorge et al., "Amphotropic retrovirus vector system for human cell gene transfer," *Mol Cell Biol.*, 4(9):1730-1737, Sep. 1984.
Soriano, "Targeted and nontargeted liposomes for in vivo transfer to rat liver cells of a plasmid containing the preproinsulin I gene," *Proc Natl Acad Sci U S A.*, 80(23):7128-7131, Dec. 1983.
Soubeyrand et al., "Artemis phosphorylated by DNA-dependent protein kinase associates preferentially with discrete regions of chromatin," *J Mol Biol.*, 358(5):1200-1211, Epub Mar. 20, 2006.
Stammers et al., "BTL-II: A polymorphic locus with homology to the butyrolphilin gene family, located at the border of the major histocompatibility complex class II and class III regions in human and mouse," *Immunogenetics*, 51(4-5):373-382, Apr. 2000.
Stamper et al., "Crystal structure of the B7-1/CTLA-4 complex that inhibits human immune responses," *Nature*, 410(6828):608-611, Mar. 29, 2001.
Strome et al., "B7-H1 blockade augments adoptive T-cell immunotherapy for squamous cell carcinoma," *Cancer Res.*, 63(19):6501-6505, Oct. 1, 2003.
Strome et al., "Enhanced therapeutic potential of adoptive immunotherapy by in vitro CD28/4-1BB costimulation of tumor-reactive T cells against a poorly immunogenic, major histocompatibility complex class I-negative A9P melanoma," *J Immunother.*, 23(4):430-437, Jul.-Aug. 2000.
Subudhi et al., "Local expression of B7-H1 promotes organ-specific autoimmunity and transplant rejection," *J Clin Invest.*, 113(5):694-700, Mar. 2004.
Suda et al., "Why do defects in the Fas-Fas ligand system cause autoimmunity?" *J Allergy Clin Immunol.*, 100(6 Pt 2):S97-S101, Dec. 1997.
Summerton et al., "Morpholino antisense oligomers: design, preparation, and properties," *Antisense Nucleic Acid Drug Dev.*, 7(3):187-195, Jun. 1997.
Sun et al., "Administration of agonistic anti-4-1BB monoclonal antibody leads to the amelioration of experimental autoimmune encephalomyelitis," *J Immunol.*, 168(3):1457-1465, Feb. 1, 2002.
Sun et al., "Costimulatory molecule-targeted antibody therapy of a spontaneous autoimmune disease," *Nat Med.*, 8(12):1405-1413, Epub Nov. 11, 2002.
Sun et al., "Signaling of 4-1BB Leads to Amelioration of Experimental Autoimmune Encephalomyelitis," *FASEB J.*, vol. 5, p. A1210 Abstract 950.9, 2001.
Supplementary European Search Report in International Application No. 03764649.4-2107, dated Oct. 6, 2006, 5 pages.
Sutter et al., "Nonreplicating vaccinia vector efficiently expresses recombinant genes," *Proc Natl Acad Sci U S A.*, 89(22):10847-10851, Nov. 15, 1992.
Suzuki et al., "T cell-specific loss of Pten leads to defects in central and peripheral tolerance," *Immunity*, 14(5):523-534, May 2001.
Suzuki et al., "The dual functions of fas ligand in the regulation of peripheral CD8+ and CD4+ T cells," *Proc Natl Acad Sci U S A.*, 97(4):1707-1712, Feb. 15, 2000.
Swallow et al., "B7h, a novel costimulatory homolog of B7.1 and B7.2, is induced by TNFalpha," *Immunity*, 11(4):423-432, Oct. 1999.
Takahashi et al., "Cutting edge: 4-1BB is a bona fide CD8 T cell survival signal," *J Immunol.*, 162(9):5037-5040, May 1, 1999.
Takeda et al., "Critical contribution of liver natural killer T cells to a murine model of hepatitis," *Proc Natl Acad Sci U S A.*, 97(10):5498-5503, May 9, 2000.
Tamura et al., "B7-H1 costimulation preferentially enhances CD28-indepenent T-helper cell function," *Blood*, 97(6):1809-1816, Mar. 15, 2001.
Tamura et al., "Marrow stromal cells induce B7-H1 expression on myeloma cells, generating aggressive characteristics in multiple myeloma," *Leukemia*, 27(2):464-472, Epub Jul. 25, 2012.
Taylor et al., "Human immunoglobulin transgenes undergo rearrangement, somatic mutation and class switching in mice that lack endogenous IgM," *Int Immunol.*, 6(4):579-591, Apr. 1994.
Tazi-Ahnini et al., "Cloning, localization, and structure of new members of the butyrophilin gene family in the juxtatelomenc region of the major histocompatibility complex," *Immunogenetics*, 47(1):55-63, 1997.
Temin, "Safety considerations in somatic gene therapy of human disease with retrovirus vectors," *Hum Gene Ther.*, 1(2):111-123, Summer 1990.
Templeton et al., "Improved DNA: liposome complexes for increased systemic delivery and gene expression," *Nat Biotechnol.*, 15(7):647-652, Jul. 1997.
Theofilopoulos et al., "Tumour necrosis factor and other cytokines in murine lupus," *Ann Rheum Dis.*, 58(suppl 1):I49-55, Nov. 1, 1999.
Theofilopoulos et al., "Etiopathogenesis of Murine SLE," *Immunol Rev.*, 55:179-216, 1981.
Thompson et al., "cis-acting sequences required for inducible interleukin-2 enhancer function bind a novel Ets-related protein, Elf-1," *Mol Cell Biol.*, 12(3):1043-1053, Mar. 1992.
Thompson et al., "Costimulatory B7-H1 in renal cell carcinoma patients: Indicator of tumor aggressiveness and potential therapeutic target," *Proc Natl Acad Sci U S A.*, 101(49):17174-9. Epub Nov. 29, 2004.
Thompson et al., "Costimulatory molecule B7-H1 in primary and metastatic clear cell renal cell carcinoma," *Cancer*, 104(10):2084-2091, Nov. 15, 2005.
Thompson et al., "PD-1 is expressed by tumor-infiltrating immune cells and is associated with poor outcome for patients with renal cell carcinoma," *Clin Cancer Res.*, 13(6):1757-1761, Mar. 15, 2007.
Thompson et al., "Tumor B7-H1 is associated with poor prognosis in renal cell carcinoma patients with long-term follow-up," *Cancer Res.*, 66(7):3381-3385, Apr. 1, 2006.
Thompson et al., "Tumor masses support naive T cell infiltration, activation, and differentiation into effectors," *J Exp Med.*, 207(8):1791-1804, Epub Jul. 26, 2010.
Tian et al., "The relationship between the down-regulation of DNA-PKcs or Ku70 and the chemosensitization in human cervical carcinoma cell line HeLa," *Oncol Rep.*, 18(4):927-932, Oct. 2007.
Tiegs et al., "A T cell-dependent experimental liver injury in mice inducible by concanavalin A," *J Clin Invest.*, 90(1):196-203, Jul. 1992.
Titomirov, "In vivo electroporation and stable transformation of skin cells of newborn mice by plasmid DNA," *Biochim Biophys Acta.*, 1088(1):131-134, Jan. 17, 1991.

(56) References Cited

OTHER PUBLICATIONS

Todd et al., "Transcription of the interleukin 4 gene is regulated by multiple promoter elements," *J Exp Med.*, 177(6):1663-1674, Jun. 1, 1993.
Townsend et al., "Tumor rejection after direct costimulation of CD8+ T cells by B7-transfected melanoma cells," *Science*, 259(5093):368-370, Jan. 15, 1993.
Trabattoni et al. "B7-H1 is up-regulated in HIV infection and is a novel surrogate marker of disease progression" *Blood*, 101(7):2514-2520, Epub Dec. 5, 2002.
Tringler et al., "B7-h4 is highly expressed in ductal and lobular breast cancer " *Clin Cancer Res.*, 11(5):1842-1848, Mar. 1, 2005.
Truneh et al., "Early steps of lymphocyte activation bypassed by synergy between calcium ionophores and phorbol ester," *Nature.*, 313(6000):318-320, Jan. 24-30, 1985.
Tseng et al., "B7-DC, a new dendritic cell molecule with potent costimulatory properties for T cells," *J Exp Med.*, 193(7):839-846, Apr. 2, 2001.
Ueda et al., "Sequence-specific DNA damage induced by reduced mitomycin C and 7-N-(p-hydroxyphenyl)mitomycin C.," *Nucleic Acids Res.*, 12(17):6673-6683, Sep. 11, 1984.
Verhoeyen et al., "Reshaping human antibodies: grafting an antilysozyme activity," *Science*, 239(4847):1534-1536, Mar. 25, 1988.
Vesely et al., "Natural innate and adaptive immunity to cancer," *Annu Rev Immunol.*, 29:235-271, 2011.
Veuger et al., "Radiosensitization and DNA repair inhibition by the combined use of novel inhibitors of DNA-dependent protein kinase and poly(ADP-ribose) polymerase-1," *Cancer Res.*, 63(18):6008-6015, Sep. 15, 2003.
Vinay et al., "Role of 4-1BB in immune responses," *Semin Immunol.*, 10(6):481-489, Dec. 1998.
Wahl et al., "Improved radioimaging and tumor localization with monoclonal F(ab')2" *J Nucl Med.*, 24(4):316-25, Apr. 1983.
Walunas et al., "CTLA-4 ligation blocks CD28-dependent T cell activation," *J Exp Med.*, 183(6):2541-2550, Jun. 1, 1996.
Wang et al., "Costimulation of T cells by B7-H2, a B7-like molecule that binds ICOS," *Blood*, 96(8):2808-2813, Oct. 15, 2000.
Wang et al., "Doxorubicin induces apoptosis in normal and tumor cells via distinctly different mechanisms. intermediacy of H(2)O(2)- and p53-dependent pathways," *J Biol Chem.*, 279(24):25535-25543, Epub Mar. 30, 2004.
Wang et al., "Ligand binding sites of inducible costimulator and high avidity mutants with improved function," *J Exp Med.*, 195(8):1033-1041, Apr. 15, 2002.
Wang et al., "Molecular modeling and functional mapping of B7-H1 and B7-DC uncouple costimulatory function from PD-1 interaction," *J Exp Med.*, 197(9):1083-1091, Epub Apr. 28, 2003.
Wang, "Lyophilization and development of solid protein pharmaceuticals," *Int J Pharm.*, 203(1-2):1-60, Aug. 10, 2000.
Wang, "pH-sensitive immunoliposomes mediate target-cell-specific delivery and controlled expression of a foreign gene in mouse," *Proc Natl Acad Sci U S A.*, 84(22):7851-7855, Nov. 1987.
Ward et al., "Binding activities of a repertoire of single immunoglobulin variable domains secreted from *Escherichia coli,"* *Nature*, 341(6242):544-546, Oct. 12, 1989.
Webster et al., "Targeting molecular and cellular inhibitory mechanisms for improvement of antitumor memory responses reactivated by tumor cell vaccine," *J Immunol.*, 179(5):2860-2869, Sep. 1, 2007.
Weiss, "Hot Prospect for New Gene Amplifier: Ligase chain reaction, a combination DNA amplifier and genetic screen could do for DNA diagnostics what PCR has done for basic molecular biology," *Science*, 254(5036):1292-1293, Nov. 29, 1991.
Wherry et al., "Lineage relationship and protective immunity of memory CD8 T cell subsets," *Nat Immunol.*, 4(3):225-234, Epub Feb. 3, 2003.
Wick et al., "The hepatic immune system," *Crit Rev Immunol.*, 22(1):47-103, 2002.

Wilcox et al., "Provision of antigen and CD137 signaling breaks immunological ignorance, promoting regression of poorly immunogenic tumors," *J Clin Invest.*, 109(5):651-659, Mar. 2002.
Williams et al., "Introduction of foreign genes into tissues of living mice by DNA-coated microprojectiles," *Proc Natl Acad Sci U S A.*, 88(7):2726-2730, Apr. 1, 1991.
Williams et al., "The immunoglobulin superfamily—domains for cell surface recognition," *Annu Rev Immunol.*, 6:381-405, 1988.
Williams et al., "Nitric oxide synthase plays a signaling role in TCR-triggered apoptotic death," *J Immunol.*, 161(12):6526-6531, Dec. 15, 1998.
Willmore et al., "A novel DNA-dependent protein kinase inhibitor, NU7026, potentiates the cytotoxicity of topoisomerase II poisons used in the treatment of leukemia," *Blood*, 103(12):4659-4665, Epub Mar. 9, 2004.
Winter et al., "Man-made antibodies," *Nature*, 349(6307):293-299, Jan. 24, 1991.
Winter et al., "Making antibodies by phage display technology," *Annu Rev Immunol.*, 12:433-455, 1994.
Wintterle et al., "Expression of the B7-related molecule B7-H1 by glioma cells: a potential mechanism of immune paralysis," *Cancer Res.*, 63(21):7462-7467, Nov. 1, 2003.
Wofsy et al., "The proliferating cells in autoimmune MRL/lpr mice lack L3T4, an antigen on "helper" T cells that is involved in the response to class II major histocompatibility antigens," *J Immunol.*, 132(6):2686-2689, Jun. 1984.
Wofsy, "Treatment of murine lupus with anti-CD4 monoclonal antibodies," *Immunol Ser.*, 59:221-236, 1993.
Wolff, "Direct gene transfer into mouse muscle in vivo " *Science*, 247(4949 Pt 1):1465-1468, Mar. 23, 1990.
Wong et al., "Human GM-CSF: molecular cloning of the complementary DNA and purification of the natural and recombinant proteins," *Science*, 228(4701):810-815, May 17, 1985.
Wu et al., The double-edged sword of activation-induced cytidine deaminase, *J Immunol.*, 174(2):934-941, Jan. 15, 2005.
Wu, "Receptor-mediated gene delivery and expression in vivo," *J Biol Chem.*, 263(29):14621-14624, Oct. 15, 1988.
Wu, "Targeting genes: delivery and persistent expression of a foreign gene driven by mammalian regulatory elements in vivo," *J Biol Chem.*, 264(29):16985-16987, Oct. 15, 1989.
Xu et al., "A potentia new pathway for PD-L1 costimulation of the CD8-T cell response to Listeria monocytogenes infection," *PLoS One*, 8(2):e56539, Epub Feb. 11, 2013.
Xu et al., "The inducible expression of the tumor suppressor gene PTEN promotes apoptosis and decreases cell size by inhibiting the PI3K/Akt pathway in Jurkat T cells," *Cell Growth Differ.*, 13(7):285-296, Jul. 2002.
Yamamoto et al., "B7-H1 expression is regulated by MEK/ERK signaling pathway in anaplastic large cell lymphoma and Hodgkin lymphoma," *Cancer Sci.*, 100(11):2093-2100, Epub Aug. 1, 2009.
Yamazaki et al., "Expression of programmed death 1 ligands by murine T cells and APC," *J Immunol.*, 169(10):5538-5545, Nov. 15, 2002.
Yang et al., "In vitro priming of tumor-reactive cytolytic T lymphocytes by combining IL-10 with B7-CD28 costimulation," *J Immunol.*, 155(8):3897-3903, Oct. 15, 1995.
Yang et al., "In vivo and in vitro gene transfer to mammalian somatic cells by particle bombardment," *Proc Natl Acad Sci U S A.*, 87(24):9568-9572, Dec. 1990.
Yang, "Gene transfer into mammalian somatic cells in vivo," *Crit Rev Biotechnol.*, 12(4):335-356, 1992.
Yoshinaga et al., "T-cell co-stimulation through B7RP-1 and ICOS," *Nature*, 402(6763):827-832, Dec. 16, 1999.
Yotsumoto et al., "Endosomal translocation of CpG-oligodeoxynucleotides inhibits DNA-PKcs-dependent IL-10 production in macrophages," *J Immunol.*, 180(2):809-816, Jan. 15, 2008.
Youngnak et al., "Differential binding properties of B7-H1 and B7-DC to programmed death-1," *Biochem Biophys Res Commun.*, 307(3):672-677, Aug. 1, 2003.
Yuan et al., "Focus on histone variant H2AX: to be or not to b," *FEBS Lett.*, 584(17):3717-3724, Epub May 21, 2010.

(56) References Cited

OTHER PUBLICATIONS

Zang et al., "B7x: a widely expressed b7 family member that inhibits T cell activation," *Proc Natl Acad Sci U S A.*, 100(18):10388-10392, Epub Aug. 14, 2003.

Zang et al., "The B7 family and cancer therapy: costimulation and coinhibition," *Clin Cancer Res.*, 13(18 Pt 1):5271-5279, Sep. 15, 2007.

Zelenin et al., "Genetic transformation of mouse cultured cells with the help of high-velocity mechanical DNA injection," *FEBS Lett.*, 244(1):65-67, Feb. 13, 1989.

Zelenin et al., "High-velocity mechanical DNA transfer of the chloramphenicolacetyl transferase gene into rodent liver, kidney and mammary gland cells in organ explants and in vivo," *FEBS Lett.*, 280(1):94-96, Mar. 11, 1991.

Zhang et al., "PD-1/PD-L1 interactions inhibit antitumor immune responses in a murine acute myeloid leukemia model," *Blood*, 114(8):1545-1552, Epub May 5, 2009.

Zhang et al., "Theiler's virus-infected L-selectin-deficient mice have decreased infiltration of CD8(+) T lymphocytes in central nervous system but clear the virus," *J Neuroimmunol.*, 116(2):178-187, Jun. 1, 2001.

Zhou et al., "Inducible-costimulator-mediated suppression of human immunodeficiency virus type 1 replication in CD4+ T lymphocytes," *Virology*, 325(2):252-263, Aug. 1, 2004.

Zou et al., "Inhibitory B7-family molecules in the tumour microenvironment," *Nat Rev Immunol.*, 8(6):467-477, Jun. 2008.

Zula et al., "The role of cell type-specific responses in IFN-βtherapy of multiple sclerosis," *Proc Natl Acad Sci U S A.*, 108(49):19689-19694, Epub Nov. 21, 2011.

Zumla et al. "Granulomatous infections: etiology and classification," *Clin Infect Dis.*, 23(1):146-158, Jul. 1996.

Zwiebel et al., "Drug delivery by genetically engineered cell implants," *Ann N Y Acad Sci.*, 618:394-404, 1991.

*Academic Press Dictionary of Science and Technology* (definition for the term "polyclonal"); Oxford: Elsevier Science & Technology (1996); retrieved Oct. 22, 2008, from http://www.credoreference.com/entry/3144515/.

Butte et al., "PD-L1 interacts specifically with B7-1 to inhibit T cell proliferation," *Immunity.*, 27:111-122, 2007.

Harlow and Lane, *Antibodies: A Laboratory Manual*; Cold Spring Harbor Laboratory Press, Cold Spring Harbor, NY, pp. 553, 555-582, 584-589, and 591-612, 1988.

Janeway et al., "The immunogenicity of a protein depends on its presentation to T cells," in *Immunobiology: The Immune System in Health and Disease*, Elsevier Science., 4:36, 1999.

Paterson et al., "The PD-L1:B7-1 pathway restrains diabetogenic effector T cells in vivo," *J Immunol.*, 187(3):1097-1105, Aug. 1, 2011.

Topalian et al., "Safety, activity, and immune correlates of anti-PD-1 antibody in cancer," *New Engl J Med.*, 368(26):2443-2454, Jun. 28, 2012.

European Office Action in Application No. EP 14850189.3, dated Mar. 24, 2017, 5 pages.

European Search Report for Application No. EP 14850189.3, dated Feb. 27, 2017, 5 pages.

International Preliminary Report on Patentability in International Application No. PCT/US2015/031993, dated Nov. 22, 2016, 11 pages.

International Preliminary Report on Patentability in International Application No. PCT/US2015/032016, dated Jan. 24, 2017, 11 pages.

International Search Report and Written Opinion for PCT/US16/58852, dated Apr. 28, 2017, 15 pages.

Dronca et al., "BCL-2-interacting mediator of cell death (Bim) is a novel biomarker for response to anti-PD-1 therapy in patients with advanced melanoma," *Immunotherapy*, 8(12)1351-1353, Dec. 1, 2016.

Dronca et al., "T cell Bim levels reflect responses to anti-PD-1 cancer therapy," *JCI Insight*, 1(6):e86014, May 5, 2016, 14 pages.

European Office Action in Application No. EP 14850189.3, dated Oct. 26, 2017, 11 pages.

Haugland et al, "Unit 16.5 antibody conjugates for cell biology," *Current Protocols in Cell Biology*, 6:16.5:16.5-16.5.22, Epub May 1, 2001.

U.S. Appl. No. 15/692,656, filed Aug. 31, 2017, Kwon et al.

\* cited by examiner

FIGURE 10

```
  1 atgaggatat ttgctgtctt tatattcatg acctactggc atttgctgaa cgcatttact
 61 gtcacggttc ccaaggacct atatgtggta gagtatggta gcaatatgac aattgaatgc
121 aaattcccag tagaaaaaca attagacctg gctgcactaa ttgtctattg ggaaatggag
181 gataagaaca ttattcaatt tgtgcatgga gaggaagacc tgaaggttca gcatagtagc
241 tacagacaga gggcccggct gttgaaggac cagctctccc tgggaaatgc tgcacttcag
301 atcacagatg tgaaattgca ggatgcaggg gtgtaccgct gcatgatcag tgcacttcag
361 gccgactaca agcgaattac tgtgaaagtc aatgcccccat acaacaaaat caaccaaaga
421 atttggttg tggatccagt cacctctgaa catgaactga catgtcaggc tgagggctac
481 cccaaggccg aagtcatctg gacaagcagt ttcaatgtga tcctgagtgg taagaccacc
541 accaccaatt ccaagagaga ggagaagctt ctactgcact ccagcacact gagaatcaac
601 acaacaacta atgagatttt ctactgcact tttaggagat tagatcctga ggaaaaccat
661 acagctgaat tggtcatccc agaactacct ctggcacatc cttgtgtag cactgacatt
721 ttggtaattc tgggagccat cttattatgc cttggtgtag cactgacatt catcttccgt
781 ttaagaaaag ggagaatgat ggatgtgaaa aatgtggca tccaagatac aaactcaaag
841 aagcaaagtg atacacattt ggaggagacg taa (SEQ ID NO:1)

1 MRIFAVFIFM TYWHLLNAFT VTVPKDLYVV EYGSNMTIEC KFPVEKQLDL AALIVYWEME
 61 DKNIIQFVHG EEDLKVQHSS YRQRARLLKD QLSLGNAALQ ITDVKLQDAG VYRCMISYGG
121 ADYKRITVKV NAPYNKINQR ILVVDPVTSE HELTCQAEGY PKAEVIWTSS DHQVLSGKTT
181 TTNSKREEKL FNVTSTLRIN TTTNEIFYCT FRRLDPEENH TAELVIPELP LAHPPNERTH
241 LVILGAILLC LGVALTFIFR LRKGRMMDVK KCGIQDTNSK KQSDTHLEET (SEQ ID NO:2)
```

FIGURE 11

```
  1 gcctgagcag tggagaaggc ggcactctgg tgggctgct  ccaggcatgc agatcccaca
 61 ggcgccctgg ccagtcgtct gggcgtgct  acaactgggc tggcggccag gatggttctt
121 agactcccca gacaggccct ggaaccccc  caccttctcc ccagccctgc tcgtggtgac
181 cgaaggggac aacgccacct tcacctgcag cttctccaac acatcggaga gcttcgtgct
241 aaactggtac cgcatgagcc ccagcaacca gacggacaag ctggccgctt tccccgagga
301 ccgcagccag cccggccagg actgccgctt ccgtgtcaca caactgccca acgggcgtga
361 cttccacatg agcgtggtca gggcccggcg caatgacagc ggcacctacc tctgtgggc
421 catctccctg gcccccaagg cgcagatcaa agagagcctg cgggcagagc tcaggtgac
481 agagagaagg gcagaagtgc ccacagccca cccccagccc tcacccaggc cagccggcca
541 gttccaaacc ctggtggttg gtgtcgtggg cggcctgctg ggcagcctgg tgctgctagt
601 ctgggtcctg gccgtcatct gctcccgggc gctcacgagc acaataggag ccaggcgcac
661 cggccagccc ctgaaggagg acccctcagc cgtgcctgtg ttctctgtgg actatgggga
721 gctggatttc cagtggcgag agaagaccc  gtgccccc   gtgccctgtg tccctgagca
781 gacggagtat gccaccattg tctttcctag cggaatgggc acctcatccc ccgcccgcag
841 gggctcagcc gacggcccct ggagtgccca gccactgagg cctgaggatg gacactgctc
901 ttggcccctc tgaccggctt ccttggccac cagtgttctg cagaccct (SEQ ID NO:3)
```

```
  1 MQIPQAPWPV VWAVLQLGWR PGWFLDSPDR PWNPPTFSPA LLVVTEGDNA TFTCSFSNTS
 61 ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGVVGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (SEQ ID NO:4)
```

FIGURE 12A

```
   1 gacaagtact gagtgaactc aaaccctctg taaagtaaca gaagttagaa ggggaaatgt cgcctctctg aagattaccc
  81 aaagaaaaag tgatttgtca ttgctttata gactgtaaga agagaacatc tcagaagtgg agtcttaccc tgaaatcaaa
 161 ggatttaaag aaaaagtgga attttctttc agcaagctgt gaactaaaat ccacaacctt tggagaccca ggaacacccct
 241 ccaatctctg tgtgtttgt aaacatcact ggagggtctt ctacgtgagc aattggattg tcatcagccc tgcctgtttt
 321 gcacctggga agtgccctgg tcttactgg gtccaaattg ttggctttca cttttgaccc taagcatctg agccatggg
 401 ccacacacg agcagggaa catccaccatc caagtgtcca tacctcaatt tcttcagct cttgtgctg gctggtcttt
 481 ctcacttctg ttcagtgtt atccacgtga ccaaggaagt gaaagaagtg gcaacgctgt cctgtgtca caatgtttct
 561 gttgaagagc tggcacaaaa tcgcattcac tggcaaaagg agaagaaaat ggtgctgact atgatgtctg gggacatgaa
 641 tatatgcccc gagtacaaga accggaccat ctttgatatc actaataacc tctccattgt gatcctgcct ctgcgcccat
 721 ctgacgaggg cacatacgag tgtgttgttc tgaagtatga aaagacgct ttcaagcggg aacacctggc tgaagtgacg
 801 ttatcagtca aagctgactt cctacacct agtatatctg actttgaaat tccaacttct aatattagaa ggataatttg
 881 ctcaacctct ggaggttttc cagagcctca cctctcctgg ttgaaaatg gagaagaatt aaatgccatc aacacaacag
 961 tttcccaaga tcctgaaact gagctctatg ctgttagcag caaactggat ttcaatatga caaccaacca cagcttcatg
1041 tgtctcatca agtatggaca tttaagagtg aatcagacct tcaactggaa tacaaccaag caagagcatt ttcctgataa
1121 cctgctccca tcctggccca ttaccttaat ctcagtaaat ggaatttttg tgatatgctg cctgacctac tgctttgccc
1201 caagatgcag agagagaagg aggaatgaga gattgagaag ggaaagtgta cgcctgtat aacagtgtcc gcagaagcaa
1281 gggctgaaa agatctgaag gtcccacctc catttgcaat tgacctcttc actttcagga ctttgcagga agatatggt
1361 ccaccttgcc ctttacgtat ctgctcttag gtgcttctc acttcagttg ctttgcagga agtgtctaga ggaatatggt
1441 gggcacagaa gtagctctgg tgaccttgat caagtgttt caagtgcact gaattcttag tctggaagg gacttagag
1521 aataccagtg ttattaatga caaagcact gaggcccagg gaggtgaccc gaattataaa ggccagcgcc agaaccccaga
1601 tttcctaact ctggtgctct ttcccttat cagtttgact gtggcctgtt aactggtata tacatatata tgtcaggcaa
1681 agtgctgctg gaagtagaat ttgtccaata acaggtcaac ttcagagact atctgatttc ctaatgtcag agtagaagat
1761 tttatgctgc tgtttacaaa agcccaatgt aatgcatagg aagtatggca tgaacatctt taggagacta atggaaatat
1841 tattggtgtt taccagtat tccattttt tcattgtgtt ctctattgct gctctctcac tccccatga ggtacagcag
1921 aaaggagaac tatccaaaac taattcctc tgacatgtaa gacgaatgat ttaggtacgt caaagcagta gtcaaggagg
2001 aaaggatag tccaaagact taactgttc atattggact gataatctct ttaaatggct ttatgctagt ttgacctcat
2081 ttgtaaaata tttatgagaa agttctcatt aaaatgaga tcgttgttta cagtgtatgt actaagcagt aagctatctt
2161 caaatgtcta agtagtaac tttccatagg gcctcttag atccctaaga tggcttttc tccttggtat ttctggtct
2241 ttctgacatc agcagagaac tggaaagaca tagccaactg ctgttcatgt tactccatgac tcctttctct aaaactgcct
2321 tccacaattc actagaccag aagtggacgc aacttaagct gggataatca cattatcatc tgaaaatctg gagttgaaca
2401 gcaaagaag acaacatttc tcaaatgcac atctcatggc agctaagcca catgctggg atttaaagcc tttagagcca
2481 gccatggct ttagctacct cactatgctg cttcacaaac cttgctcctg tgtaaaacta tattctcagt gtaggcaga
2561 gaggtctaac accaacataa ggtactagca gtgtttcccg tattgacagg aatacttaac tcaataattc tttcttttc
2641 catttagtaa cagttgtgat gactatgttt cattctaag taattcctgt attctacagc agatactttg tcagcaatac
2721 taagggaaga aacaaagttg accgttct ttaataa (SEQ ID NO:5)
```

FIGURE 12B

```
  1 MGHTRRQGTS PSKCPYLNFF QLLVLAGLSH FCSGVIHVTK EVKEVATLSC GHNVSVEELA
 61 QTRIYWQKEK KMVLTMMSGD MNIWPEYKNR TIFDITNNLS IVILALRPSD EGTYECVVLK
121 YEKDAFKREH LAEVTLSVKA DFPTPSISDF EIPTSNIRRI ICSTSGGFPE PHLSWLENGE
181 ELNAINTTVS QDPETELYAV SSKLDFNMTT NHSFMCLIKY GHLRVNQTFN WNTTKQEHFP
241 DNLLPSWAIT LISVNGIFVI CCLTYCFAPR CRERRRNERL RRESVRPV (SEQ ID NO:6)
```

FIGURE 17A
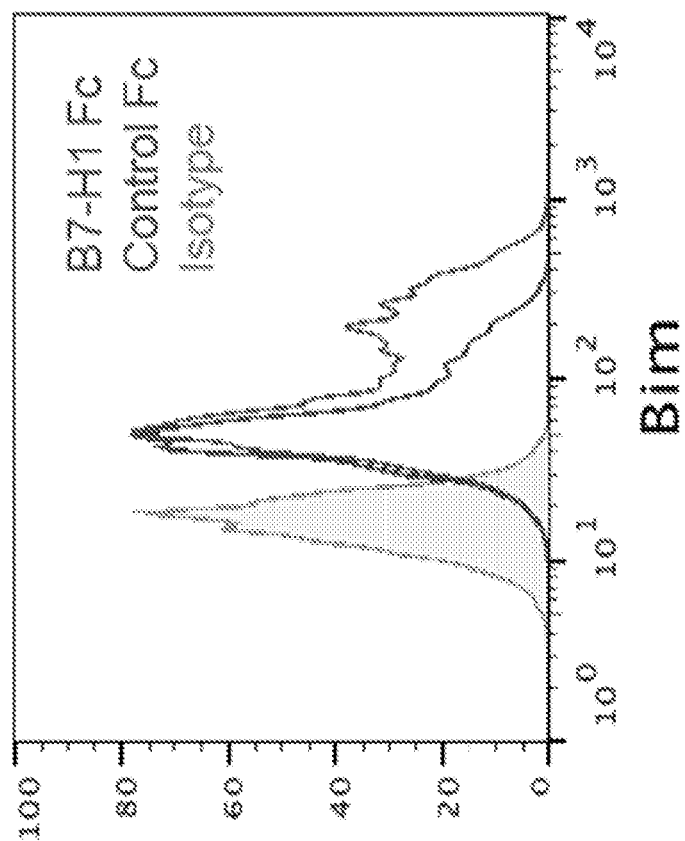
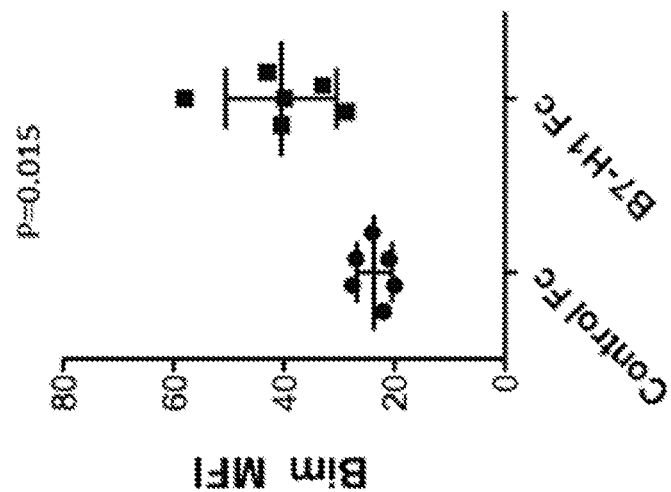

SEQUENCE LISTING

<160> NUMBER OF SEQ ID NOS: 6

<210> SEQ ID NO 1
<211> LENGTH: 873
<212> TYPE: DNA
<213> ORGANISM: Homo sapiens

<400> SEQUENCE: 1

| | |
|---|---|
| atgaggatat ttgctgtctt tatattcatg acctactggc atttgctgaa cgcatttact | 60 |
| gtcacggttc ccaaggacct atatgtggta gagtatggta gcaatatgac aattgaatgc | 120 |
| aaattcccag tagaaaaaca attagacctg gctgcactaa ttgtctattg ggaaatggag | 180 |
| gataagaaca ttattcaatt tgtgcatgga gaggaagacc tgaaggttca gcatagtagc | 240 |
| tacagacaga gggcccggct gttgaaggac cagctctccc tgggaaatgc tgcacttcag | 300 |
| atcacagatg tgaaattgca ggatgcaggg gtgtaccgct gcatgatcag ctatggtggt | 360 |
| gccgactaca agcgaattac tgtgaaagtc aatgccccat acaacaaaat caaccaaaga | 420 |
| attttggttg tggatccagt cacctctgaa catgaactga catgtcaggc tgagggctac | 480 |
| cccaaggccg aagtcatctg gacaagcagt gaccatcaag tcctgagtgg taagaccacc | 540 |
| accaccaatt ccaagagaga ggagaagctt ttcaatgtga ccagcacact gagaatcaac | 600 |
| acaacaacta atgagatttt ctactgcact tttaggagat tagatcctga ggaaaaccat | 660 |
| acagctgaat tggtcatccc agaactacct ctggcacatc ctccaaatga aggactcac | 720 |
| ttggtaattc tgggagccat cttattatgc cttggtgtag cactgacatt catcttccgt | 780 |
| ttaagaaaag ggagaatgat ggatgtgaaa aaatgtggca tccaagatac aaactcaaag | 840 |
| aagcaaagtg atacacattt ggaggagacg taa | 873 |

<210> SEQ ID NO 2
<211> LENGTH: 290
<212> TYPE: PRT
<213> ORGANISM: Homo sapiens

<400> SEQUENCE: 2

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser

```
            165                 170                 175
Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290

<210> SEQ ID NO 3
<211> LENGTH: 948
<212> TYPE: DNA
<213> ORGANISM: Homo sapiens

<400> SEQUENCE: 3
gcctgagcag tggagaaggc ggcactctgg tggggctgct ccaggcatgc agatcccaca      60
ggcgccctgg ccagtcgtct gggcggtgct acaactgggc tggcggccag gatggttctt     120
agactcccca gacaggccct ggaaccccca ccttctccc cagccctgc tcgtggtgac       180
cgaaggggac aacgccacct tcacctgcag cttctccaac acatcggaga gcttcgtgct     240
aaactggtac cgcatgagcc ccagcaacca gacggacaag ctggccgctt ccccgagga     300
ccgcagccag cccggccagg actgccgctt ccgtgtcaca caactgccca cgggcgtga     360
cttccacatg agcgtggtca gggcccggcg caatgacagc ggcacctacc tctgtggggc     420
catctccctg ccccccaagg cgcagatcaa agagagcctg cgggcagagc tcagggtgac     480
agagagaagg gcagaagtgc ccacagccca ccccagcccc tcacccaggc cagccggcca    540
gttccaaacc ctggtggttg tgtcgtggg cggcctgctg ggcagcctgg tgctgctagt      600
ctgggtcctg gccgtcatct gctcccgggc cgcacgaggg acaataggag ccaggcgcac     660
cggccagccc ctgaaggagg accctcagc cgtgcctgtg ttctctgtgg actatgggga     720
gctggatttc cagtggcgag agaagacccc ggagcccccc gtgccctgtg tccctgagca    780
gacggagtat gccaccattg tctttcctag cggaatgggc acctcatccc cgcccgcag    840
gggctcagcc gacggccctc ggagtgccca gccactgagg cctgaggatg acactgctc    900
ttggccctc tgaccggctt ccttggccac cagtgttctg cagaccct                  948

<210> SEQ ID NO 4
<211> LENGTH: 288
<212> TYPE: PRT
<213> ORGANISM: Homo sapiens

<400> SEQUENCE: 4

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30
```

```
Asn Pro Pro Thr Phe Ser Pro Ala Leu Leu Val Val Thr Glu Gly Asp
             35                   40                  45

Asn Ala Thr Phe Thr Cys Ser Phe Ser Asn Thr Ser Glu Ser Phe Val
         50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 5
<211> LENGTH: 2757
<212> TYPE: DNA
<213> ORGANISM: Homo sapiens

<400> SEQUENCE: 5
gacaagtact gagtgaactc aaaccctctg taaagtaaca gaagttagaa ggggaaatgt      60
cgcctctctg aagattaccc aaagaaaaag tgatttgtca ttgctttata gactgtaaga    120
agagaacatc tcagaagtgg agtcttaccc tgaaatcaaa ggatttaaag aaaaagtgga    180 attttcttc agcaagctgt gaaactaaat ccacaacctt tggagaccca ggaacaccct    240
ccaatctctg tgtgttttgt aaacatcact ggagggtctt ctacgtgagc aattggattg    300
tcatcagccc tgcctgtttt gcacctggga agtgccctgg tcttacttgg gtccaaattg    360
ttggctttca cttttgaccc taagcatctg aagccatggg ccacacacgg aggcagggaa    420
catcaccatc caagtgtcca tacctcaatt tctttcagct cttggtgctg gctggtcttt    480
ctcacttctg ttcaggtgtt atccacgtga ccaaggaagt gaaagaagtg caacgctgt    540 cctgtggtca atgtttcct gttgaagagc tggcacaaac tcgcatctac tggcaaaagg    600
agaagaaaat ggtgctgact atgatgtctg gggacatgaa tatatggccc gagtacaaga    660
```

```
accggaccat ctttgatatc actaataacc tctccattgt gatcctggct ctgcgcccat    720
ctgacgaggg cacatacgag tgtgttgttc tgaagtatga aaaagacgct ttcaagcggg    780
aacacctggc tgaagtgacg ttatcagtca agctgactt ccctacacct agtatatctg    840
actttgaaat ccaacttct aatattgaa ggataatttg ctcaacctct ggaggttttc     900
cagagcctca cctctcctgg ttggaaaatg agaagaatt aaatgccatc aacacaacag     960
tttcccaaga tcctgaaact gagctctatg ctgttagcag caaactggat ttcaatatga   1020
caaccaacca cagcttcatg tgtctcatca agtatggaca tttaagagtg aatcagacct   1080
tcaactggaa tacaaccaag caagagcatt tcctgataa cctgctccca tcctgggcca   1140
ttaccttaat ctcagtaaat ggaattttg tgatatgctg cctgacctac tgctttgccc    1200
caagatgcag agagaaagg aggaatgaga gattgagaag ggaaagtgta cgccctgtat    1260
aacagtgtcc gcagaagcaa ggggctgaaa agatctgaag gtcccacctc catttgcaat   1320
tgacctcttc tgggaacttc ctcagatgga caagattacc ccaccttgcc ctttacgtat    1380
ctgctcttag gtgcttcttc acttcagttg ctttgcagga agtgtctaga ggaatatggt   1440
gggcacagaa gtagctctgg tgaccttgat caaggtgttt tgaaatgcag aattcttgag   1500
ttctggaagg gactttagag aataccagtg ttattaatga caaaggcact gaggcccagg   1560
gaggtgaccc gaattataaa ggccagcgcc agaacccaga tttcctaact ctggtgctct   1620
ttcccttttat cagtttgact gtggcctgtt aactggtata tacatatata tgtcaggcaa   1680
agtgctgctg gaagtagaat tgtccaata acaggtcaac ttcagagact atctgatttc    1740
ctaatgtcag agtagaagat tttatgctgc tgttacaaa agcccaatgt aatgcatagg    1800
aagtatggca tgaacatctt taggagacta atggaaatat tattggtgtt tacccagtat   1860
tccattttt tcattgtgtt ctctattgct gctctctcac tcccccatga ggtacagcag    1920
aaaggagaac tatccaaaac taatttcctc tgacatgtaa gacgaatgat ttaggtacgt    1980
caaagcagta gtcaaggagg aaagggatag tccaaagact taactggttc atattggact   2040
gataatctct ttaaatggct ttatgctagt ttgacctcat ttgtaaaata tttatgagaa    2100
agttctcatt taaaatgaga tcgttgttta cagtgtatgt actaagcagt aagctatctt    2160
caaatgtcta aggtagtaac tttccatagg gcctccttag atccctaaga tggcttttc     2220
tccttggtat ttctgggtct ttctgacatc agcagagaac tggaaagaca tagccaactg    2280
ctgttcatgt tactcatgac tccttttctct aaaactgcct tccacaattc actagaccag   2340
aagtggacgc aacttaagct gggataatca cattatcatc tgaaaatctg gagttgaaca    2400
gcaaaagaag acaacatttc tcaaatgcac atctcatggc agctaagcca catggctggg    2460
atttaaagcc tttagagcca gcccatggct ttagctacct cactatgctg cttcacaaac    2520
cttgctcctg tgtaaaacta tattctcagt gtagggcaga gaggtctaac accaacataa    2580
ggtactagca gtgtttcccg tattgacagg aatacttaac tcaataattc ttttcttttc    2640
catttagtaa cagttgtgat gactatgttt ctattctaag taattcctgt attctacagc    2700
agatactttg tcagcaatac taagggaaga aacaaagttg aaccgtttct ttaataa       2757
```

<210> SEQ ID NO 6
<211> LENGTH: 288
<212> TYPE: PRT
<213> ORGANISM: Homo sapiens

<400> SEQUENCE: 6

Met Gly His Thr Arg Arg Gln Gly Thr Ser Pro Ser Lys Cys Pro Tyr

```
1               5                    10                   15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
            130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
                195                 200                 205

Thr Thr Asn His Ser Phe Met Cys Leu Ile Lys Tyr Gly His Leu Arg
        210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
                275                 280                 285
```

METHODS FOR TREATING CANCER IN PATIENTS WITH ELEVATED LEVELS OF BIM

CROSS-REFERENCE TO RELATED APPLICATIONS

This application is a National Stage application under 35 U.S.C. § 371 of International Application No. PCT/US2014/053870, having an International Filing Date of Sep. 3, 2014, which claims benefit of priority from U.S. Provisional Application Ser. No. 61/885,218, filed Oct. 1, 2013. The disclosures of each of the prior applications are considered part of the disclosure of this application, and are each incorporated in their entireties into this application.

TECHNICAL FIELD

This document relates to materials and methods for treating cancer, and more particularly to materials and methods for treating cancer in patients identified as having elevated levels of Bim.

BACKGROUND

The metastatic spread of tumor cells is the primary cause of cancer related mortality, indicating a need for therapeutic approaches capable of controlling or preventing metastasis (Gibbons et al. (2012) *OncoImmunology* 1(7):1061-1073; and Grivennikov et al. (2010) *Cell* 140:883-899). The presence of tumor-infiltrating effector and memory T cells is correlated with decreased metastatic spread, consistent with a role for T cells in preventing metastasis of primary tumors.

B7-H1 (also referred to as PD-L1) is a polypeptide expressed by a variety of tumor cells. It also is constitutively expressed by macrophages and dendritic cells, and its expression is up-regulated upon cell activation. PD-1 is expressed on the surface of activated T cells, B cells, and macrophages, and is a receptor for B7-H1. CD80 is found on activated B cells and monocytes, and provides a costimulatory signal necessary for T cell activation and survival; CD80 also binds B7-H1.

SUMMARY

This document provides, inter alia, a method for determining whether PD-1 on T cells has engaged its ligand, B7-H1. The method is based in part on the discovery that engagement of PD-1 by B7-H1 results in up-regulation of Bim, a pro-apoptotic molecule, and is correlated with B7-H1-mediated T cell death. This discovery suggests that intracellular levels of Bim among PD-1 positive cells is a barometer of the extent to which PD-1 has been triggered by B7-H1, with lower levels of Bim identifying activated PD-1 positive T cells whose PD-1 molecules have not yet been extensively engaged, and higher levels of Bim reflecting chronic engagement of PD-1 with B7-H1. Stratifying Bim levels among PD-1 positive CD8 T cells may be a biomarker for gauging (1) whether PD-1 molecules on CD8 T cells have been engaged by B7-H1 tumor associated ligands; and (2) the efficacy of an anti-PD-1 or anti-B7-H1 blockade regimen in reducing PD-1 engagement. Thus, using Bim as a signaling biomarker for PD-1 function, it may be possible to select patients more likely to benefit from checkpoint blockade therapy and to identify optimal therapeutic timing and dosing schedules.

In one aspect, this document features a method for treating a mammal having cancer, wherein said method comprises: (a) identifying said mammal as containing an elevated level of Bim, and (b) administering to said mammal an anti-B7-H1 antibody, an anti-PD-1 antibody, an anti-CD80 antibody, a fusion protein comprising a portion of PD-1 linked to an immunoglobulin Fc sequence, or a fusion protein comprising a portion of CD80 linked to an Ig Fc sequence, under conditions wherein the interaction of naturally-occurring B7-H1 with PD-1 or CD80 in said mammal is reduced after said administering. The mammal can be a human. The elevated level of Bim can be based on Bim protein levels, or on Bcl2l11 mRNA levels. The cancer can be a melanoma cancer, a breast cancer, a lung cancer, a renal cell carcinoma cancer, a pancreas cancer, a prostate cancer, a colon cancer, a brain cancer, a liver cancer, or an ovarian cancer.

In another aspect, this document features a method for treating cancer, wherein said method comprises administering an anti-B7-H1 antibody, an anti-PD-1 antibody, an anti-CD80 antibody, a fusion protein comprising a portion of PD-1 linked to an immunoglobulin Fc sequence, or a fusion protein comprising a portion of CD80 linked to an immunoglobulin Fc sequence to a mammal identified as containing an elevated level of Bim, wherein said antibody or fusion protein is administered under conditions wherein the interaction of naturally-occurring B7-H1 with PD-1 or CD80 in said mammal is reduced after said administering. The mammal can be a human. The elevated level of Bim can be based on Bim protein levels, or on Bcl2l11 mRNA levels. The cancer can be a melanoma cancer, a breast cancer, a lung cancer, a renal cell carcinoma cancer, a pancreas cancer, a prostate cancer, a colon cancer, a brain cancer, a liver cancer, or an ovarian cancer.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A, FACS scans showing the percentage of OVA-specific tetramer+ CD8+ T cells; *p<0.05 compared with WT mice. FIG. 2B graph plotting the absolute number of OVA-specific tetramer+ CD8+ T cells (mean±SD, n=3). FIG. 2C, FACS analysis of intracellular production of cytokines in CD8+ T cells from immunized mice (mean±SD, n=3). FIG. 2D, graphs plotting in vivo cytolytic activity in immunized mice. OVA-peptide or control-peptide pulsed target cells (syngeneic splenocytes) were labeled with high or low dose CFSE (5 μM for OVA-peptide pulsed cells; 0.5 μM for control-peptide pulsed cells) and mixed (1:1, 2.5×106 of each) and injected i.v. into WT or B7-H1-deficient mice. Histogram plots (left) show the percentage of remaining target cells in the spleen 4 hours after target cell transfer. Bar graph (right) shows percentage of specific lysis in the spleen (mean±SD, n=3).

FIG. 3A, percentage and absolute numbers of IFNγ+ CD8+ T cells in the lung of immunized mice (mean±SD, n=3) on day 4 after tumor injection. *p<0.01 compared with WT mice. FIG. 3B, metastatic tumor foci in the lung tissue were identified and counted on day 20 after tumor injection (mean±SD, n=5). N.S.: not significant.

FIG. 4A, FACS scans showing the percentage of CD11a$^{high}$ CD8+ T cells from WT and B7-H1-deficient immunized mice. FIG. 4B, graph plotting average percentage of CD11a$^{high}$ CD8+ T cells from WT and B7-H1-deficient immunized mice (mean±SD, n=4). FIG. 4C, FACS scans showing the percentage of antigen-specific tetramer+ (K$^b$/OVA-tet) cells in CD11a$^{high}$ and CD11a$^{low}$ CD8+ T-cell population. FIG. 4D, FACS scans showing CTL functional assay of CD11$^{high}$ and CD11a$^{low}$ CD8+ T cells after a brief re-stimulation in vitro. Degranulation of CTLs was analyzed by CD107a mobilization, followed by intracellular staining for IFNγ. Numbers indicate percentages of gated areas.

FIGS. 5A and 5B, FACS scans showing Ki67 expression and BrdU incorporation, respectively, analyzed in CD11a$^{high}$ or CD11a$^{low}$ CD8+ T cells. Numbers are percentages of gated area in total CD8+ T cells. FIG. 5C, FACS scans of TMRE$^{low}$ Annexin V+ apoptotic cells measured in CD11a$^{high}$ and CD11a$^{low}$ CD8+ T cells. FIG. 5D, graph plotting the percentage of apoptotic cells (TMRE$^{low}$ Annexin V+) in CD11a$^{high}$ CD8+ T cells (mean±SD, n=4).

FIG. 6A, flow cytometry assay of the intracellular expression of Bim, Bcl-2 and Bcl-xL in gated CD11a$^{high}$ CD8+ T cells in the spleen of WT (red) and B7-H1-deficient (blue) mice on day 7 after immunization. Numbers are mean fluorescence intensity (MFI) of Bim expression. FIG. 6B, graph showing average MFI of Bim expressed by CD11a$^{high}$ CD8+ T cells (mean±SD, n=9). FIG. 6C, intracellular expression of Bim in CD11a$^{high}$ CD8+ T cells in the liver of immunized mice. Numbers are MFI. FIG. 6D, Bim expression in total CD8+ T cells in the spleen of naïve WT (red) and B7-H1-deficient (blue) mice.

FIG. 8A, Western blot showing Bim isoform expression in CD8+ T cells. FIG. 8B, histogram showing expression of total Bim in CD8+ T cells co-stimulated with B7-H1 (blue) or control protein (red). Numbers are MFI. FIG. 8C, graph plotting average MFI of Bim expressed by activated CD8+ T cells (mean±SD, n=5). FIG. 8D, graph plotting the percentage of live (trypan blue exclusive) CD8+ T cells in culture (mean±SD, n=5). FIG. 8E, FACS scans indicating apoptosis of CD8+ T cells isolated from WT, Bim-deficient, and Bcl-2 transgenic (Tg) mice. Numbers show percentage of TMRE$^{low}$ Annexin V+ apoptotic T cells in total CD8+ T cells. FIG. 8F, graph plotting average MFI of Bim expressed by CD8+ T cells in culture with anti-B7-H1 Ab (10B5, blocking B7-H1 binding to both PD-1 and CD80; 43H12, blocking B7-H1 binding to CD80 only), anti-PD-1 Ab (G4), or control Ab (10 μg/mL of each) (mean±SD, n=3).

FIG. 9A, graph plotting analysis of Bcl2l11 transcript levels by real-time qPCR using the comparative CT method. GAPDH served as the internal control gene. Graph shows fold change (mean±SD, n=4). FIG. 9B, histograms plotting phosphorylation of Akt (left) and mTOR (right), analyzed by intracellular staining of CD8+ T cells with anti-phospho-Akt and anti-phospho-mTOR Abs. Numbers show percentage of positive stained cells. FIG. 9C, bar graph plotting average MFI of phospho-Akt and phospho-mTOR expression (mean±SD, n=3). N.S.: not significant.

FIG. 10 contains representative nucleic acid (top) and amino acid (bottom) sequences for human B7-H1 (SEQ ID NOS:1 and 2, respectively).

FIG. 11 contains representative nucleic acid (top) and amino acid (bottom) sequences for human PD-1 (SEQ ID NOS:3 and 4, respectively).

FIGS. 12A and 12B contain representative nucleic acid (12A) and amino acid (12B) sequences for human CD80 (SEQ ID NOS:5 and 6, respectively).

FIG. 13 also contains a histogram plotting expression of Bim by subsets of CD8+ T cells (Tn: T naïve cells; PD-1−, PD-1 negative primed cells; PD-1+, PD-1 positive primed cells). Only the PD-1+ primed cells CD8+ T cells expressed high levels of Bim.

Figure 14:
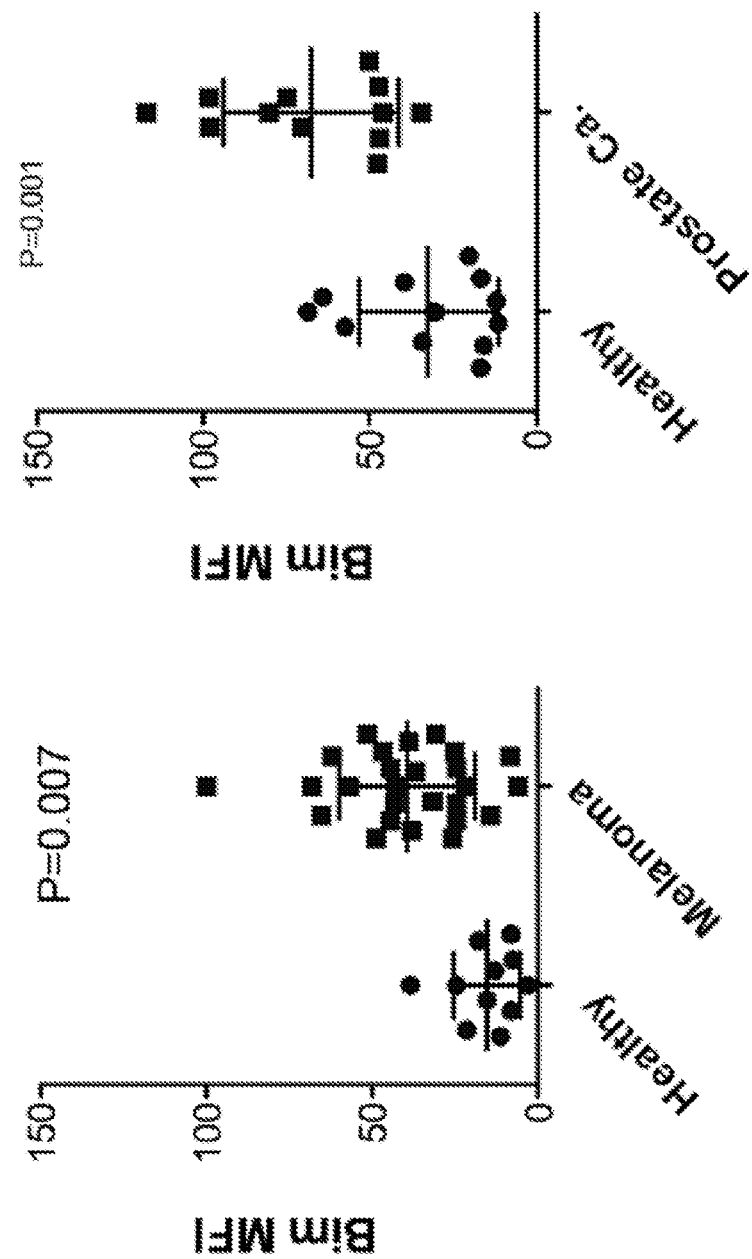

FIG. 14 is a pair of graphs plotting the level of Bim expression in tumor-reactive PD-1+ CD11a$^{high}$ CD8+ T cells in the peripheral blood of 26 melanoma patients as compared to 11 normal, healthy controls (left panel, P=0.007 by unpaired Student T test), and in tumor-reactive PD-1+ CD11a$^{high}$ CD8+ T cells in the peripheral blood of 11 prostate cancer patients as compared to 11 normal, healthy controls (right panel, P=0.001 by unpaired Student T test).

Figure 15:
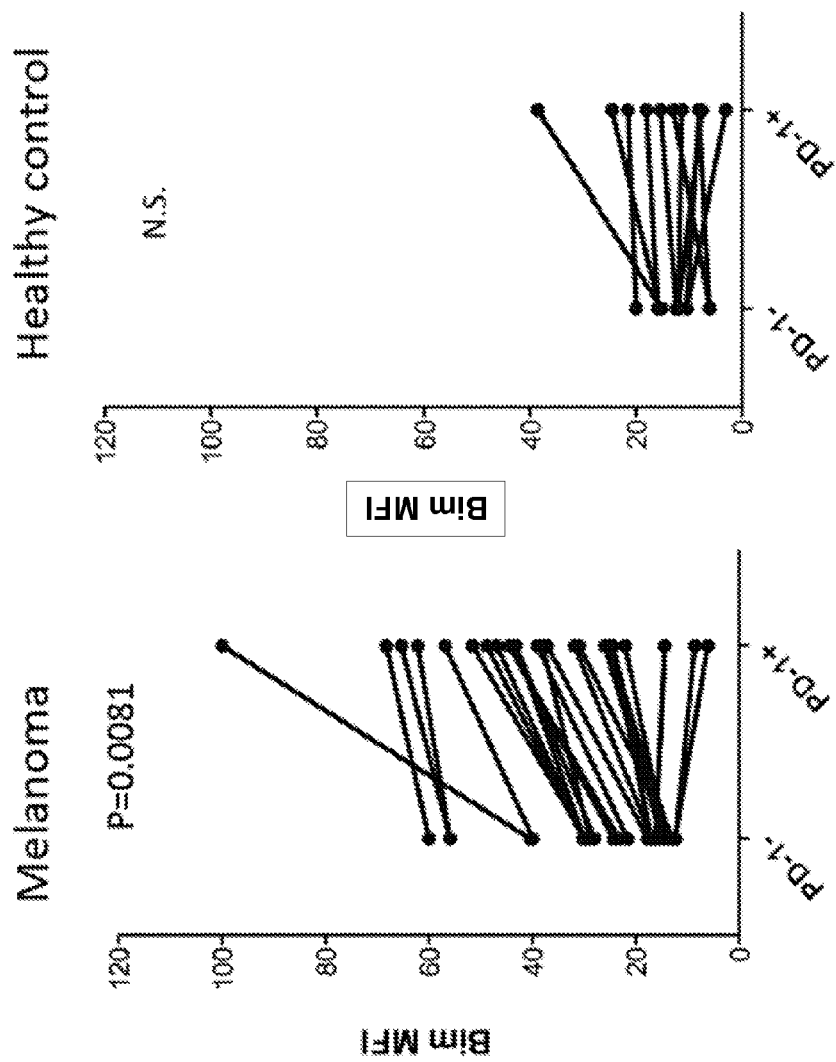

FIG. 15 is a pair of graphs plotting Bim expression in PD-1 negative (PD-1−) and PD-1 positive (PD-1+) CD11a$^{high}$ CD8+ T cells from melanoma patients (left) and healthy controls (right). Bim was significantly increased in the PD-1+ populations (p=0.0081) in melanoma patients.

Figure 16:
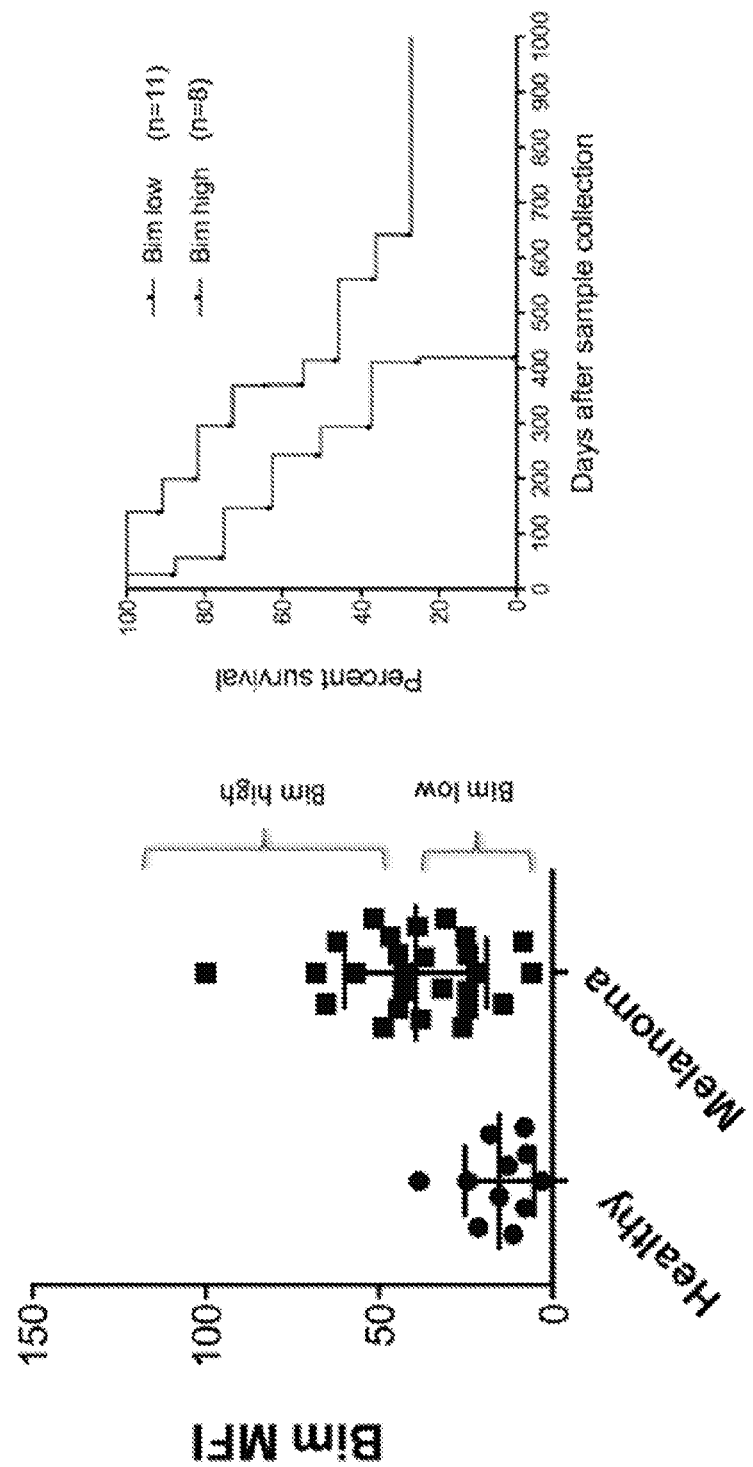

FIG. 16 is a pair of graphs plotting the level of Bim expression in tumor-reactive PD-1+CD11a$^{high}$ CD8+ T cells in the peripheral blood of 26 melanoma patients as compared to 11 normal, healthy controls (left panel, indicating "Bim low" and "Bim high" samples), and plotting the survival rate for "Bim low" vs. "Bim high" patients (right panel).

Figure 17B:

FIG. 17A is a pair of graphs showing that B7-H1 protein induced expression of Bim in human pre-activated CD8+ T cells. FIG. 17B is a picture of a Western blot showing Bim levels in the cells.

Figure 18:
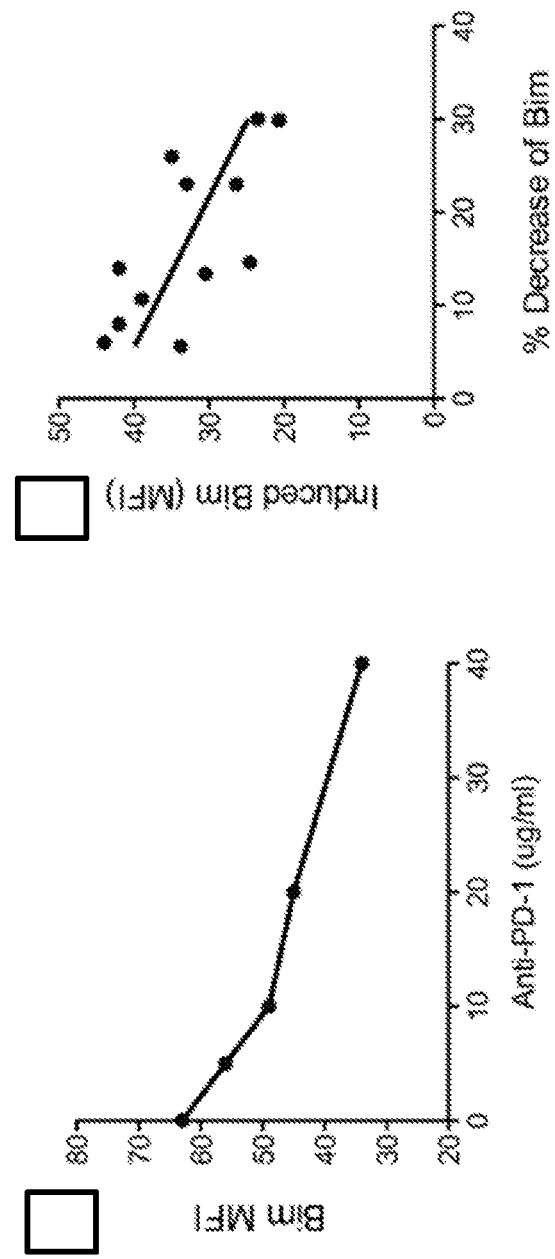

FIG. 18 is a pair of graphs showing that an anti-PD-1 antibody significantly blocked B7-H1-induced Bim up-regulation in a dose dependent fashion (left panel), and that the blocking effects of the anti-PD-1 antibody were inversely correlated with the higher levels of Bim induced by B7-H1 (right panel).

Figure 19:
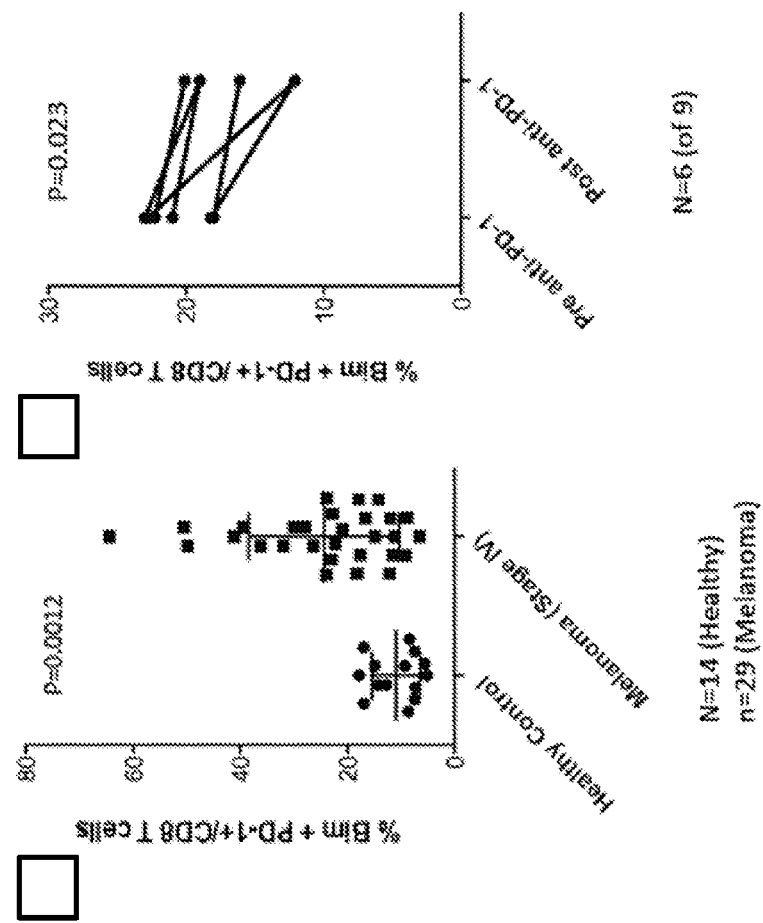

FIG. 19 is a pair of graphs showing that the frequency of Bim+PD-1+ CD8 T cells was significantly higher in the peripheral blood of melanoma patients before treatment than in a healthy control group (left panel), and that after anti-PD-1 antibody therapy, about 67% of the melanoma patients demonstrated a significant reduction in the frequency of Bim+PD-1+CD8 T cells (right panel).

Figure 20:
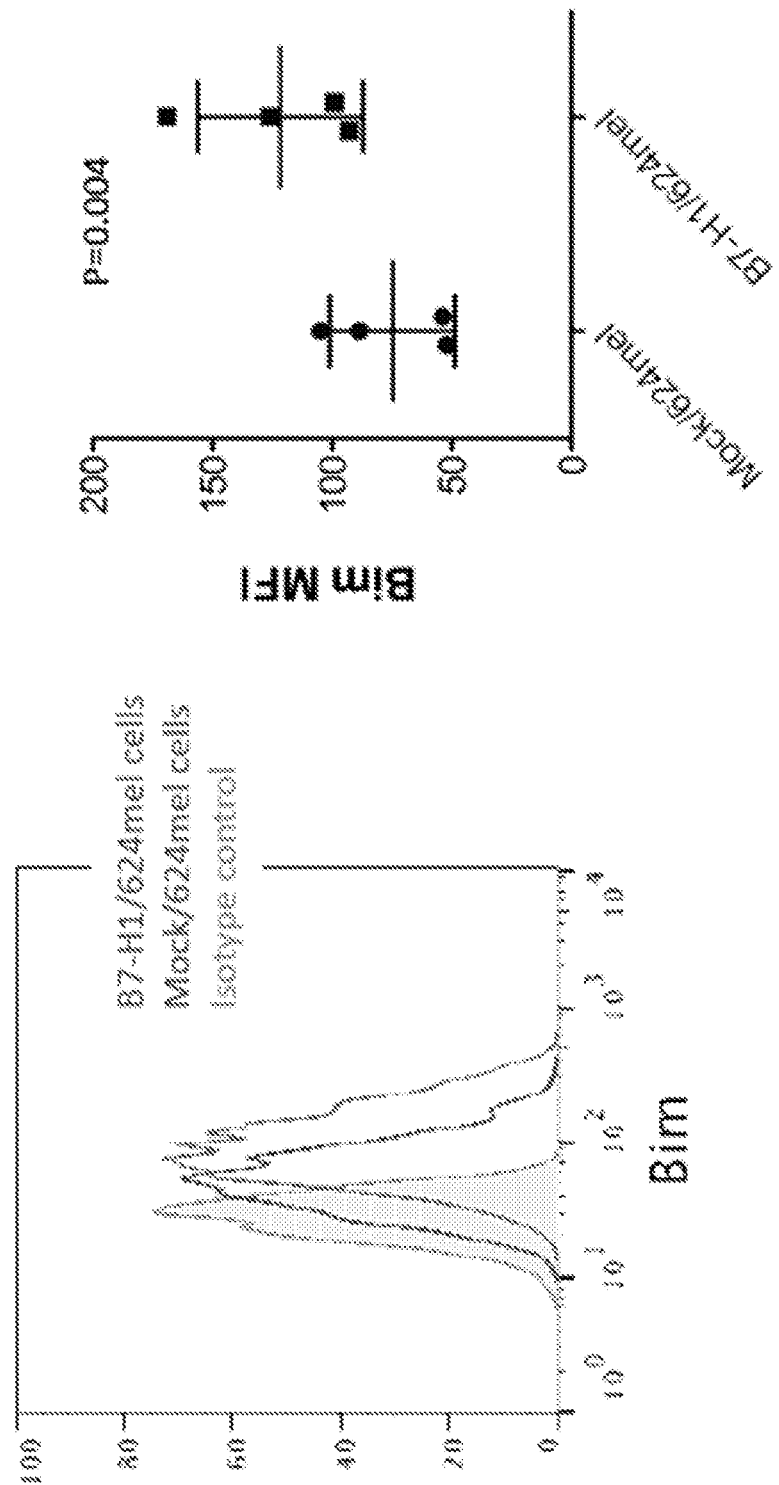

FIG. 20 is a pair of graphs showing that B7-H1 expressed by tumor cells induced Bim up-regulation in human pre-activated CD8 T cells.

Figure 21:
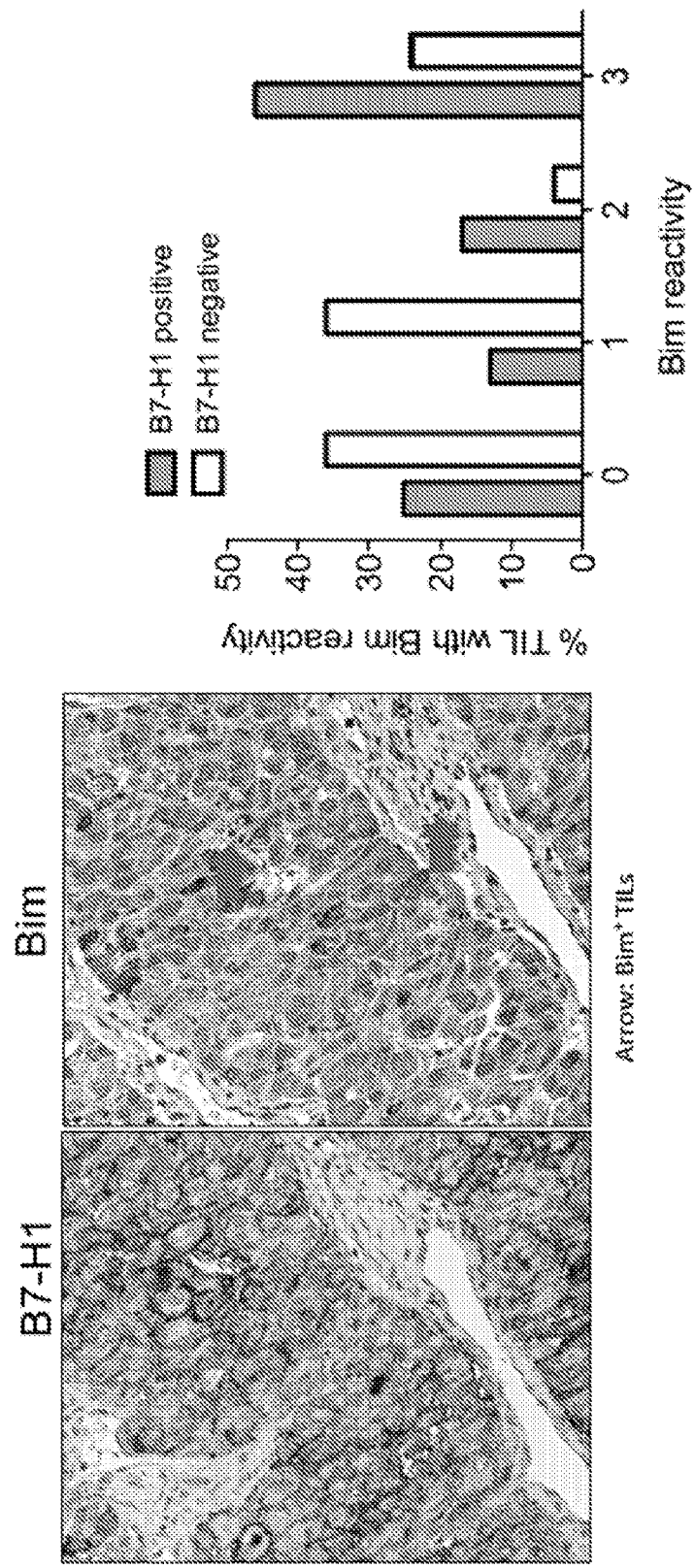

FIG. 21 is a pair of photographs (left) and a graph (right) showing that Bim expression was associated with B7-H1 expression in human renal cell carcinoma (RCC). In particular, the graph in the right panel shows that Bim+ tumor infiltrating lymphocytes (TILs) were increased in B7-H1 positive tumor tissues. Bim reactivity scores: 0, absence; 1, focal; 2, moderate; 3, marked. Contingency analysis using Fisher's exact test (p<0.01).

Figure 22:
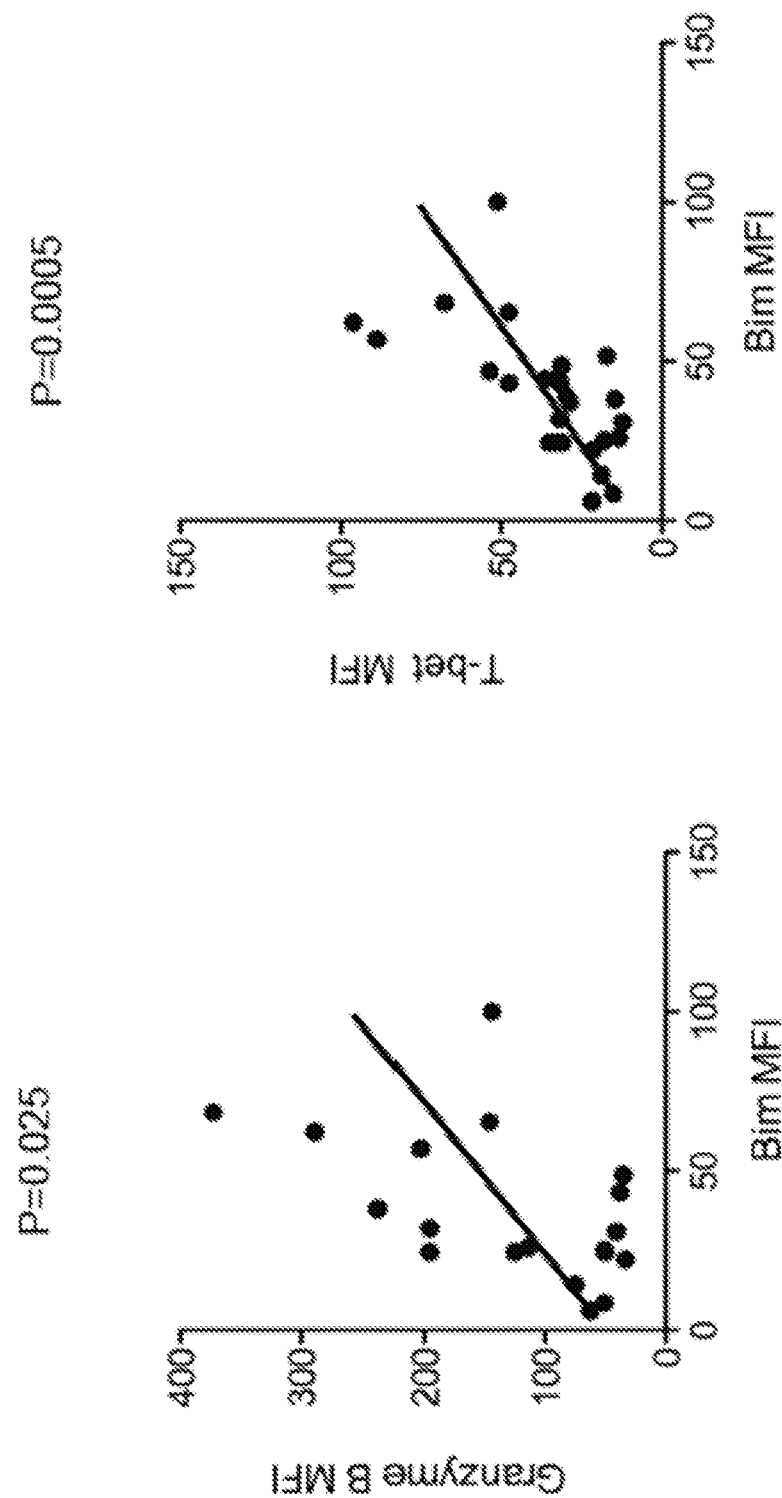

FIG. 22 is a pair of graphs showing that Bim expression was correlated with Granzyme B and T-bet (a transcription factor of effector T cells) expressed by cancer-related PD-1+ CD11a$^{high}$ CD8+ T cells, suggesting that Bim expression is associated with effector CD8+ T cell differentiation.

Figure 23:
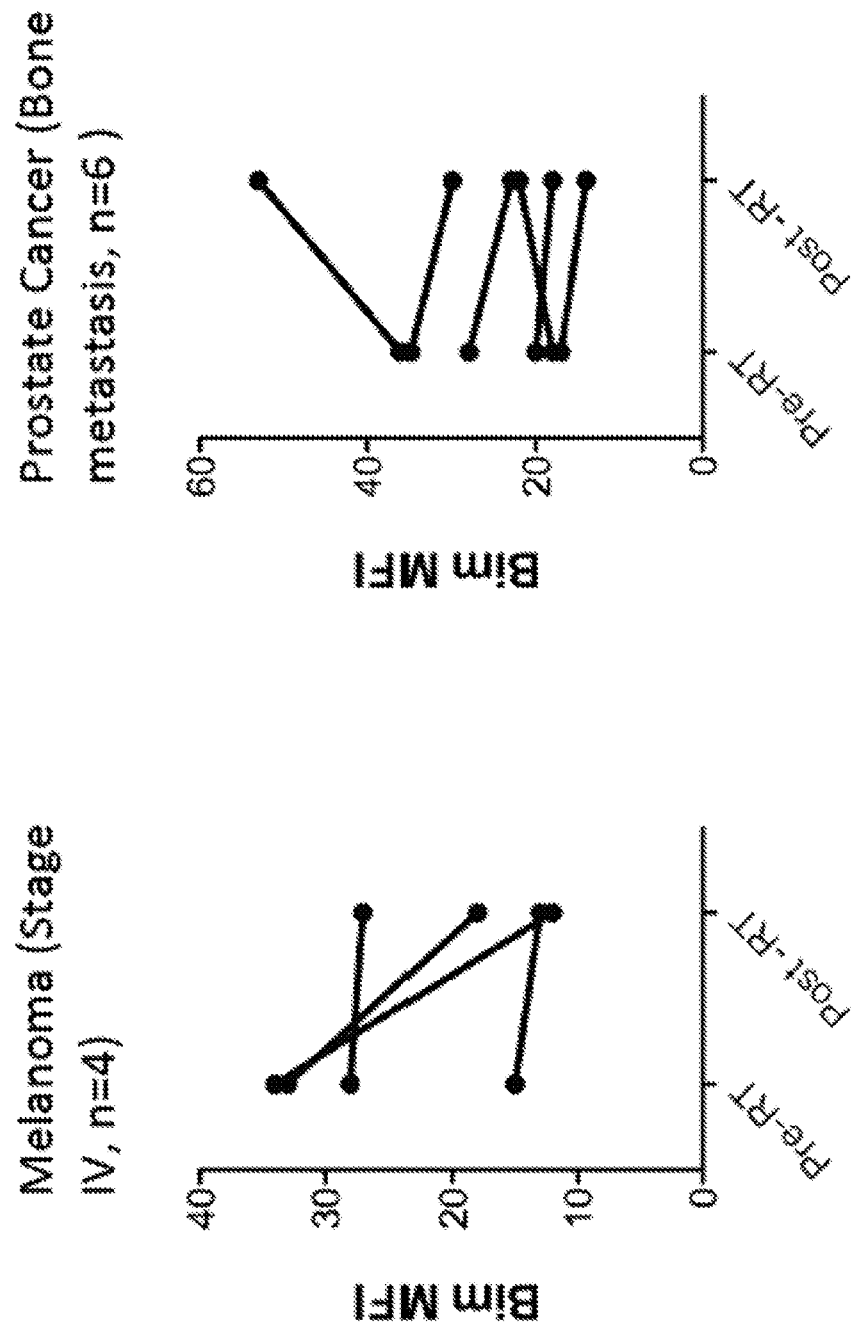

FIG. 23 is a pair of graphs showing that Bim expression declined in PD-1+ CD11a$^{high}$ CD8 T cells following radiotherapy in some melanoma (left panel) and prostate (right panel) cancer patients.

DETAILED DESCRIPTION

This document provides methods and materials for treating cancer. For example, this document provides methods and materials for identifying a mammal (e.g., a human) as having an elevated level of Bim, and treating the mammal with a molecule that can interfere with the interaction between B7-H1 and PD-1, and/or the interaction between B7-H1 and CD80 (e.g., an antibody against B7-H1, PD-1, or CD80, or with a fusion protein containing a portion of PD-1 or a portion of CD80 fused to an immunoglobulin (Ig) Fc domain). As described herein, elevated levels of Bim can be related to increased apoptosis of antigen-primed CD8+ T cells, but inhibiting the interaction of B7-H1 with PD-1 or CD80 can lead to reduced levels of Bim and reduced T cell apoptosis.

The term "elevated level" as used herein with respect to a level of Bim refers to a level that is greater (e.g., 50% greater, 2-fold greater, 3-fold greater, or more than 3-fold greater) than a reference level of Bim. The term "reference level" as used herein with respect to Bim refers to the level of Bim typically observed in healthy mammals without cancer. For example, a reference level of Bim can be the average level of Bim present in samples obtained from a random sampling of 50 humans free of cancer.

The presence of an elevated level of Bim can be determined by measuring, for example, protein levels or nucleic acid levels. For example, the level of Bim protein can be measured in a sample of blood (e.g., a peripheral blood sample) or another bodily fluid from a mammal with cancer or from a control mammal, using cell staining, western blotting, or other immunological techniques. The level of Bim expression also can be measured at the nucleic acid level, using Northern blotting, or any other method suitable for determining mRNA levels of Bcl2l11, which encodes the Bim protein. In some cases, Bim protein or nucleic acid levels can be measured in tumor tissue samples, ascites samples, or lymphoid organ samples. It will be appreciated that levels from comparable samples are used when determining whether or not a particular level is an elevated level.

A representative example of a human B7-H1 nucleic acid has the sequence set forth in GENBANK® Accession No. AF177937 (GI No. 6708118) (SEQ ID NO:1; FIG. 10), and a representative human B7-H1 polypeptide has the sequence set forth in GENBANK® Accession No. AAF25807 (GI No. 6708119) (SEQ ID NO:2; FIG. 10).

A representative example of a human PD-1 nucleic acid can have the sequence set forth in GENBANK® Accession No. BC074740.2 (GI No. 50960296) (SEQ ID NO:3; FIG. 11), and representative example of a human PD-1 polypeptide has the sequence set forth in GENBANK® Accession No. AAH74740.1 (GI No. 49902307) (SEQ ID NO:4; FIG. 11).

A representative example of a human CD80 nucleic acid has the sequence set forth in NCBI Reference No. NM_005191.3 (GI No. 113722122) (SEQ ID NO:5; FIG. 12A), and a representative example of a human CD80 polypeptide has the sequence set forth in NCBI Reference No. NP_005182.1 (GI No. 4885123) (SEQ ID NO:6; FIG. 12B).

Once the level of Bim within a sample from a mammal is determined, the level can be compared to a reference level and used to classify the mammal as having or lacking an elevated level of Bim.

Once a mammal has been identified as having an elevated level of Bim as described herein, the mammal can be administered a molecule that inhibits the interaction between B7-H1 and PD-1 and/or the interaction between B7-H1 and CD80. Examples of such molecules include, without limitation, antibodies (e.g., anti-B7-H1 antibodies, anti-PD-1 antibodies, or anti-CD80 antibodies), and fusion proteins (e.g., PD-1 fusion proteins or CD80 fusion proteins). Such fusion proteins can contain, for example, the extracellular domain of PD-1 fused to an IgG Fc domain, or the extracellular domain of CD80 fused to an IgG Fc domain. After administration, the antibody/ies or fusion protein(s) can bind B7-H1, thus reducing or blocking B7-H1's action in inducing Bim up regulation.

The term "antibody" includes monoclonal antibodies, polyclonal antibodies, recombinant antibodies, humanized antibodies (Jones et al. (1986) *Nature* 321:522-525; Riechmann et al. (1988) *Nature* 332:323-329; and Presta (1992) *Curr. Op. Struct. Biol.* 2:593-596), chimeric antibodies (Morrison et al. (1984) *Proc. Natl. Acad. Sci. USA* 81:6851-6855), multispecific antibodies (e.g., bispecific antibodies) formed from at least two antibodies, and antibody fragments. The term "antibody fragment" comprises any portion of the afore-mentioned antibodies, such as their antigen binding or variable regions. Examples of antibody fragments include Fab fragments, Fab' fragments, F(ab')2 fragments, Fv fragments, diabodies (Hollinger et al. (1993) *Proc. Natl. Acad. Sci. USA* 90:6444-6448), single chain antibody molecules (Plückthun in: *The Pharmacology of Monoclonal Antibodies* 113, Rosenburg and Moore, eds., Springer Verlag, N.Y. (1994), 269-315) and other fragments as long as they exhibit the desired capability of binding to B7-H1, PD-1, or CD80.

Examples of anti-human B7-H1 antibodies include, without limitation, anti-human B7-H1 antibodies commercially available from Biolegend (e.g., Catalog No. 329701 or 329702; San Diego, Calif.) or eBioscience (e.g., Catalog No. 14-5983-80 or 14-5983-82).

Examples of anti-human PD-1 antibodies include, without limitation, anti-human PD-1 antibodies commercially available from Biolegend (e.g., Catalog No. 329904 or 329905) or eBioscience (Catalog No. 12-2799-42; San Diego, Calif.).

Examples of anti-human CD80 antibodies include, without limitation, anti-human CD8 antibodies commercially available from Biolegend (e.g., Catalog No. 305201 or 305202) or eBioscience (e.g., Catalog No. 14-0809-80 or 14-0809-82).

The term "antibody," as used herein, also includes antibody-like molecules that contain engineered sub-domains of antibodies or naturally occurring antibody variants. These antibody-like molecules may be single-domain antibodies such as $V_H$-only or $V_L$-only domains derived either from natural sources such as camelids (Muyldermans et al. (2001) *Rev. Mol. Biotechnol.* 74:277-302) or through in vitro display of libraries from humans, camelids or other species (Holt et al. (2003) *Trends Biotechnol.* 21:484-90). In certain embodiments, the polypeptide structure of the antigen binding proteins can be based on antibodies, including, but not limited to, minibodies, synthetic antibodies (sometimes referred to as "antibody mimetics"), human antibodies, antibody fusions (sometimes referred to as "antibody conjugates"), and fragments thereof, respectively.

An "Fv fragment" is the minimum antibody fragment that contains a complete antigen-recognition and -binding site. This region consists of a dimer of one heavy chain variable domain and one light chain variable domain in tight, non-covalent association. It is in this configuration that the three CDR's of each variable domain interact to define an antigen-binding site on the surface of the VH-VL dimer. Collectively, the six CDR's confer antigen-binding specificity to the antibody. However, even a single variable domain (or half of an Fv comprising only three CDR's specific for an antigen) has the ability to recognize and bind the antigen, although usually at a lower affinity than the entire binding site. The "Fab fragment" also contains the constant domain of the light chain and the first constant domain ($C_H1$) of the heavy chain. The "Fab fragment" differs from the "Fab' fragment" by the addition of a few residues at the carboxy terminus of the heavy chain $C_H1$ domain, including one or more cysteines from the antibody hinge region. The "F(ab')2 fragment" originally is produced as a pair of "Fab' fragments" which have hinge cysteines between them. Methods of preparing such antibody fragments, such as papain or pepsin digestion, are known to those skilled in the art.

An antibody can be of the IgA-, IgD-, IgE, IgG- or IgM-type, including IgG- or IgM-types such as, without limitation, IgG1-, IgG2-, IgG3-, IgG4-, IgM1- and IgM2-types. For example, in some cases, the antibody is of the IgG1-, IgG2- or IgG4-type.

In some embodiments, antibodies as used in the methods described herein can be fully human or humanized antibodies. Human antibodies can avoid certain problems associated with xenogeneic antibodies, such as antibodies that possess murine or rat variable and/or constant regions. First, because the effector portion is human, it can interact better with other parts of the human immune system, e.g., to destroy target cells more efficiently by complement-dependent cytotoxicity or antibody-dependent cellular cytotoxicity. Second, the human immune system should not recognize the antibody as foreign. Third, half-life in human circulation will be similar to naturally occurring human antibodies, allowing smaller and less frequent doses to be given. Methods for preparing human antibodies are known in the art.

In addition to human antibodies, "humanized" antibodies can have many advantages. Humanized antibodies generally are chimeric or mutant monoclonal antibodies from mouse, rat, hamster, rabbit or other species, bearing human constant and/or variable region domains or specific changes. Techniques for generating humanized antibodies are well known to those of skill in the art. For example, controlled rearrangement of antibody domains joined through protein disulfide bonds to form new, artificial protein molecules or "chimeric" antibodies can be utilized (Konieczny et al. (1981) *Haematologia (Budap.)* 14:95). Recombinant DNA technology can be used to construct gene fusions between DNA sequences encoding mouse antibody variable light and heavy chain domains and human antibody light and heavy chain constant domains (Morrison et al. (1984) *Proc. Natl. Acad. Sci. USA* 81:6851).

DNA sequences encoding antigen binding portions or complementarity determining regions (CDR's) of murine monoclonal antibodies can be grafted by molecular means into DNA sequences encoding frameworks of human antibody heavy and light chains (Jones et al. (1986) *Nature* 321:522; Riechmann et al. (1988) *Nature* 332:323). Expressed recombinant products are called "reshaped" or humanized antibodies, and comprise the framework of a human antibody light or heavy chain and antigen recognition portions, CDR's, of a murine monoclonal antibody.

Other methods for designing heavy and light chains and for producing humanized antibodies are described in, for example, U.S. Pat. Nos. 5,530,101; 5,565,332; 5,585,089; 5,639,641; 5,693,761; 5,693,762; and 5,733,743. Yet additional methods for humanizing antibodies are described in U.S. Pat. Nos. 4,816,567; 4,935,496; 5,502,167; 5,558,864; 5,693,493; 5,698,417; 5,705,154; 5,750,078; and 5,770,403, for example.

Molecules that interfere with the interaction between B7-H1 and PD-1, and/or the interaction between B7-H1 and CD80, as described herein (e.g., antibodies against B7-H1, PD-1, and CD80, as well as fusion proteins containing portions of PD-1 or CD80 linked to an Ig Fc domain), can be incorporated into pharmaceutical compositions for treatment of cancer. Thus, this document also provides the use of such molecules in the manufacture of medicaments for treating cancer. The compositions can further include one or more pharmaceutically acceptable carriers, diluents and/or adjuvants. The potency of the pharmaceutical compositions provided herein typically is based on the binding of the antibody or fusion protein to B7-H1.

A "pharmaceutically acceptable carrier" (also referred to as an "excipient" or a "carrier") is a pharmaceutically acceptable solvent, suspending agent, stabilizing agent, or any other pharmacologically inert vehicle for delivering one or more therapeutic compounds to a subject, which is nontoxic to the cell or mammal being exposed thereto at the dosages and concentrations employed. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids include, by way of example and not limitation: water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Pharmaceutically acceptable carriers also include aqueous pH buffered solutions or liposomes (small vesicles composed of various types of lipids, phospholipids and/or surfactants which are useful for delivery of a drug to a mammal). Further examples of pharmaceutically acceptable carriers include buffers such as phosphate, citrate, and other organic acids, antioxidants such as ascorbic acid, low molecular weight (less than about 10 residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Pharmaceutical compositions can be formulated by mixing one or more active agents with one or more physiologically acceptable carriers, diluents, and/or adjuvants, and optionally other agents that are usually incorporated into formulations to provide improved transfer, delivery, tolerance, and the like. A pharmaceutical composition can be formulated, e.g., in lyophilized formulations, aqueous solutions, dispersions, or solid preparations, such as tablets, dragees or capsules. A multitude of appropriate formulations can be found in the formulary known to all pharmaceutical chemists: *Remington's Pharmaceutical Sciences* (18th ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies as described herein, provided that the active agent in the formulation is not inactivated by the formulation and the formulation is physiologically compatible and tolerable with the route of administration. See, also, Baldrick (2000) *Regul. Toxicol. Pharmacol.* 32:210-218; Wang (2000) *Int. J. Pharm.* 203: 1-60; Charman (2000) *J. Pharm. Sci.* 89:967-978; and Powell et al. (1998) *PDA J. Pharm. Sci. Technol.* 52:238-311), and the citations therein for additional information related to formulations, excipients and carriers well known to pharmaceutical chemists.

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Compositions and formulations can include sterile aqueous solutions, which also can contain buffers, diluents and other suitable additives (e.g., penetration enhancers, carrier compounds and other pharmaceutically acceptable carriers). Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

In some embodiments, a composition containing an antibody or fusion protein as provided herein (e.g., an anti-B7-H7, anti-PD-1, or anti-CD80 antibody, or a PD-1 FC or CD80 Fc fusion protein) can be in the form of a solution or powder with or without a diluent to make an injectable suspension. The composition may contain additional ingredients including, without limitation, pharmaceutically acceptable vehicles, such as saline, water, lactic acid, mannitol, or combinations thereof, for example.

Any appropriate method can be used to administer a molecule as described herein to a mammal. Administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral. In addition, a composition containing an antibody or fusion protein as described herein can be administered prior to, after, or in lieu of surgical resection of a tumor.

A composition containing an antibody (e.g., an anti-B7-H1 antibody, anti-PD-1 antibody, or anti-CD80 antibody) or a fusion protein (e.g., a PD-1 Fc fusion or a CD80 Fc fusion) can be administered to a mammal in any appropriate amount, at any appropriate frequency, and for any appropriate duration effective to achieve a desired outcome (e.g., to increase progression-free survival). In some cases, a composition containing an antibody or fusion protein as described herein can be administered to a mammal having cancer to reduce the progression rate of the cancer by 5, 10, 25, 50, 75, 100, or more percent. For example, the progression rate can be reduced such that no additional cancer progression is detected. Any appropriate method can be used to determine whether or not the progression rate of cancer is reduced. For skin cancer (e.g., melanoma), for example, the progression rate can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer after treatment can be determined and compared to the stage before treatment to determine whether or not the progression rate has been reduced.

In some cases, a composition containing an antibody or a fusion protein as described herein can be administered to a mammal having cancer under conditions where progression-free survival is increased (e.g., by 5, 10, 25, 50, 75, 100, or more percent) as compared to the median progression-free survival of corresponding mammals having untreated cancer or the median progression-free survival of corresponding mammals having cancer and treated with other therapies (e.g., chemotherapeutic agents). Progression-free survival can be measured over any length of time (e.g., one month, two months, three months, four months, five months, six months, or longer).

Administration to a mammal of a molecule as set forth herein can result in increased numbers of naturally-occurring tumor-reactive CD8+ T cells, which can exert anti-cancer effects against cancer cells present within the mammal.

An effective amount of a composition containing a molecule as provided herein can be any amount that reduces the progression rate of cancer, increases the progression-free survival rate, or increases the median time to progression without producing significant toxicity to the mammal. Optimum dosages can vary depending on the relative potency of individual polypeptides (e.g., antibodies and fusion proteins), and can generally be estimated based on $EC_{50}$ found to be effective in in vitro and in vivo animal models. Typically, dosage is from 0.01 μg to 100 g per kg of body weight. For example, an effective amount of an antibody or fusion protein can be from about 1 mg/kg to about 100 mg/kg (e.g., about 5 mg/kg, about 10 mg/kg, about 20 mg/kg, about 50 mg/kg, or about 75 mg/kg). If a particular mammal fails to respond to a particular amount, then the amount of the antibody or fusion protein can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer may require an increase or decrease in the actual effective amount administered.

The frequency of administration can be any frequency that reduces the progression rate of cancer, increases the progression-free survival rate, or increases the median time to progression without producing significant toxicity to the mammal. For example, the frequency of administration can be once or more daily, biweekly, weekly, monthly, or even less. The frequency of administration can remain constant or can be variable during the duration of treatment. A course of treatment can include rest periods. For example, a composition containing an antibody or fusion protein as provided herein can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition provided herein can be any duration that reduces the progression rate of cancer, increases the progression-free survival rate, or increases the median time to progression without producing significant toxicity to the mammal. Thus, the effective duration can vary from several days to several weeks, months, or years. In general, the effective duration for the treatment of cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer.

After administering a composition provided herein to a mammal, the mammal can be monitored to determine whether or not the cancer was treated. For example, a mammal can be assessed after treatment to determine whether or not the progression rate of the cancer has been reduced (e.g., stopped). Any method, including those that are standard in the art, can be used to assess progression and survival rates.

The invention will be further described in the following examples, which do not limit the scope of the invention described in the claims.

EXAMPLES

Example 1—Materials and Methods

Mice, Cell Lines and Reagents:

Female CD45.2+C57BL/6 mice were purchased from Taconic Farms and CD45.1+ congenic C57BL/6-Ly5.1 mice were purchased from National Cancer Institute. OT-1 TCR (Thy 1.1+) transgenic mice were provided by T. Tian (Harvard University, Boston, Mass.). B7-H1-deficient C57BL/6 mice were provided by L. Chen (Yale University, New Haven, Conn.; Dong et al., Immunity 20:327-336, 2004). Bcl2l11−/− mice and Cd80−/− mice were purchased from Jackson Laboratory. Cd80−/− mice were crossbred into WT OT-1 mice and produced Cd80−/− OT-1 mice. Bcl-2 transgenic mice were provided by V. Shapiro (Mayo Clinic, Rochester). Mice were maintained under pathogen-free conditions and used at 8-12 weeks of age. B16-OVA murine melanoma cells were provided by R. Vile (Mayo Clinic, Rochester, Minn.), and were cultured in RPMI 1640 medium (Cellgro) with 10% FBS (Life Technologies), 1 U/mL penicillin, 1 µg/mL streptomycin and 20 mM HEPES buffer (all from Mediatech). Hamster anti-mouse B7-H1 mAb (10B5) and PD-1 (G4) was obtained from hybridoma cells provided by L. Chen. Hamster anti-mouse B7-H1 mAb (43H12) was provided by K. Tamada (John Hopkins University).

Flow Cytometry Analysis:

Class I MHC ($K^b$OVA peptide SIINFEKL; SEQ ID NO:1) tetramer and negative control tetramer were purchased from Beckman Coulter. Fluorochrome-conjugated Abs against CD8, CD11a, Fas (CD95), Fas ligand, CD90.1 (Thy 1.1), CD90.2 (Thy 1.2), CD107a, IFNγ, IL-2 and TNFα were purchased from BD Biosciences, BioLegend, or eBiosciences. To detect intracellular cytokine levels, cells were incubated with GolgiPlug (BD Biosciences) for 4 hours prior to analysis. Cells were stained for surface antigens, and then incubated in Fixation Buffer (BioLegend) for 20 minutes at room temperature, followed by permeabilization in Permeabilization Wash Buffer (BioLegend). Fixed and permeabilized cells were then stained with Abs for 20 minutes at room temperature. Abs to Akt, Bcl-xL, Bcl-2, Bim and mTOR and fluorochrome-conjugated secondary Abs were purchased from Cell Signaling (Danvers, Mass.). To detect intracellular levels of Akt, Bcl-xL, Bcl-2, Bim and mTOR, T cells were first stained for surface antigens, then fixed with 2% paraformaldehyde for 10 minutes at 37° C., followed by permeabilization with ice-cold methanol for 30 minutes. After blocking with 15% rat serum for 15 minutes, cells were stained with Abs for 1 hour at room temperature. After staining, cells were washed three times with incubation buffer before analysis. At least 100,000 viable cells were live gated on FACScan or FACSCailbur (BD Biosciences) instrumentation. Flow cytometry analysis was performed using FlowJo software (Tree Star).

T-Cell Immunization, Activation, Apoptosis Assay and Proliferation Assay:

Mice were immunized by i.p. injection of 0.5 mg ovalbumin (OVA, from Sigma-Aldrich) and 50 µg poly (I:C) (Sigma Aldrich). For in vitro T-cell activation and apoptosis assay, purified CD8+ T cells were labeled with CFSE (Invitrogen-Molecular Probes) and incubated with OVA peptide$_{257-264}$ (Mayo Clinic Core Facilities) at 0.2 µg/mL for 72 hours. Apoptosis of CD8+ T cells was analyzed by staining using Annexin V (BD Biosciences) and TMRE (tetramethylrhodamine ethyl ester, Invitrogen/Molecular Probes T-669). Proliferation was also measured by detection of BrdU incorporation and Ki67 staining Immunized mice were injected i.p. with 0.8 mg/mL BrdU (BD Biosciences) on days 4 through 6 following immunization. On day 7 after immunization BrdU incorporation was determined by intranuclear staining with anti-BrdU (B9285, Sigma-Aldrich) and anti-Ki67 (556027, BD Biosciences).

In Vivo CTL Assay.

For the in vivo CTL assay, OVA$_{257-264}$ peptide-pulsed or control peptide-pulsed spleen cells (as target cells) from syngeneic mice were labeled with a high dose of CFSE (5 µM) or low dose of CFSE (0.5 µM), mixed at 1:1 ($2.5\times10^6$ of each) before injection. Target cells were i.v. injected into immunized mice on day 4 after re-challenge with cognate antigen protein. The CTL activity was determined 4 hours after target cell transfer. Specific lysis is calculated using the following formulas: ratio=(% CFSEhigh/% CFSElow),% specific lysis=[1−(ratio primed/ratio unprimed)]×100%.

Tumor Studies:

Mice were inoculated i.v. with $5\times10^5$ B16-OVA tumor cells on day 25 after immunization. On day 21-post tumor injection, mice were sacrificed and the lung tissue was perfused with PBS. The number of tumor foci on the lung tissue was counted.

T-Cell Transfer Experiments:

Purified CD8+ T cells ($1\times10^6$) from Thy1.1+OT-1 transgenic mice were i.v. injected into Thy 1.2+WT or B7-H1-deficient recipient mice, followed by immunization with OVA plus poly I:C. On day 7 after immunization, transferred CD8+ T cells were identified by their expression of Thy1.1 and used for detection of intracellular expression of Bim, Bcl-2 and Bcl-xL. Equal numbers of Cd80−/− (CD45.2+) and WT OT-1 (Thy1.1+, CD45.2+) CD8+ T cells ($10^6$ of each) were i.v. injected into CD45.1+ mice followed with immunization of OVA and poly I:C. The transferred OT-1 CD8+ T cells in the spleen were identified by flow cytometry.

In Vitro T-Cell Activation and Culturing with Fusion Proteins:

Spleen cells were harvested from naïve mice and pre-activated with ConA (5 µg/mL, L7647, Sigma-Aldrich) for 48 hours. Following activation, CD8+ T cells were purified (EasySep CD8+ T-cell negative selection kit, Stem Cell Technologies) and incubated with plate-bound anti-CD3 (BD Biosciences) and B7-H1 Fc fusion protein or control Fc protein (R&D Systems). Cultures were maintained for indicated time periods, and then cells were harvested for analysis.

Western Blotting:

Cells were lysed with NETN buffer (0.5% NP40, 150 mM NaCl, 50 mM Tris and 1 mM EDTA). Cell lysates were boiled and run on SDS-PAGE gels (BioRad), transferred to nitrocellulose membrane (Millipore), and blotted using standard procedures.

Quantitative RT-PCR:

Total RNA was isolated from purified CD8+ T cells (RNeasy Kit, Qiagen), and reverse transcribed (iScriptcDNA synthesis kit, BioRad). Samples were analyzed for Bim transcript levels using Bcl2l11 primers (Qiagen) and QuantiFast SYBR Green PCR Master Mix (Qiagen) on an iCycler (BioRad). GAPDH levels were used to normalize data by the comparative CT method.

Statistical Analysis:

A two-sided, unpaired or paired Student's t-test was used to assess statistical differences in experimental groups. A p value<0.05 was considered statistically significant.

Example 2—More Memory T Cells are Generated in the Absence of B7-H1

Figure 1:
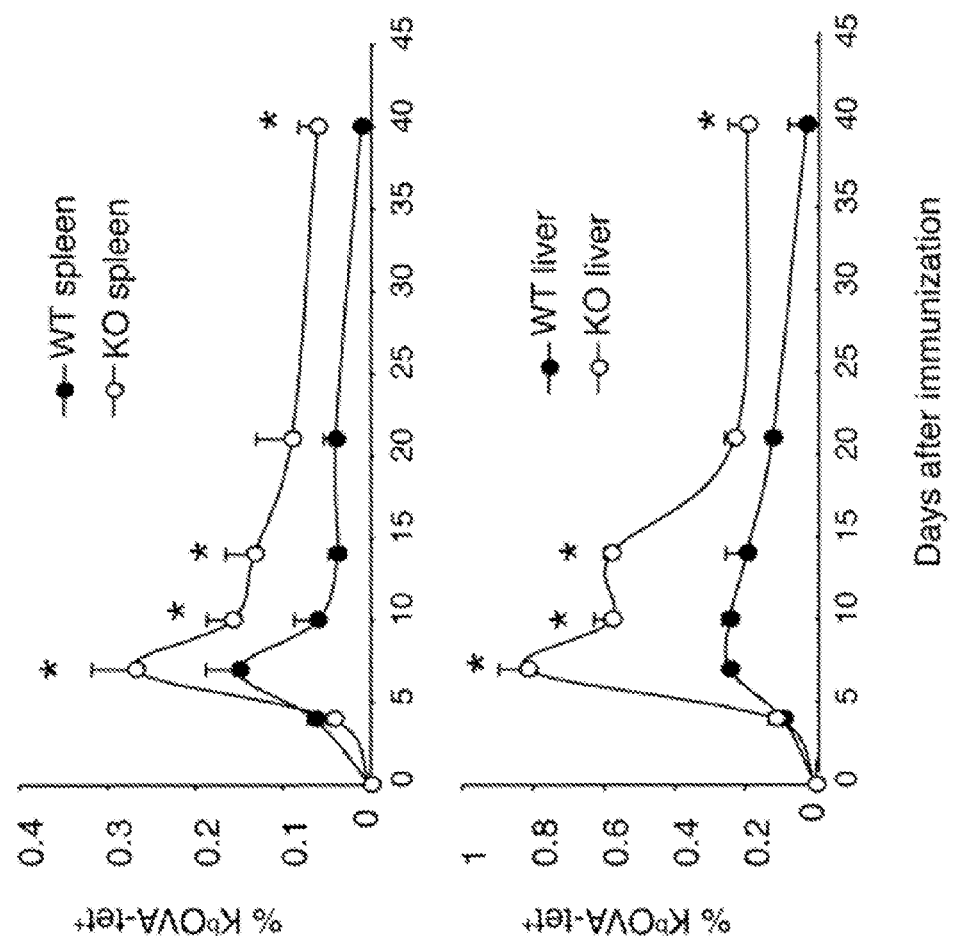
FIG. 1 contains a pair of graphs plotting the kinetics of CD8+ T-cell responses to antigen stimulation. Wild type (WT) and B7-H1-deficient (KO) mice were immunized (i.p.) with OVA plus poly I:C, and $K^b$/OVA tetramer was used to identify antigen-specific CD8+ T cells in spleen (top panel) and liver (bottom panel) at the indicated times after immunization. Data show the percentage of tetramer+ CD8+ T cells (mean±SD of three mice per time point). One of two independent experiments is shown. *$p<0.05$ compared with WT mice.

The kinetics of CD8+ T-cell responses in the spleen and liver of WT and B7-H1-deficient C57BL/6 mice were compared following immunization with ovalbumin (OVA) protein and polyinosinic:polycytidylic acid (poly (I:C)) as adjuvant. An increased number of CD8+ T cells was observed at the peak of the immune response (day 7-post immunization) in the spleen and liver of B7-H1-deficient mice as compared with WT mice. During the contraction phase (days 7 to 14 post-immunization), there was a significant delay in the reduction of antigen-specific CD8+ T cells in the spleen and liver of B7-H1-deficient mice as compared with WT mice. On day 40 following immunization, more antigen-specific memory CD8+ T cells were detected in B7-H1-deficient mice as compared with WT mice (FIG. 1). These data suggested that host B7-H1 may regulate the extent of expansion and contraction of effector CD8+ T cells, thus influencing the size of the memory CD8+ T-cell pool in both lymphoid and non-lymphoid tissues.

Figure 2:
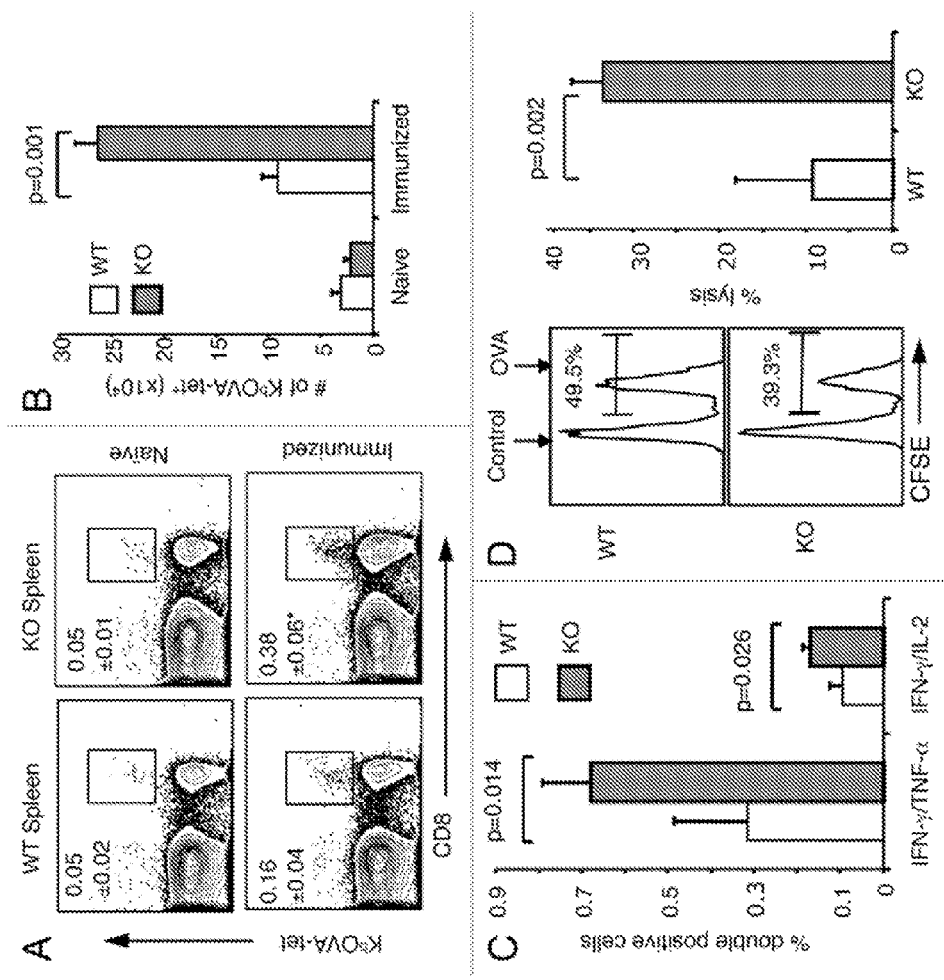
FIGS. 2A-2D contain a series of FACS scans and graphs showing enhanced memory CD8+ T-cell population in the absence of B7-H1. Mice were immunized with OVA plus poly I:C, and were re-stimulated with OVA on day 40 after immunization. On day 4 after re-stimulation, spleen cells were isolated from naïve or immunized WT and B7-H1-deficient mice for analysis.

Studies were conducted to examine the extent to which B7-H1 regulates the generation of memory CD8+ T cells in immunized mice, using $K^bOVA_{257-264}$ tetramer ($K^b$OVA-tet) to detect antigen-primed memory CD8+ T cells in the spleen on day 4 after in vivo restimulation (OVA protein, administered on day 40 after primary immunization). Day 4 was selected for analysis because at this time point it is possible to distinguish a recall response from the primary response (which takes 7 days to establish). Thus, naïve mice did not show a significant increase of antigen-specific CD8+ T cells on day 4 after immunization (FIG. 2A). The frequency of $K^b$OVA-tet+ CD8+ T cells increased more than 2-fold in immunized B7-H1-deficient mice (0.38%) as compared with WT mice (0.16%; p<0.05; FIG. 2A). This increase was reflected in the absolute cell numbers (p=0.001; FIG. 2B). In addition to having increased numbers of memory CD8+ T cells, an increased percentage of memory CD8+ T cells capable of producing multiple cytokines was detected in the spleens of B7-H1-deficient mice (0.73% IFNγ+/TNFα+, 0.17% IFNγ+/IL-2+) as compared with WT mice (0.24% IFNγ+/TNFα+, 0.07% IFNγ+/IL-2+; p<0.05; FIG. 2C). An in vivo CTL assay to measure cytolytic activity of the memory CD8+ T cells also was performed. On day 4 after in vivo re-stimulation, OVA peptide- or control peptide-pulsed target cells (syngeneic splenocytes labeled with either high or low CFSE) were injected into immunized WT and B7-H1-deficient mice. Four hours following cell injection, the remaining CFSE positive cells in the spleen were analyzed. Memory CD8+ T cells in the B7-H1-deficient mice lysed more OVA-peptide pulsed target cells (33.5%) than those in WT mice (9.3%, p<0.01; FIG. 2D). Collectively, these data suggest that B7-H1 negatively regulates the generation of memory CD8+ T cells in immunized mice.

Figure 3:
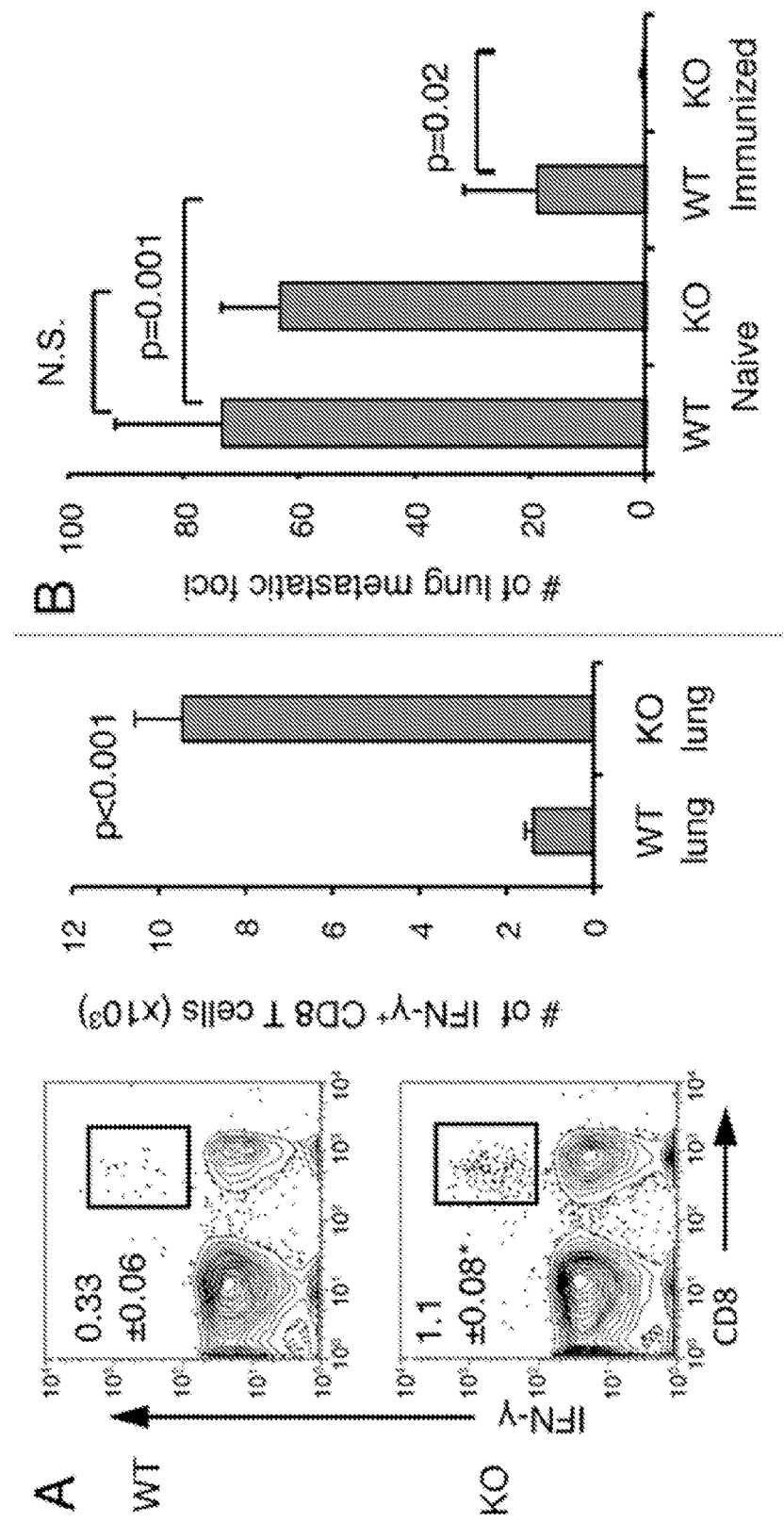
FIGS. 3A and 3B contain FACS scans and graphs showing enhanced memory CD8+ T-cell recall responses and improved antitumor immunity in the lung in the absence of B7-H1. On day 35 after immunization, immunized or naïve WT and B7-H1-deficient mice were injected (i.v.) with 5×10$^5$ B16-OVA tumor cells.

A hallmark of memory CD8+ T cells is their rapid recall response to cognate antigens, so studies were conducted to determine whether the increased memory pool in B7-H1-deficient mice would lead to a more protective recall response. B16-OVA melanoma tumor cells (engineered to express OVA) were injected into immunized WT and B7-H1-deficient mice. Intravenously injected B16-OVA tumor cells form metastases in the lung, and antitumor immunity can be monitored by counting the number of tumor foci. On day 4 following intravenous injection of $5\times10^5$ B16-OVA tumor cells, the frequency of functional memory CD8+ T cells in the lungs of WT and B7-H1-deficient mice was determined by intracellular staining for IFNγ. About 4 to 5-fold more IFNγ+CD8+ T cells were detected in the lungs of B7-H1-deficient mice as compared with WT mice (p<0.01; FIG. 3A). On day 21-post tumor injection, the number of tumor metastases in the lungs of naïve B7-H1-deficient mice was comparable to that of naïve WT mice (p=0.43; FIG. 3B). Fewer tumor metastases formed in the lungs of immunized WT mice as compared with naïve WT mice (p=0.001). Significantly, tumor metastases were completely rejected in the lungs of immunized B7-H1-deficient mice (FIG. 3B), suggesting that a more efficient CD8+ T-cell memory population is established in the absence of B7-H1.

Example 3—Bim Expression is Reduced in Antigen-Primed CD8+ T Cells in the Absence of B7-H1

Figure 4:
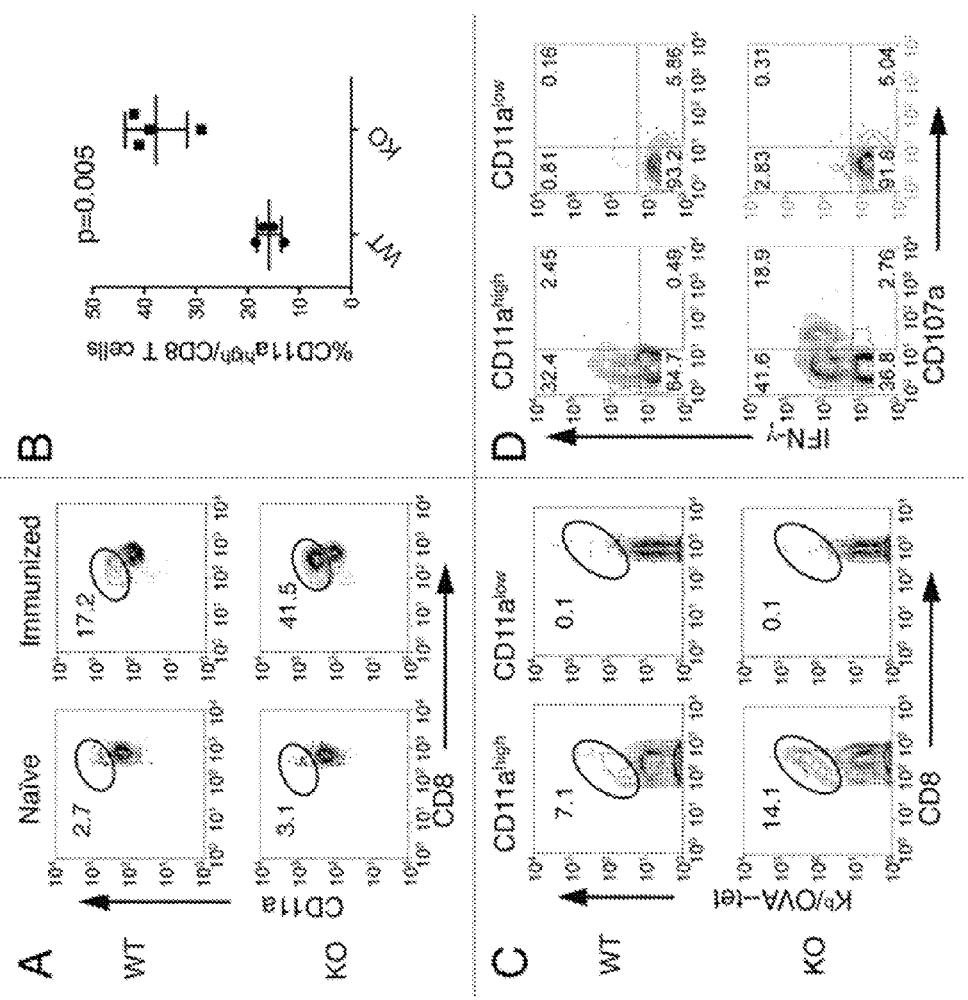
FIGS. 4A-4D contain a series of FACS scans and a graph showing that CD11a$^{high}$ CD8+ T cells represent antigen-primed effector T cells. Spleen cells from naïve or immunized WT and B7-H1-deficient mice were analyzed by co-staining with anti-C D11a and K$^b$/OVA tetramer or functional markers.

Studies were conducted to determine which mechanisms could be responsible for the increased population of memory CD8+ T cells in B7-H1-deficient mice by examining the proliferation and apoptosis of antigen-primed CD8+ T cells following immunization. CD11a was used as a surrogate activation marker. An advantage of this method is that $CD11a^{high}$ CD8+ T cells represent antigen-primed CD8+ T cells that are responsive to undefined antigen epitopes not recognized by tetramers. $CD11a^{high}$ CD8+ T cells were detected at low levels in the spleens of naïve WT and B7-H1-deficient mice (FIG. 4A). On day 7 after immunization, the percentage of $CD11a^{high}$ CD8+ T cells increased more than 2-fold in the spleens of B7-H1-deficient mice (41.5%) as compared with immunized WT mice (17.2%; p<0.01; FIGS. 4A and 4B), consistent with the results obtained by tetramer staining (FIG. 1). Seven to 15% of $CD11a^{high}$ CD8+ T cells from WT and B7-H1-deficient mice were specific for the known $H-2K^b$-restricted $OVA_{257-264}$ epitope based on tetramer staining, and $CD11a^{low}$ CD8+ T cells did not contain tetramer+ cells (FIG. 4C), suggesting that all antigen-specific CD8+ T cells are found in the $CD11a^{high}$ CD8+ T-cell population. In addition, the $CD11a^{high}$ CD8+ population from both WT and B7-H1-deficient mice, but not the $CD11a^{low}$ CD8+ T-cell population, produced IFNγ and underwent degranulation (indicated by CD107a surface expression) following ex vivo re-stimulation (FIG. 4D). As T-cell responses against diverse epitopes are coordinately regulated, these data further support the concept that the $CD11a^{high}$ CD8+ T-cell population represents true OVA-specific CD8+ T cells. Nearly 80-90% of OVA-induced $CD11a^{high}$ CD8+ T cells were reactive against undefined antigen epitopes of the OVA protein (FIG. 4C). Therefore, the $CD11a^{high}$ CD8+ T-cell population could be used to represent a majority of the antigen-primed CD8+ T cells during primary T-cell responses. In the following studies, $CD11a^{high}$ was used as a marker to track antigen-specific CD8+ T cells.

Figure 5:
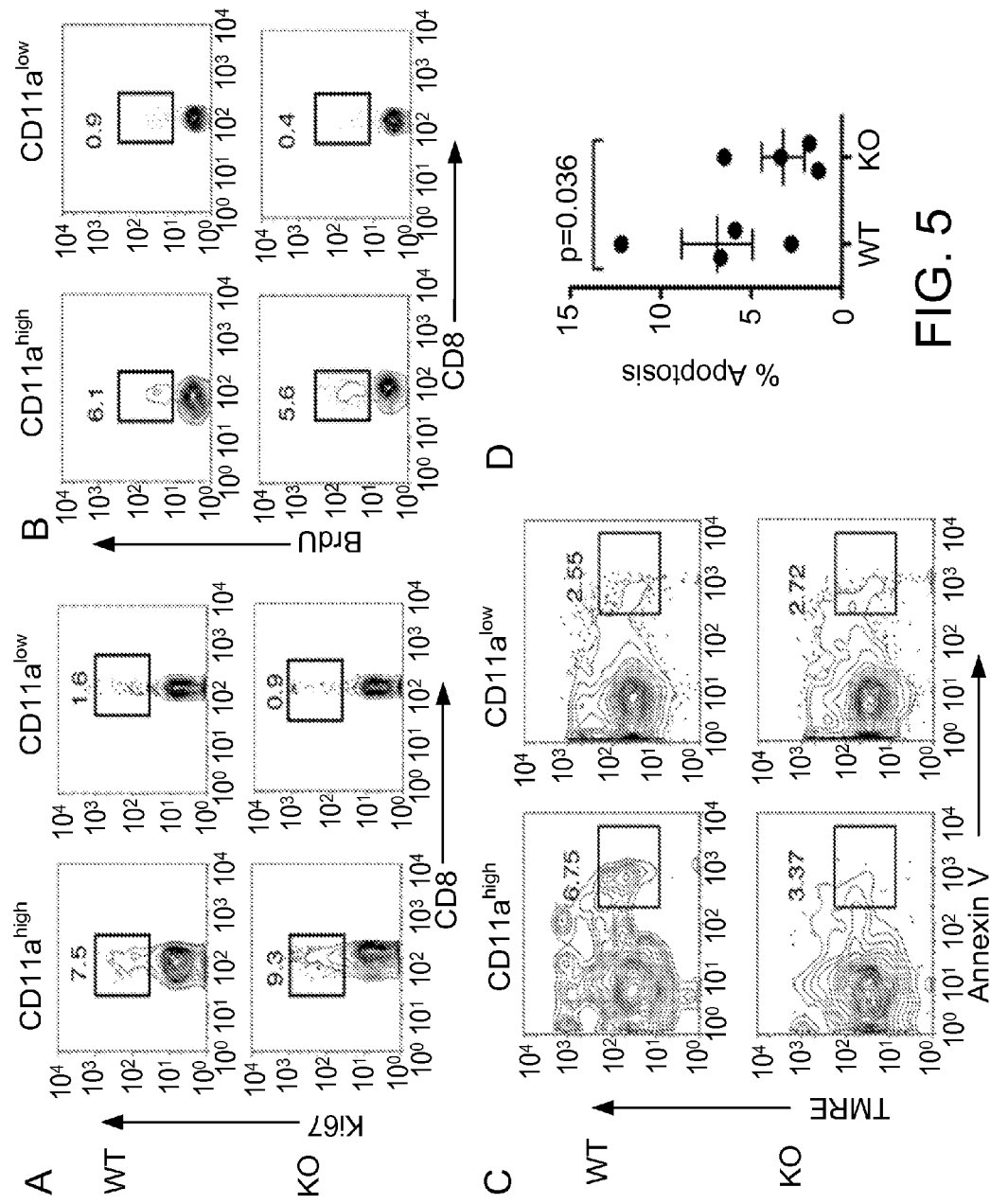
FIGS. 5A-5D contain a series of FACS scans and a graph showing fewer apoptotic antigen-primed CD8+ T cells in B7-H1-deficient mice. On day 7 after immunization, spleen cells were analyzed for proliferation and apoptosis.

The proliferation of effector CD8+ T cells following immunization was examined by staining cells for Ki67, a nuclear protein associated with cell proliferation (Gerdes et al. (1984) *J. Immunol.* 133:1710-1715). The percent of Ki67+ cells increased in $CD11a^{high}$ CD8+ T cells from B7-H1-deficient mice (9.32%) as compared with WT mice (7.5%), but this increase was not statistically significant (FIG. 5A). Proliferation also was monitored by performing a BrdU incorporation assay to measure the ongoing proliferation of CD8+ T cells following immunization. In this assay, the percentage of BrdU+ $CD11a^{high}$ CD8+ T cells also was similar between WT (6.05%) and B7-H1-deficient mice (5.59%; FIG. 5B). Ki67+ or BrdU+ cells were mainly detected in the $CD11a^{high}$ CD8+ T cells but not in $CD11a^{low}$ CD8+ T cells, suggesting that $CD11a^{high}$ CD8+ T cells are proliferating following antigen-stimulation (FIGS. 5A and 5B). These results suggested that the observed increased population of antigen-primed CD8+ T cells in B7-H1-deficient mice is not due to an increased proliferation of this cell compartment, as compared with WT mice.

Studies were then conducted to evaluate whether decreased apoptosis of antigen-primed CD8+ T cells could contribute to the observed increased population of antigen-primed CD8+ T cells in immunized B7-H1-deficient mice. As discussed above, the Fas/Fas ligand death receptor pathway is implicated in regulation of T-cell contraction, so the surface expression levels of Fas and Fas ligand on effector CD8+ T cells were measured on day 7 after immunization. Expression of Fas and Fas ligand was detected at similar levels in WT and B7-H1-deficient mice. These results suggest that the observed increased population of effector CD8+ T cells is not due to a change in Fas-induced apoptosis in B7-H1-deficient mice. The mitochondrial pathway for apoptosis was investigated by analyzing levels of Annexin V and tetramethylrhodamine ethyl ester (TMRE) staining TMRE is a fluorescent marker that is incorporated into intact mitochondria, and cells undergoing apoptosis show reduced TMRE staining as compared with live cells (Jayaraman, *J. Immunol. Methods* 306:68-79, 2005). These studies revealed that fewer antigen-primed $CD11a^{high}$ CD8+ T cells were undergoing apoptosis ($TMRE^{low}$ Annexin V+) in B7-H1-deficient mice (3.4%) as compared with WT mice (6.7%, p<0.05; FIGS. 5C and 5D). These results suggested that decreased levels of mitochondrial apoptosis may contribute to the observed increased population of antigen-primed CD8+ T cells in B7-H1-deficient mice.

Figure 6:
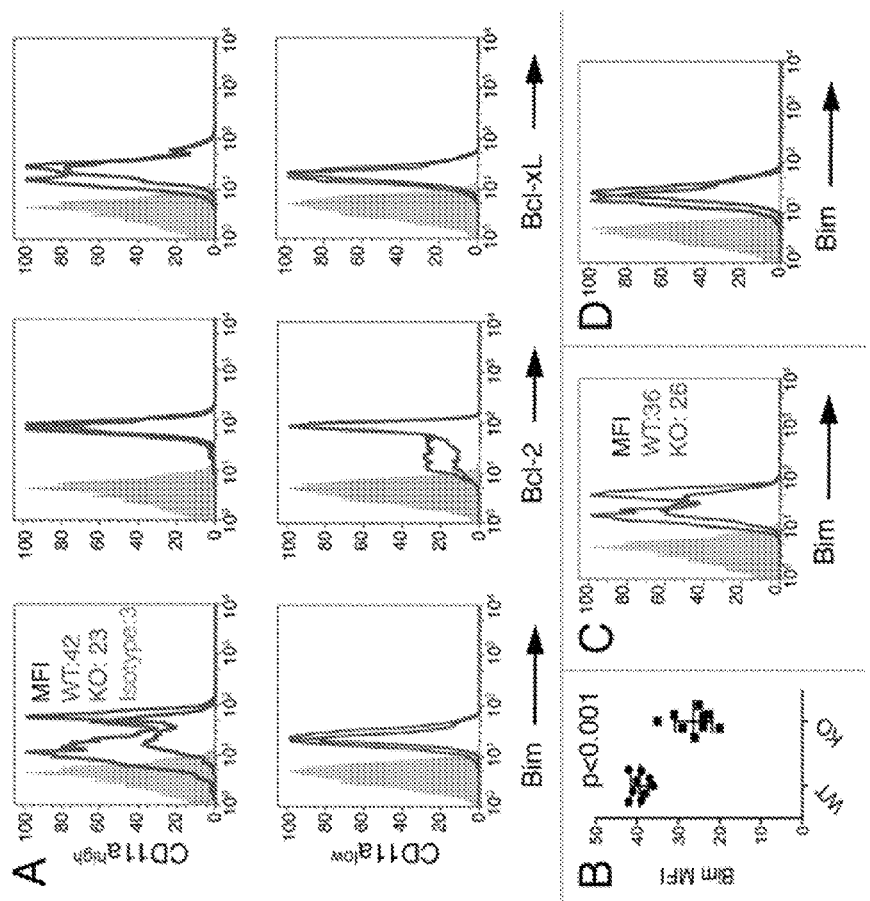
FIGS. 6A-6D contain a series of histograms and a graph showing lower Bim levels in antigen-primed CD8+ T cells in B7-H1-deficient mice.

Experiments were conducted to look for alterations in the expression of apoptosis-regulating molecules in effector CD8+ T cells. Intracellular levels of the pro-apoptotic molecule Bim and the anti-apoptotic molecules Bcl-2 and Bcl-xL were measured in $CD11a^{high}$ CD8+ T cells freshly isolated from the spleen on day 7 after immunization of naïve mice. Lower intracellular expression levels of Bim were observed in $CD11a^{high}$ CD8+ T cells from B7-H1-deficient mice than in the same cells obtained from WT mice (p<0.001; FIGS. 6A and 6B), while the expression levels of Bcl-2 and Bcl-xL were comparable in WT and B7-H1-deficient mice (FIG. 6A). The expression of Bim, Bcl-2 and Bcl-xL were comparable in $CD11a^{low}$ CD8+ T cells from B7-H1-deficient and WT mice (FIG. 6A). Intracellular expression levels of Bim also were analyzed in $CD11a^{high}$ CD8+ T cells isolated from the liver on day 7 after immunization of naïve mice. Again, lower intracellular expression levels of Bim were observed in $CD11a^{high}$ CD8+ T cells from B7-H1-deficient mice as compared with WT mice (FIG. 6C). Finally, intracellular expression levels of these proteins were examined in $CD11a^{high}$ CD8+ T cells isolated from the spleen of naïve mice, and no significant differences were observed in B7-H1-deficient vs. WT mice in the expression levels of Bim (FIG. 6D), Bcl-2 or Bcl-xL. These data suggested that the downregulation of the pro-apoptotic molecule Bim may contribute to the observed increased population of antigen-primed effector CD8+ T cells in B7-H1-deficient mice.

Figure 7:
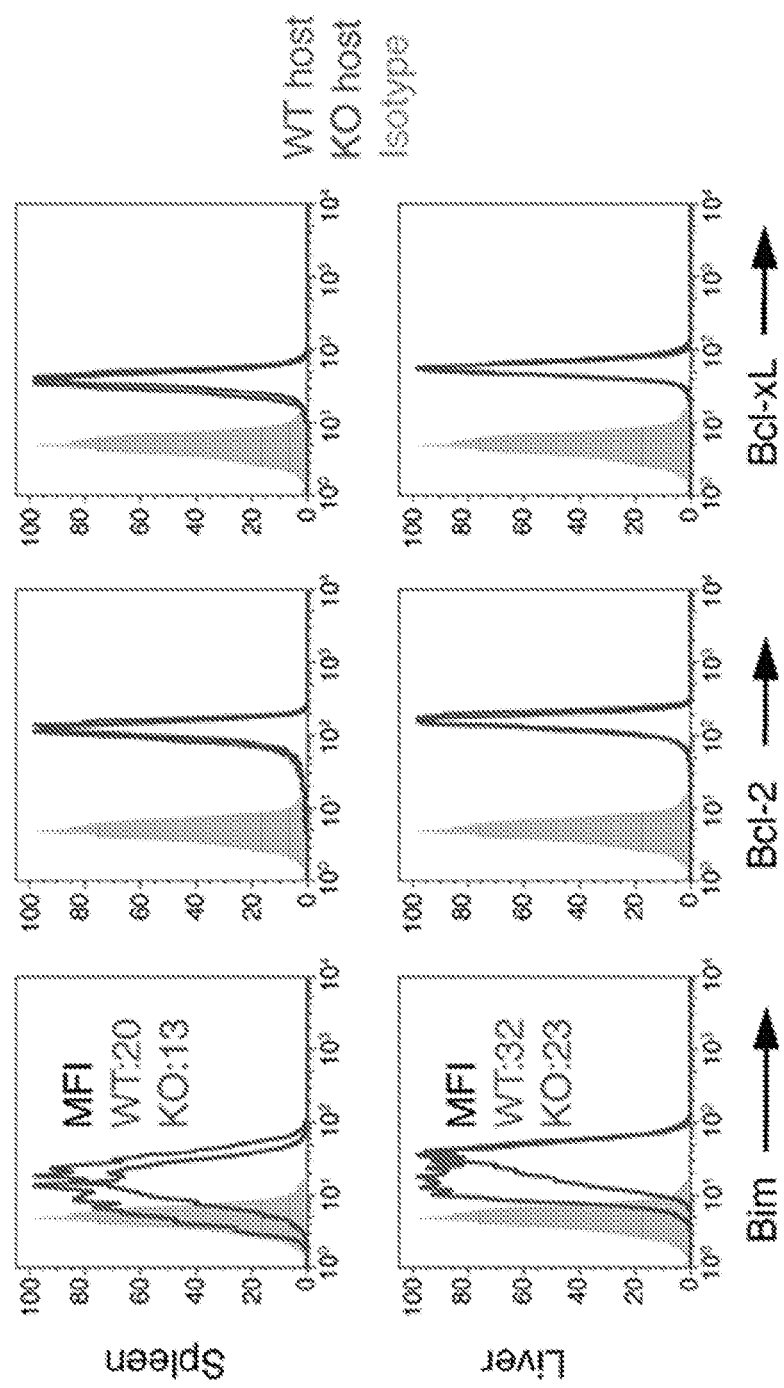
FIG. 7 contains a series of histograms showing the extrinsic role of B7-H1 in regulation of Bim. WT OT-1 CD8+ T cells (Thy1.1+) were transferred in WT (red) or B7-H1-deficient (blue) host mice one day before immunization with OVA plus poly I:C. On day 7 after immunization, the OT-1 CD8+ T cells in the spleen and liver were identified by the Thy1.1 marker and analyzed for intracellular expression of Bim. Numbers are MFI.

To exclude the possibility that the downregulation of Bim in B7-H1-deficient mice would be due to an intrinsic change in B7-H1-deficient T cells, transfer experiments were performed in which naïve OT-1 CD8+ T cells (Thy1.1+) were injected into WT or B7-H1-deficient mice (Thy1.2+). Following transfer of the OT-1 CD8+ T cells, host mice were immunized with OVA plus poly I:C. On day 7 after immunization, the intracellular levels of Bim, Bcl-2, and Bcl-xL were measured in transferred OT-1 CD8+ T cells freshly isolated from spleen and liver. OT-1 CD8+ T cells transferred into B7-H1-deficient hosts expressed lower levels of Bim in both the spleen and liver as compared with the OT-1 CD8+ T cells transferred into WT hosts (FIG. 7). The expression of Bcl-2 and Bcl-xL in OT-1 CD8+ T cells transferred into WT or B7-H1-deficient mice was comparable (FIG. 7). These data suggested that the downregulation of Bim in B7-H1-deficient mice is not due to an intrinsic change in B7-H1-deficient T cells, but rather to host B7-H1 interacting with one of its binding partners on CD8+ T cells.

Next, antibodies that block the interaction between B7-H1 and PD-1 or between B7-H1 and CD80 were used to examine if blocking either of these pathways would impact Bim expression levels. On days 1 and 3 after immunization of WT mice with OVA plus poly I:C, an anti-PD-1 antibody (G4) that only blocks PD-1 binding to B7-H1 (Hirano et al. (2005) *Cancer Res.* 65:1089-1096) or an anti-B7-H1 antibody (43H12) that only blocks B7-H1 binding to CD80 (Park et al. (2010) *Blood* 116:1291-1298) was injected. On day 7 after immunization, Bim expression levels in $CD11a^{high}$ CD8+ T cells were compared between groups with or without antibody blockade. Antibodies blocking the interaction between B7-H1 and PD-1 or between B7-H1 and CD80 both reduced the expression of Bim in primed CD8+ T cells as compared with control antibodies, whereas the expression of Bcl-2 and Bcl-xL remained unaffected. These results suggested that the downregulation of Bim in B7-H1-deficient mice might be due to a lack of interaction between B7-H1 and its binding partners, PD-1 and CD80.

After an acute viral infection, more central memory T cells accumulate in the lymphoid organs of PD-1-deficient mice as compared with WT mice, indicating that PD-1 signaling negatively regulates memory T-cell generation (Allie et al. (2011) *J. Immunol.* 186:6280-6286). The relevance of CD80 signaling in the regulation of memory generation was addressed by transferring equal numbers of CD80-deficient OT-1 and WT OT-1 naïve CD8+ T cells into CD45.1+ mice. One day after T-cell transfer, host mice were immunized with OVA plus poly I:C. On day 21 after immunization, the frequency and phenotype of the transferred CD80-deficient and WT OT-1 CD8+ T cells was analyzed. On day 21 after immunization, a 2-fold increased percentage of CD80-deficient OT-1 CD8+ T cells as compared with WT OT-1 CD8+ T cells was detected in the spleen, indicating that the transferred CD80-deficient OT-1 CD8+ T cells generated more memory T cells as compared with WT OT-1 CD8+ T cells. Surface staining confirmed that these cells had a central memory phenotype ($CD44^{hi}CD62L^{hi}$). The recall response of the memory population generated from transferred cells was investigated by injecting the hosts with OVA plus poly I:C on day 30 after the initial immunization, and 3 days later the frequency and phenotype of the transferred cells was analyzed. An increased percentage of CD80-deficient OT-1 CD8+ T cells as compared with WT OT-1 CD8+ T cells was detected in the spleen (p=0.013). Surface staining confirmed that these cells had an effector memory phenotype ($CD44^{hi}$ $CD62L^{lo}$). Taken together, these data demonstrated that Cd80−/− OT-1 CD8+ T cells generated more memory T cells as compared their WT counterparts, indicating that CD80 expressed by CD8+ T cells may negatively regulate memory T-cell generation.

Example 4—B7-H1 Enhances Bim Expression in Activated CD8+ T Cells

Figure 8:
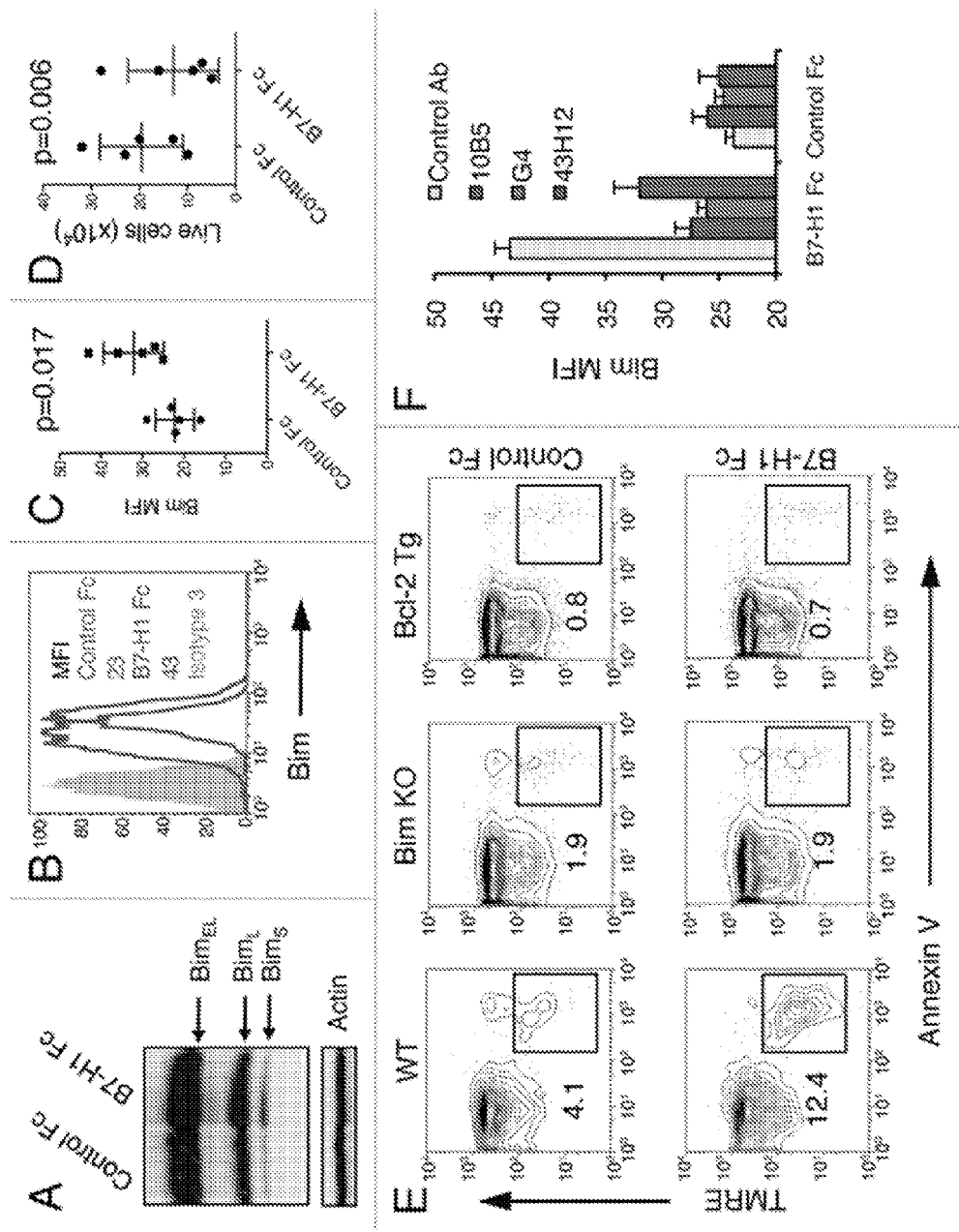
FIGS. 8A-8F show that B7-H1 co-stimulation induces upregulation of Bim protein levels in activated T cells. Pre-activated CD8+ T cells were incubated with platebound B7-H1 or control fusion protein (Fc) for 48 hours in the presence of anti-CD3.

Studies were conducted to investigate how B7-H1 might regulate Bim levels in activated CD8+ T cells. Pre-activated WT CD8+ T cells were incubated with platebound B7-H1 fusion protein for 48 hours in the presence of TCR stimulation (anti-CD3 antibody). Bim expression was analyzed by western blotting, and increased expression levels were observed in CD8+ T cells cultured in the presence of B7-H1 fusion protein, as compared with a control fusion protein (FIG. 8A). Bim expression also was analyzed by intracellular flow cytometry, revealing that the B7-H1 fusion protein dramatically increased the levels of Bim protein in CD8+ T cells compared with a control fusion protein (p<0.02; FIGS. 8B and 8C). In the absence of anti-CD3 antibodies, Bim levels did not increase upon incubation with B7-H1 fusion protein, suggesting that B7-H1 provides a co-stimulatory signal for Bim upregulation. Accordingly, the absolute number of live cells was also reduced in CD8+ T cells cultured in the presence of B7-H1 fusion protein compared with a control protein (p<0.01; FIG. 8D). Increased levels of cells undergoing apoptosis (TMRE$^{low}$ Annexin V+) were observed in cultures of activated CD8+ T cells exposed to the B7-H1 fusion protein and anti-CD3 (12.4%) as compared with cells cultured with control fusion protein and anti-CD3 (4.1%, FIG. 8E). The induction of apoptosis by B7-H1 fusion protein was lost in CD8+ T cells isolated from Bim-deficient and Bcl-2 transgenic mice (FIG. 8E), suggesting that B7-H1-induced T-cell apoptosis may be dependent on the Bim-mediated mitochondrial pathway of apoptosis.

To examine which receptor of B7-H1 is involved in mediating Bim upregulation, pre-activated WT CD8+ T cells were incubated with plate-bound B7-H1 fusion protein pre-blocked with anti-B7-H1 (10B5 or 43H12) or anti-PD1 (G4) antibodies. The 10B5 antibody blocks the interaction of B7-H1 with both PD-1 and CD80. Both 10B5 and G4 antibodies completely blocked Bim upregulation induced by B7-H1 fusion protein, while 43H12 only partially, but significantly, did so (FIG. 8F). None of the antibodies used in this experiment had effects on Bim expression levels in cells cultured with control fusion protein, indicating that their effect on Bim expression levels is due to blocking the interaction between B7-H1/PD-1 or B7-H1/CD80, and not due to a non-specific effect. These results suggest that B7-H1 may use PD-1 or CD80 on CD8+ T cells to deliver co-stimulatory signals for the upregulation of Bim.

Figure 9:
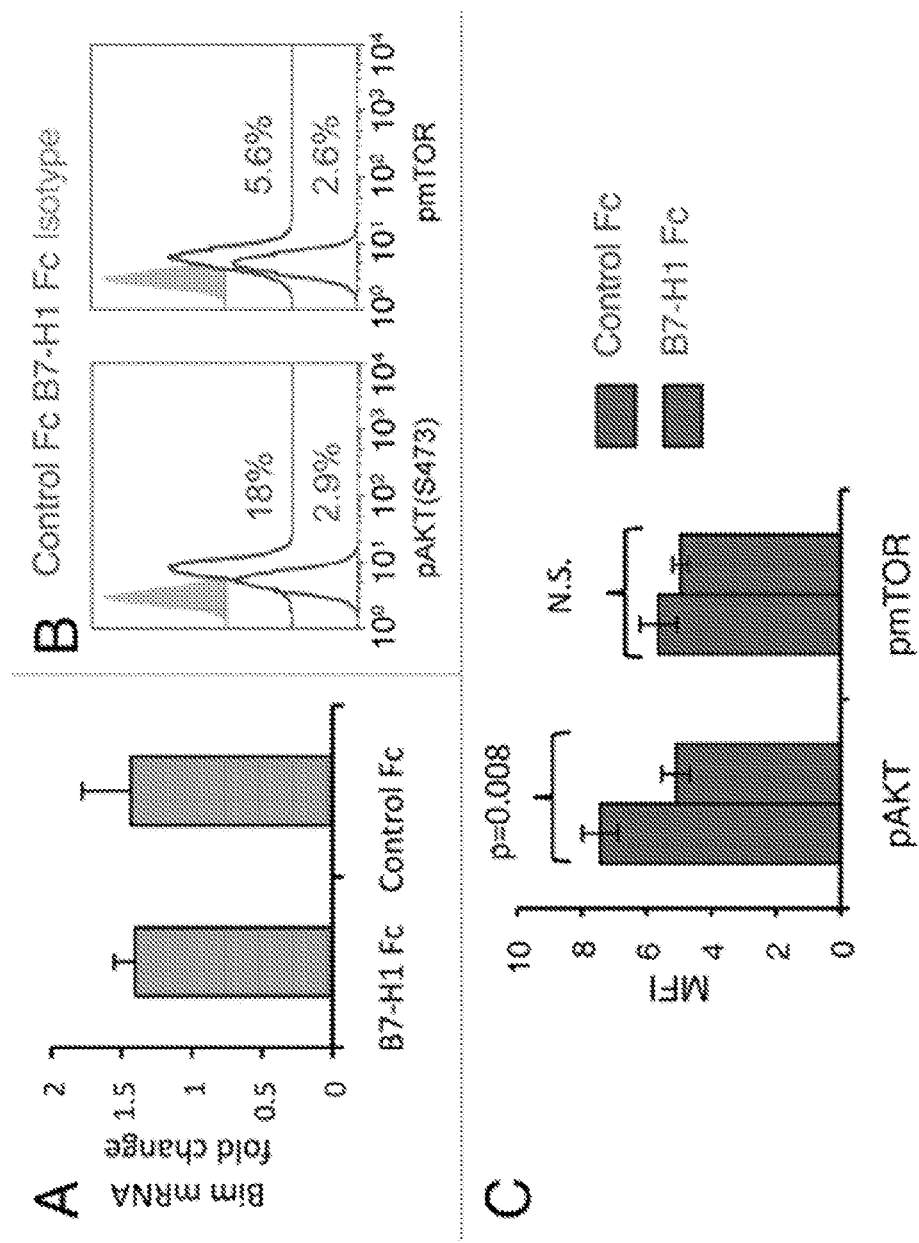
FIGS. 9A-9C contain a series of plots showing that B7-H1 co-stimulation inhibits activation of Akt. Pre-activated CD8+ T cells were stimulated with plate-bound B7-H1 or control fusion protein (Fc). After 24 hours of stimulation, CD8+ T cells were harvested and used for analysis.

The mechanism by which B7-H1 regulates Bim expression levels was then examined. mRNA levels of Bcl2l11, which encodes the Bim protein, were examined by quantitative real-time PCR analysis using mRNA isolated from pre-activated CD8+ T cells that were exposed to B7-H1 fusion protein or to a control fusion protein and anti-CD3 for 24 hours. Incubation of pre-activated CD8+ T cells with B7-H1 fusion protein did not increase the levels of Bcl2l11 (FIG. 9A), indicating that the B7-H1-mediated upregulation of Bim does not result from transcriptional regulation. The degradation of Bim is tightly regulated, at least in part via the activation of Akt followed by Akt-mediated Bim phosphorylation and degradation (Qi et al. (2006) *J. Biol. Chem.* 281:813-823). The level of Akt activation in CD8+ T cells after B7-H1 engagement was measured by intracellular flow cytometry for phosphorylated-Akt (Ser473). CD8+ T cells cultured with B7-H1 fusion protein exhibited decreased levels of phosphorylated Akt as compared with CD8+ T cells cultured with a control fusion protein (p<0.01; FIGS. 9B and 9C). As phosphorylation of Akt at Ser473 is regulated by activation of mTOR (Sarbassov et al. (2005) *Science* 307: 1098-1101; and Jacinto et al. (2006) *Cell* 127:125-137), studies were conducted to examine whether B7-H1 regulates phosphorylation of mTOR in vitro. Unexpectedly, there was no difference in levels of phospho-mTOR in CD8+ T cells cultured with B7-H1 fusion protein and cells cultured with control fusion protein (FIGS. 9B and 9C). These results suggested that CD8+ T-cell engagement with B7-H1 inhibits the activation of Akt, resulting in decreased degradation of Bim.

Figure 13:
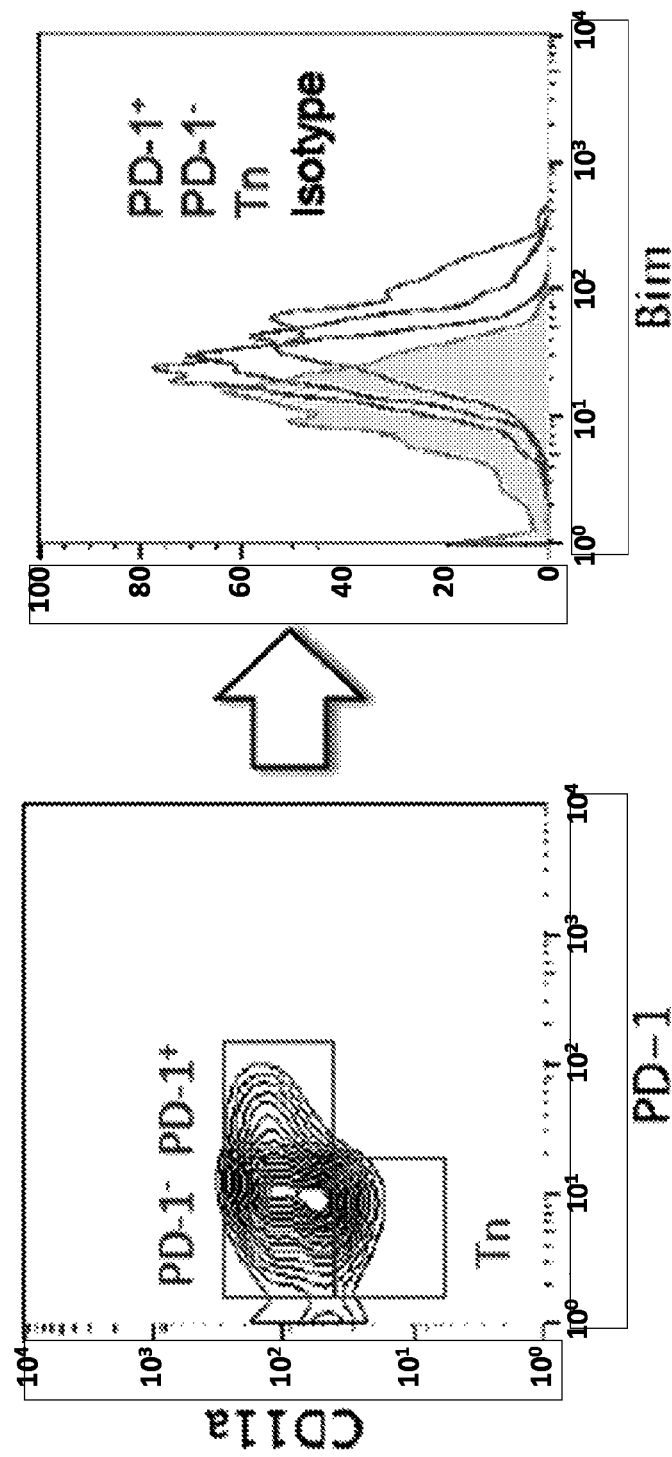
FIG. 13 contains a plot (left) showing the identification of CD8+ T cells based on their expression of CD11a$^{high}$ and PD-1+ (left panel). Lymphocytes were stained with CD8, CD11a and PD-1, followed by intracellular staining for Bim.

Example 5—Bim is Increased in Tumor-Reactive CD8+ T Cells in Peripheral Blood of Melanoma and Prostate Cancer Patients Peripheral blood lymphocytes were isolated from 26 patients with stage IV (advanced) melanoma, and from 11 healthy blood donors. Lymphocytes were stained with CD8, CD11a and PD-1 followed with intracellular staining for Bim. High expression of CD11a by CD8 T cells was used to identify antigen-primed T cells. Tumor-reactive CD8+ T cells were defined by their expression of CD11a$^{high}$ and PD-1+ (FIG. 13, left panel). The histograms shown in the right panel of FIG. 13 indicate expression of Bim by subsets of CD8+ T cells (Tn: T naïve cells; PD-1−, PD-1 negative primed cells; PD-1+, PD-1 positive primed cells). Of note, only PD-1+ primed cells (tumor-reactive) CD8+ T cells expressed high levels of Bim. Bim expression was increased in tumor-reactive CD8+ T cells in peripheral blood of melanoma patients as compared to the healthy controls, and also was increased in tumor-reactive CD8+ T cells in peripheral blood of prostate cancer patients as compared to healthy controls (FIG. 14). The Bim upregulation in melanoma patients was PD-1 dependent, as depicted in FIG. 15. When levels of Bim were compared between PD-1 negative (PD-1−) and PD-1 positive (PD-1+) CD11a$^{high}$ CD8+ T cells, Bim was found to be significantly increased in the PD-1+ populations (p=0.0081) in melanoma patients. In contrast, Bim expression was not increased in PD-1+ T cells in healthy donors, suggesting that Bim upregulation is dependent on PD-1 expression and is cancer-related.

Further, when melanoma patients were broken into "Bim low" vs. "Bim high" categories based on the level of Bim expression in tumor-reactive PD-1+CD11a$^{high}$ CD8+ T cells in the peripheral blood (FIG. 16, left panel), the survival rate for patients with Bim$^{high}$ PD-1+ CD8+ T cells was reduced as compared to the survival rate for patients with. Bim$^{low}$ PD-1+ CD8+ T cells (FIG. 16, right panel).

Example 6—B7-H1 Protein Induces High Expression of Bim in Human Pre-Activated CD8+ T Cells Since Bim up-regulation is a consequence of interaction between B7-H1 and PD-1, experiments were conducted to test whether an anti-PD-1 blocking antibody can reduce B7-H1-induced Bim up-regulation in T cells. An in vitro system was established in which pre-activated human primary CD8+ T cells were incubated with a B7-H1/PD-L1 fusion protein to induce Bim up-regulation. As shown in FIG. 17A (right panel), a significant up-regulation of Bim (presented as MFI) was induced the B7-H1/PD-L1 fusion (P<0.05, n=6). The increased Bim expression is further demonstrated by a flow cytometry histogram (FIG. 17A, left panel) and a Western blotting assay (FIG. 17B).

Using this system, several commercially available anti-human PD-1 antibodies were screened for their blocking effects, and one anti-PD-1 antibody (clone MIH4) was identified that significantly blocked B7-H1-induced Bim up-regulation in a dose dependent fashion (FIG. 18, left panel). Since B7-H1 induced different degrees of Bim up-regulation in individual healthy donors, experiments were conducted to examine whether different degrees of Bim up-regulation would affect the blocking effects of the anti-PD-1 antibody. Interestingly, it was observed that higher levels of Bim induced by B7-H1 had a negative correlation with Bim reduction by anti-PD-1 blocking antibody (FIG. 18, right panel; Pearson R=−0.71, n=12, P<0.05). These results suggested that pre-existing Bim levels in CD8+ T cells might affect the efficiency of anti-PD-1 blockade. Thus, measuring Bim levels before treatment could help to determine the degree to which an anti-PD-1 antibody might block the impact of PD-1 signals on antitumor T cell responses.

Example 7—Anti-PD-1 Treatment Reduced the Frequency of Bim+ PD-1+ Tumor-Reactive CD8 T Cells Next, studies were conducted to evaluate the impact of the anti-PD-1 antibody on Bim expression by tumor-reactive CD8 T cells in cancer patients. Peripheral blood lymphocytes were collected from patients with advanced melanoma (Stage IV) before and 12 weeks post anti-PD-1 treatment. Tumor-reactive CD8 T cells were identified by their high expression of CD11a and expression of PD-1. Bim expression was analyzed by intracellular staining. The percentage of Bim+PD-1+ in CD11a$^{high}$ CD8+ T cells was compared between healthy people and melanoma patients, and between melanoma patients before and after treatment with anti-PD-1 antibody. As shown in FIG. 19, the frequency of Bim+PD-1+CD8 T cells in the peripheral blood of melanoma patients (before treatment, n=29) was significantly higher than in the healthy control group (p=0.0012, n=14), suggesting that more PD-1+CD8 T cells are under the influence of the PD-1/B7-H1 interaction that leads to up-regulation of Bim. Importantly, twelve weeks after anti-PD-1 antibody therapy (2 mg/kg, one cycle), about 67% (6/9) of the melanoma patients demonstrated a significant reduction in the frequency of Bim+PD-1+ CD8 T cells (p=0.023, n=6). These results indicated that measurement of Bim expressed by PD-1+ CD8 T cells could be used to monitor the responses of cancer patients to anti-PD-1 therapy, which may block B7-H1-induced Bim up-regulation. A reduced frequency or level of Bim expressed by PD-1+ CD8 T cells in cancer patients after anti-PD-1 therapy may be used to assess which patients are responsive to the therapy.

Example 8—B7-H1 Expressed by Tumor Cells Induces Bim Up-Regulation in Human Pre-Activated CD8 T Cells Since most human solid tumor cells express elevated levels of B7-H1, the function of tumor cell-expressed B7-H1 in T cell Bim expression was examined. Pre-activated human primary CD8 T cells were incubated with cells from a human melanoma line (624mel) that were transfected with B7-H1 cDNA or with control mock cDNA, for 24 hours. As shown in FIG. 20, intracellular expression of Bim was dramatically increased in CD8 T cells cultured with B7-H1/624mel cells, as compared to mock/624mel cells (p<0.01). This result suggested that B7-H1 expressed by human tumor cells has the potential to up-regulate Bim in pre-activated CD8 T cells.

Example 9—Bim Expression is Associated with B7-H1 Expression in Human RCC

The ability of B7-H1 to up-regulate Bim in pre-activated, but not newly activated, CD8+ T cells, implied that reactivation of tumor-reactive CD8+ T cells at tumor sites could be dampened through this mechanism by B7-H1 positive tumor cells. To test this possibility, human cancer tissues stained for B7-H1 and Bim were evaluated. The hypothesis was that B7-H1 positive human cancer tissues would be associated with more Bim positive tumor-infiltrating lymphocytes (TILs). As shown in FIG. 21 (left panel), human renal cell carcinoma tissues were stained with anti-B7-H1 and anti-Bim antibodies in immunohistochemistry assays. B7-H1 reactivity was identified on the surface of cancer cells, while Bim positive staining was identified on cancer cells and also on TILs (FIG. 21, left panel). Bim reactivity was determined by an arbitrary scoring system: 0 (absence), 1 (focal), 2 (moderate), and 3 (marked). The association between B7-H1 positive or negative tumors and the frequency of Bim reactivity at different levels is demonstrated in the right panel of FIG. 21, and was analyzed using Fisher's exact test. B7-H1 positive tumors were found in general to have a higher degree (2-3 scores) of Bim positive TILs than B7-H1 negative tumors (Fisher's exact test, p<0.01). These results suggest that B7-H1 positive tumors can induce more death in tumor-reactive T cells at tumor sites via up-regulation of Bim when these T cells are re-activated with tumor antigen stimulation.

Example 10—Bim Expression is Correlated with Granzyme B and T-Bet Expressed by Cancer-Related PD-1+CD11a$^{high}$ CD8+ T Cells To examine whether up-regulation of Bim is associated with effector T cells, the levels of Granzyme B (an executive molecule of cytotoxic T lymphocytes, CTL) and T-bet (a transcription factor of CTL) were measured in PD-1+ CD11a$^{high}$ CD8 T cells from the blood of melanoma patients, and their correlation to Bim levels was analyzed. As shown in FIG. 22, positive correlations between levels of Bim and Granzyme B (left panel; r=0.51, p<0.05) and between levels of Bim and T-bet (right panel; r=0.62, p<0.01) were observed. These results suggested that higher levels of Bim expression are associated with effector T cell differentiation or function. These data also imply that up-regulation of Bim may be used by B7-H1 positive tumor cells to induce apoptosis of tumor-reactive CD8 T cells, especially of CD8 T cells with effector function.

Example 11—Bim Expression Declines in PD-1+ CD11a$^{high}$ CD8 T Cells Following Radiotherapy in Some Cancer Patients To observe how the levels of Bim in tumor-reactive CD8 T cells respond to therapy, Bim levels were measured in PD-1+ CD11a$^{high}$ CD8 T cells from the peripheral blood of patients with melanoma and prostate cancers before and post radiotherapy. As shown in FIG. 23 (left panel), decreased levels of Bim were observed in melanoma patients post radiotherapy. In contrast, increased levels of Bim were observed in prostate cancer patients post radiotherapy (right panel). Due to the limited numbers of patients in this study, these changes did not reach statistical significance. However, these changes in Bim levels after tumor cytotoxic therapy suggested that destruction of tumor tissues could alter the antigen stimulation and B7-H1 expression that would result in alterations in Bim expression, which is dependent on both antigen stimulation and B7-H1 engagement with PD-1 on CD8 T cells. Taken together, these studies indicate that measurement of Bim levels in tumor-reactive PD-1+CD8 T cells could be used as a biomarker to monitor T cell responses to antigens and PD-1 ligands (e.g., B7-H1) expressed by human tumor cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying a mammal having cancer as being likely to benefit from checkpoint blockade therapy and treating said mammal, wherein said method comprises:
   (a) identifying a mammal as containing an elevated level of Bim and having a tumor that expresses B7-H1, and
   (b) administering to said mammal an anti-PD-1 antibody under conditions wherein the interaction of naturally-occurring B7-H1 with PD-1 in said mammal is reduced after said administering.

2. The method of claim 1, wherein said mammal is a human.

3. The method of claim 1, wherein said elevated level of Bim is based on Bim protein levels.

4. The method of claim 1, wherein said elevated level of Bim is based on the level of mRNA encoding Bim.

5. The method of claim 1, wherein said cancer is a melanoma cancer, a breast cancer, a lung cancer, a renal cell carcinoma cancer, a pancreas cancer, a prostate cancer, a colon cancer, a brain cancer, a liver cancer, or an ovarian cancer.

6. A method for treating a mammal having cancer, wherein said method comprises administering an anti-PD-1 antibody to a mammal identified as containing an elevated level of Bim and having a tumor that expresses B7-H1, and thus identified as being likely to benefit from checkpoint blockade therapy, wherein said administering is under conditions wherein interaction of naturally-occurring B7-H1 with PD-1 in said mammal is reduced.

7. The method of claim 6, wherein said mammal is a human.

8. The method of claim 6, wherein said elevated level of Bim is based on Bim protein levels.

9. The method of claim 6, wherein said elevated level of Bim is based on the level of mRNA encoding Bim.

10. The method of claim 6, wherein said cancer is a melanoma cancer, a breast cancer, a lung cancer, a renal cell carcinoma cancer, a pancreas cancer, a prostate cancer, a colon cancer, a brain cancer, a liver cancer, or an ovarian cancer.

* * * * *